(12) United States Patent
Xu et al.

(10) Patent No.: US 11,266,649 B2
(45) Date of Patent: Mar. 8, 2022

(54) PHARMACEUTICAL FORMULATIONS

(71) Applicant: Corvus Pharmaceuticals, Inc., Burlingame, CA (US)

(72) Inventors: Jingrong Xu, Burlingame, CA (US); William Jones, Burlingame, CA (US); Felicia Flicker, Burlingame, CA (US); Bret Berner, Burlingame, CA (US)

(73) Assignee: Corvus Pharmaceuticals, Inc., Burlingame, CA (US)

( * ) Notice: Subject to any disclaimer, the term of this patent is extended or adjusted under 35 U.S.C. 154(b) by 108 days.

(21) Appl. No.: 16/963,461

(22) PCT Filed: Feb. 1, 2019

(86) PCT No.: PCT/US2019/016284
§ 371 (c)(1),
(2) Date: Jul. 20, 2020

(87) PCT Pub. No.: WO2019/152798
PCT Pub. Date: Aug. 8, 2019

(65) Prior Publication Data
US 2021/0060020 A1 Mar. 4, 2021

Related U.S. Application Data

(60) Provisional application No. 62/625,163, filed on Feb. 1, 2018.

(51) Int. Cl.
*A61K 31/519* (2006.01)
*A61K 9/16* (2006.01)
(Continued)

(52) U.S. Cl.
CPC .......... *A61K 31/519* (2013.01); *A61K 9/1676* (2013.01); *A61K 9/1694* (2013.01);
(Continued)

(58) Field of Classification Search
None
See application file for complete search history.

(56) References Cited

U.S. PATENT DOCUMENTS 8,450,328 B2 * 5/2013 Bamford .............. C07D 487/04
514/261.1
2006/0111334 A1 5/2006 Mueller et al.
(Continued)

FOREIGN PATENT DOCUMENTS

WO WO-2004/098570 A1 11/2004
WO WO-2008/021347 A2 2/2008
(Continued)

OTHER PUBLICATIONS

Curatolo, W. et al. (Jun. 2009, e-published Mar. 10, 2009). "Utility of Hydroxypropylmethylcellulose Acetate Succinate (HPMCAS) for Initiation and Maintenance of Drug Supersaturation in the GI Milieu." *Pharmaceutical Research* (26)6:1419-1431.
(Continued)

*Primary Examiner* — Melissa S Mercier
(74) *Attorney, Agent, or Firm* — Mintz, Levin, Cohn, Ferris, Glovsky and Popeo, P.C.

(57) ABSTRACT

The disclosure provides, inter alia, pharmaceutical compositions comprising micronized drug particles of adenosine A2A receptor antagonists, and methods of treating cancer using the pharmaceutical compositions.

16 Claims, 4 Drawing Sheets

(51) Int. Cl.

| | | |
|---|---|---|
| *A61K 9/28* | (2006.01) | |
| *A61K 9/48* | (2006.01) | |
| *A61K 47/02* | (2006.01) | |
| *A61K 47/14* | (2017.01) | |
| *A61K 47/26* | (2006.01) | |
| *A61K 47/34* | (2017.01) | |
| *A61K 47/38* | (2006.01) | |

(52) U.S. Cl.
CPC .............. *A61K 9/28* (2013.01); *A61K 9/4866* (2013.01); *A61K 47/02* (2013.01); *A61K 47/14* (2013.01); *A61K 47/26* (2013.01); *A61K 47/34* (2013.01); *A61K 47/38* (2013.01)

(56) References Cited

U.S. PATENT DOCUMENTS

| | | |
|---|---|---|
| 2011/0172252 A1 | 7/2011 | Bamford et al. |
| 2015/0073146 A1 | 3/2015 | Dahanukar et al. |
| 2015/0359735 A1 | 12/2015 | Herry et al. |
| 2017/0088552 A1 | 3/2017 | Bamford et al. |
| 2019/0231783 A1 | 8/2019 | Xu et al. |

FOREIGN PATENT DOCUMENTS

| | | |
|---|---|---|
| WO | WO-2008/021347 A3 | 8/2008 |
| WO | WO-2009/027337 A1 | 3/2009 |
| WO | WO-2011/050160 A1 | 4/2011 |
| WO | WO-2013/128283 A2 | 9/2013 |
| WO | WO-2013/149981 A1 | 10/2013 |
| WO | WO-2016/209787 A1 | 12/2016 |
| WO | WO-2017/112917 A1 | 6/2017 |
| WO | WO-2018/013951 A1 | 1/2018 |
| WO | WO-2017/112917 A8 | 7/2018 |

OTHER PUBLICATIONS

Evonik. (2020). *The Global Market Leader for Enteric Release Coatings*. Enteric Release Solutions—Evonik Health Care. Retrieved Mar. 3, 2020, from https://healthcare.evonik.com/product/health-care/en/products/pharmaceutical-excipients/delayed-release/ 5 Pages.

Ghebremeskel, A.N. et al. (2007, e-published Aug. 17, 2006). "Use of surfactants as plasticizers in preparing solid dispersions of poorly soluble API: Selection of polymer-surfactant combinations using solubility parameters and testing the processability", *International Journal of Pharmaceutics* (328)2:119-129.

International Preliminary Report on Patentability issued in International Application No. PCT/US2019/16284, dated Aug. 4, 2020. 11 pages.

International Search Report and Written Opinion issued in International Application No. PCT/US2019/16284, dated Jul. 5, 2019. 22 pages.

Leuner, C et al. (2000). "Improving drug solubility for oral delivery using solid dispersions", *European Journal of Pharmaceutics and Biopharmaceutics* (50)1:47-60.

Meere, M. et al. (2019). "Modelling Phase Separation In Amorphous Solid Dispersions." *Acta Biomaterialia* (94):25 pages.

SciFinder. (2020). *Search structure for Formula III*. Retrieved Feb. 28, 2020, 27 Pages.

Ticagrelor. (Nov. 24, 2015), in *Wikipedia*. https://web.archive.org/web/20160125052903/https://en.wikipedia.org/wiki/Ticagrelor. 5 Pages.

Aiken, Chris (2016). "The impact of particles on pharmaceuticals," pp. 1-3. XP055847872, Retrieved from the Internet: URL:https://www.outsourcing-pharma.com/Headlines/Promotional-Features/The-impact-of-particles-on-pharmaceuticals [retrieved on Oct. 5, 2021].

European Search Report issued in European patent application No. 19746980.2, dated Oct. 19, 2021 (dated Oct. 19, 2021). 18 pages.

Sun, Zhigang et al. (2010). "Particle Size Specifications for Solid Oral Dosage Forms: A Regulatory Perspective," American Pharmaceutical Review, pp. 1-10. XP055099380, Retrieved from the Internet:URL:http://www.americanpharmaceuticalreview.com/Featured-Articles/36779-Particle-Size-Specifications-for-Solid-Oral-Dosage-Forms-A-Regulatory-Perspective/ [retrieved on Jan. 30, 2014].

* cited by examiner

PHARMACEUTICAL FORMULATIONS

CROSS-REFERENCE TO RELATED APPLICATIONS

This application is a Section 371 US National Phase of International Application No. PCT/US19/16284 filed Feb. 1, 2019, which claims priority to U.S. Application No. 62/625,163 filed Feb. 1, 2018, the disclosure of which is incorporated by reference herein in its entirety.

BACKGROUND

The goal of immunotherapy is to drive cytotoxic T-cell responses to eradicate cancer. To prevent reaction to self-antigens multiple inhibitory checkpoint signals exist. Extracellular adenosine is produced during acute, inflammatory processes by conversion from adenosine triphosphate through ectonucleotidases CD73 and CD39 expressed on the cell surface of multiple tissue types. Adenosine is normally upregulated to protect a host from over-injury in response to such stimuli as infection or ischemia by binding to its extracellular, G-protein coupled receptors on target cells and begin healing. However, multiple tumor types can actively sustain extracellular adenosine levels well beyond acute phase reactions to dampen a host's immune response through multiple mechanisms. Increases in adenosine in the microenvironment by malignant cells recruit regulatory T-cells to the area and further drive up adenosine levels.

Cancer cells appear to directly utilize adenosine. As a result, adenosine causes inefficient presentation of tumor antigens to the adaptive system and enhances tumor growth. Thus, adenosine A2A receptor antagonists have been designed, and are in clinical development, to treat cancer. Accordingly, there is a need in the art for formulations of adenosine A2A receptor antagonists that would provide the ideal combination of exposure, safety, and/or stability attributes necessary for commercial pharmaceutical products. To that end, studies have been conducted, as described herein, to develop such formulations that, e.g., have improved bioavailability, are stable at room temperature, and minimize the potential of gastric irritation. The disclosure is directed to these, as well as other, important ends.

BRIEF SUMMARY

Provided herein are pharmaceutical compositions comprising micronized drug particles and a pharmaceutically acceptable excipient; wherein the micronized drug particles comprise an adenosine receptor antagonist. In aspects, the micronized drug particles have a size distribution with a D90 of about 30 microns or less, as measured by laser diffraction spectroscopy. In aspects, the micronized drug particles have a size distribution with a D90 of about 20 microns or less, as measured by laser diffraction spectroscopy. In aspects, the adenosine A2A receptor antagonist is a compound of Formula (I), a compound of Formula (II), a compound of Formula (III), a compound of Formula (IIIA), a compound of Formula (TIM), or a pharmaceutically acceptable salt of one of the foregoing. In aspects, the micronized drug particles are crystalline. In aspects, the pharmaceutically acceptable excipient comprises (i) a filler, such as a polyol, maltodextrin, microcrystalline cellulose, dicalcium phosphate, or a combination of two or more thereof; (ii) a disintegrant, such as carboxymethyl cellulose, sodium starch glycolate, a crosslinked polyvinylpyrrolidone polymer, or a combination of two or more thereof; (iii) a binder, such as a hydroxyalkyl cellulose, an alkyl cellulose, corn starch, polyethylene glycol, polyethylene oxide, polyvinylpyrrolidone, or a combination of two or more thereof; or (iv) a combination of two or more of a filler, a disintegrant, and a binder. In aspects, the pharmaceutical compositions are in the form of a tablet, capsule, or powder. In aspects, the pharmaceutical compositions comprise about 10 wt % to about 40 wt % of the adenosine A2A receptor antagonist, about 40 wt % to about 80 wt % of a filler, about 1 wt % to about 20 wt % of a disintegrant, and about 1 wt % to about 20 wt % of a binder. In aspects, the compositions comprise from about 1 mg to about 1,000 mg of the adenosine A2A receptor antagonist. In aspects, the compositions have an outer coating.

Provided herein are granules comprising micronized drug particles and a pharmaceutically acceptable excipient; wherein the micronized drug particles comprise an adenosine receptor antagonist. In aspects, the micronized drug particles have a size distribution with a D90 of about 30 microns or less, as measured by laser diffraction spectroscopy. In aspects, the micronized drug particles have a size distribution with a D90 of about 20 microns or less, as measured by laser diffraction spectroscopy. In aspects, the adenosine A2A receptor antagonist is a compound of Formula (I), a compound of Formula (II), a compound of Formula (III), a compound of Formula (IIIA), a compound of Formula (TIM), or a pharmaceutically acceptable salt of one of the foregoing. In aspects, the micronized drug particles are crystalline. In aspects, the pharmaceutically acceptable excipient comprises (i) a filler, such as a polyol, maltodextrin, microcrystalline cellulose, dicalcium phosphate, or a combination of two or more thereof; (ii) a disintegrant, such as carboxymethyl cellulose, sodium starch glycolate, a crosslinked polyvinylpyrrolidone polymer, or a combination of two or more thereof; (iii) a binder, such as a hydroxyalkyl cellulose, an alkyl cellulose, corn starch, polyethylene glycol, polyethylene oxide, polyvinylpyrrolidone, or a combination of two or more thereof; or (iv) a combination of two or more of a filler, a disintegrant, and a binder. In aspects, the granules comprise about 10 wt % to about 40 wt % of the adenosine A2A receptor antagonist, about 40 wt % to about 80 wt % of a filler, about 1 wt % to about 20 wt % of a disintegrant, and about 1 wt % to about 20 wt % of a binder. In aspects, lubricants, glidants, or surfactants may be included either internal or external to the granules. In aspects, the granules have an outer coating. In aspects, the granules, optionally with an outer coating, are compressed into a tablet, are placed within a capsule shell or are placed within a sachet or stick pack.

Provided herein are tablets comprising micronized drug particles and a pharmaceutically acceptable excipient; wherein the micronized drug particles comprise an adenosine receptor antagonist. In aspects, the micronized drug particles have a size distribution with a D90 of about 30 microns or less, as measured by laser diffraction spectroscopy. In aspects, the micronized drug particles have a size distribution with a D90 of about 20 microns or less, as measured by laser diffraction spectroscopy. In aspects, the adenosine A2A receptor antagonist is a compound of Formula (I), a compound of Formula (II), a compound of Formula (III), a compound of Formula (IIIA), a compound of Formula (TIM), or a pharmaceutically acceptable salt of one of the foregoing. In aspects, the micronized drug particles are crystalline. In aspects, the pharmaceutically acceptable excipient comprises (i) a filler, such as a polyol, maltodextrin, microcrystalline cellulose, dicalcium phosphate, or a combination of two or more thereof; (ii) a disintegrant, such as carboxymethyl cellulose, sodium starch glycolate, a crosslinked polyvinylpyrrolidone polymer, or a combination of two or more thereof; (iii) a binder, such as a hydroxyalkyl cellulose, an alkyl cellulose, corn starch, polyethylene glycol, polyethylene oxide, polyvinylpyrrolidone, or a combination of two or more thereof; or (iv) a combination of two or more of a filler, a disintegrant, and a binder. In aspects, the tablets comprise about 10 wt % to about 40 wt % of the adenosine A2A receptor antagonist, about 40 wt % to about 80 wt % of a filler, about 1 wt % to about 20 wt % of a disintegrant, and about 1 wt % to about 20 wt % of a binder. In aspects, the tablets comprise from about 1 mg to about 600 mg of the adenosine A2A receptor antagonist. In aspects, the tablets include surfactants, glidants, lubricants, or a combination thereof. In aspects, the tablets have an outer coating.

Provided herein are powders comprising micronized drug particles and a pharmaceutically acceptable excipient; wherein the micronized drug particles comprise an adenosine receptor antagonist. In aspects, the micronized drug particles have a size distribution with a D90 of about 30 microns or less, as measured by laser diffraction spectroscopy. In aspects, the micronized drug particles have a size distribution with a D90 of about 20 microns or less, as measured by laser diffraction spectroscopy. In aspects, the adenosine A2A receptor antagonist is a compound of Formula (I), a compound of Formula (II), a compound of Formula (III), a compound of Formula (IIIA), a compound of Formula (TIM), or a pharmaceutically acceptable salt of one of the foregoing. In aspects, the micronized drug particles are crystalline. In aspects, the pharmaceutically acceptable excipient comprises (i) a filler, such as a polyol, maltodextrin, microcrystalline cellulose, dicalcium phosphate, or a combination of two or more thereof; (ii) a disintegrant, such as carboxymethyl cellulose, sodium starch glycolate, a crosslinked polyvinylpyrrolidone polymer, or a combination of two or more thereof; (iii) a binder, such as a hydroxyalkyl cellulose, an alkyl cellulose, corn starch, polyethylene glycol, polyethylene oxide, polyvinylpyrrolidone, or a combination of two or more thereof; or (iv) a combination of two or more of a filler, a disintegrant, and a binder. In aspects, the powder comprises about 10 wt % to about 40 wt % of the adenosine A2A receptor antagonist, about 40 wt % to about 80 wt % of a filler, about 1 wt % to about 20 wt % of a disintegrant, and about 1 wt % to about 20 wt % of a binder. In aspects, the powder comprises from about 1 mg to about 1,000 mg of the adenosine A2A receptor antagonist. The powder can be used as a single dose or multiple doses, which can be multiplied by the intended number of doses or dosage forms more generally. In aspects, the powder further comprises surfactants, glidants, lubricants, or a combination of two or more thereof. In aspects, the powder is compressed into a tablet, placed within a capsule shell or placed within a sachet or stick pack. In aspects, the powder is measured out and administered directly or mixed with food or a liquid.

Provided herein are oral formulations comprising micronized drug particles and a pharmaceutically acceptable excipient; wherein the micronized drug particles comprise an adenosine receptor antagonist. In aspects, the micronized drug particles have a size distribution with a D90 of about 30 microns or less, as measured by laser diffraction spectroscopy. In aspects, the micronized drug particles have a size distribution with a D90 of about 20 microns or less, as measured by laser diffraction spectroscopy. In aspects, the adenosine A2A receptor antagonist is a compound of Formula (I), a compound of Formula (II), a compound of Formula (III), a compound of Formula (IIIA), a compound of Formula (IIIB), or a pharmaceutically acceptable salt of one of the foregoing. In aspects, the micronized drug particles are crystalline. In aspects, the pharmaceutically acceptable excipient comprises (i) a filler, such as a polyol, maltodextrin, microcrystalline cellulose, dicalcium phosphate, or a combination of two or more thereof; (ii) a disintegrant, such as carboxymethyl cellulose, sodium starch glycolate, a crosslinked polyvinylpyrrolidone polymer, or a combination of two or more thereof; (iii) a binder, such as a hydroxyalkyl cellulose, an alkyl cellulose, corn starch, polyethylene glycol, polyethylene oxide, polyvinylpyrrolidone, or a combination of two or more thereof; or (iv) a combination of two or more of a filler, a disintegrant, and a binder. In aspects, the oral formulations are in the form of a tablet, capsule, or powder. In aspects, the oral formulations comprise about 10 wt % to about 40 wt % of the adenosine A2A receptor antagonist, about 40 wt % to about 80 wt % of a filler, about 1 wt % to about 20 wt % of a disintegrant, and about 1 wt % to about 20 wt % of a binder. In aspects, the oral formulations comprise from about 1 mg to about 1,000 mg of the adenosine A2A receptor antagonist. In aspects, the oral formulations further comprise surfactants, glidants, lubricants, or a combination of two or more thereof. In aspects, the oral formulations have an outer coating.

Provided herein are beads comprising an inert core and a drug layer; wherein the outer layer comprises micronized drug particles and a pharmaceutically acceptable excipient; wherein the micronized drug particles comprise an adenosine receptor antagonist. In aspects, the micronized drug particles have a size distribution with a D90 of about 30 microns or less, as measured by laser diffraction spectroscopy. In aspects, the micronized drug particles have a size distribution with a D90 of about 20 microns or less, as measured by laser diffraction spectroscopy. In aspects, the adenosine A2A receptor antagonist is a compound of Formula (I), a compound of Formula (II), a compound of Formula (III), a compound of Formula (IIIA), a compound of Formula or a pharmaceutically acceptable salt of one of the foregoing. In aspects, the micronized drug particles are crystalline. In aspects, the pharmaceutically acceptable excipient comprises (i) a filler, such as a polyol, maltodextrin, microcrystalline cellulose, dicalcium phosphate, or a combination of two or more thereof; (ii) a disintegrant, such as carboxymethyl cellulose, sodium starch glycolate, a crosslinked polyvinylpyrrolidone polymer, or a combination of two or more thereof; (iii) a binder, such as a hydroxyalkyl cellulose, an alkyl cellulose, corn starch, polyethylene glycol, polyethylene oxide, polyvinylpyrrolidone, or a combination of two or more thereof; or (iv) a combination of two or more of a filler, a disintegrant, and a binder. In aspects, the beads comprise about 10 wt % to about 40 wt % of the adenosine A2A receptor antagonist, about 40 wt % to about 80 wt % of a filler, about 1 wt % to about 20 wt % of a disintegrant, and about 1 wt % to about 20 wt % of a binder. In aspects, the beads further comprise surfactants, glidants, lubricants, or a combination of two or more thereof. In aspects, the beads have an outer coating. In aspects, the beads, optionally with an outer coating, are compressed into a tablet, are placed within a capsule shell, or are placed within a sachet or stick pack.

Provided herein are capsules having encapsulated within the capsule shell, such as a hypromellose capsule shell, the pharmaceutical compositions, granules, powders, or beads described herein. In aspects, the capsule shell comprises an enteric polymer. In aspects, the capsules have an outer coating. In aspects, the capsules comprise from about 1 mg to about 600 mg of the adenosine A2A receptor antagonist.

Provided herein are pharmaceutical compositions comprising an adenosine A2A receptor antagonist (e.g. a compound of Formula (III)) wherein the adenosine A2A receptor antagonist in the composition has a dissolution of at least 70% in 60 minutes as s measured by US Pharmacopeia (USP), Chapter <711>, Type II (Paddle) Dissolution Apparatus. In aspects, the dissolution is at least 75% in 60 minutes. In aspects, the dissolution is at least 80% in 60 minutes. In aspects, the dissolution is at least 85% in 60 minutes. In aspects, the dissolution is at least 90% in 60 minutes. In aspects, the dissolution is at least 70% in 10 minutes. In aspects, the dissolution is at least 60% in 10 minutes.

Provided herein are pharmaceutical compositions comprising an adenosine A2A receptor antagonist (e.g. a compound of Formula (III)) having a disintegration time of 15 minutes or less, as measured by laser diffraction spectroscopy as measured by US Pharmacopeia (USP), Chapter <701>, Disintegration Test. In aspects, the pharmaceutical compositions have a disintegration time of about 15 minutes or less, as measured by laser diffraction spectroscopy. In aspects, the pharmaceutical compositions have a disintegration time of about 10 minutes or less, as measured by laser diffraction spectroscopy. In aspects, the pharmaceutical compositions have a disintegration time of about 5 minutes or less, as measured by laser diffraction spectroscopy.

Provided herein are methods of treating cancer in patients by administering therapeutically effective amounts of the pharmaceutical compositions, oral formulations, tablets, capsules, granules, powders, or beads described herein to treat the cancer. In aspects, the cancer is lung cancer (e.g., non-small cell lung cancer), melanoma (e.g., malignant melanoma), renal cell cancer, breast cancer (e.g., triple negative breast cancer), colorectal cancer, bladder cancer, prostate cancer, or a head and neck cancer. In aspects, the pharmaceutical compositions, oral formulations, tablets, capsules, granules, powders, or beads described herein are administered to the patient once daily (QD). In aspects, one daily administration may comprise administration of 1, 2, or 3 oral formulations (e.g., 1, 2, or 3 tablets or capsules). In aspects, the pharmaceutical compositions, oral formulations, tablets, capsules, granules, powders, or beads described herein are administered to the patient twice daily (BID). In aspects, twice daily administration may comprise administration of 1, 2, or 3 oral formulations (e.g., 1, 2, or 3 tablets or capsules) twice daily. In aspects, the therapeutically effective amount for cancer treatment is from about 1 mg per day to about 1,000 mg per day. In aspects, a therapeutically effective amount for cancer treatment in adult humans is from about 50 mg to about 600 mg per day. In aspects, a therapeutically effective amount for cancer treatment in human pediatrics or veterinary applications may be from about 5 mg to about 400 mg per day.

The disclosure provides processes for preparing the pharmaceutical compositions, oral formulations, and granules described herein by mixing the micronized adenosine A2A receptor antagonist with at least one pharmaceutically acceptable excipient to form granules; drying and milling or sieving the granules; and filling the granules into a capsule or compressing the granules to form a tablet; and optionally applying a coating to the capsule or tablet.

The pharmaceutical compositions and oral formulations (e.g., tablets, capsules, granules, powders, beads) described herein have unexpectedly superior properties. In aspects the pharmaceutical compositions and oral formulations (e.g., tablets, capsules, granules, powders, beads) described herein have unexpectedly superior bioavailability. In aspects the pharmaceutical compositions and oral formulations (e.g., tablets, capsules, granules, powders, beads) described herein have unexpectedly superior stability. In aspects the pharmaceutical compositions and oral formulations (e.g., tablets, capsules, granules, powders, beads) described herein have an unexpectedly superior dissolution profile. In aspects the pharmaceutical compositions and oral formulations (e.g., tablets, capsules, granules, powders, beads) described herein have an unexpectedly superior disintegration profile. In aspects the pharmaceutical compositions and oral formulations (e.g., tablets, capsules, granules, powders, beads) described herein have unexpectedly superior pharmacokinetic properties. In aspects the pharmaceutical compositions and oral formulations (e.g., tablets, capsules, granules, powders, beads) described herein have unexpectedly superior $C_{min}$, $C_{max}$, ratio of $C_{max}/C_{min}$, $T_{max}$, or AUC.

These and other embodiments and aspects of the disclosure are set forth herein.

BRIEF DESCRIPTION OF THE FIGURE

With reference to FIG. 2, P16K108003A is Pharmaceutical Composition No. 1; P16K108003B is Pharmaceutical Composition No. 2; and P16K108003C is Pharmaceutical Composition No. 3.

FIG. 3A shows the dissolution profile of Pharmaceutical Composition No. 1 (P16K108003A). FIG. 3B shows the dissolution profile of Pharmaceutical Composition No. 2 (P16K108003B). FIG. 3C shows the dissolution profile of Pharmaceutical Composition No. 3 (P16K108003C).

DETAILED DESCRIPTION

Definitions

Figure 1:
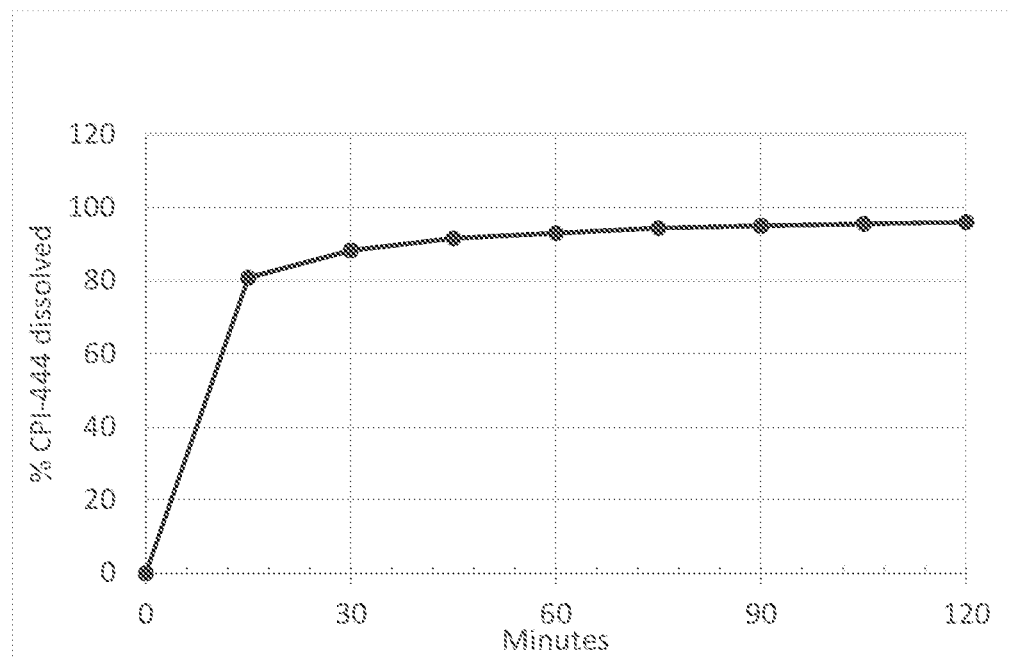
FIG. 1 shows the dissolution of Pharmaceutical Composition No. 5 in the US Pharmacopoeia (USP), Chapter <711>, Dissolution Test, wherein the composition is placed in a USP Apparatus 2 at a paddle speed of 50 rpm, in a dissolution medium of 0.1N HCl, 900 mL, at about 37° C.

The term "drug particle" or "drug particles" as used herein means a particle(s) composed of A2A receptor antagonists or pharmaceutically acceptable salts thereof. In aspects, the drug particle is a solid. In aspects, the drug particle is a semi-solid. In aspects, the drug particle includes no other active pharmaceutical ingredients other than one or more A2A receptor antagonists. In aspects, the drug particle includes only a single type of A2A receptor antagonist. In aspects, the drug particle includes only a single type of A2A receptor antagonist and no other active pharmaceutical ingredient. In aspects, the drug particle includes only a single type of A2A receptor antagonist and no pharmaceutical excipients or other active pharmaceutical ingredients. In aspects, the drug particle includes only a single type of A2A receptor antagonist, optionally water molecules, and no pharmaceutical excipients or other active pharmaceutical ingredients. In aspects, the drug particles are crystalline. In aspects, drug particles are amorphous. In aspects, the drug particle or drug particles refer to all the drug particles in the composition.

"Micronized drug particles" refers to drug particles having a particle size distribution with a D90 of about 50 microns or less, as measured by laser diffraction spectroscopy. In aspects, the drug particles have a size distribution with a D90 of about 40 microns or less, as measured by laser diffraction spectroscopy. In aspects, the drug particles have a size distribution with a D90 of about 30 microns or less, as measured by laser diffraction spectroscopy. In aspects, the drug particles have a size distribution with a D90 of about 25 microns or less, as measured by laser diffraction spectroscopy. In aspects, the drug particles have a size distribution with a D90 of about 20 microns or less, as measured by laser diffraction spectroscopy. In aspects, the drug particles have a size distribution with a D90 of about 15 microns or less, as measured by laser diffraction spectroscopy. In aspects, the drug particles have a size distribution with a D90 of about 10 microns or less, as measured by laser diffraction spectroscopy. In aspects, the micronized drug particles refer to all the drug particles in the composition.

"Particle size distribution" or "PSD" or "size distribution" refers to the size of particles present in their relative proportions in a sample, as measured by laser diffraction spectroscopy. In aspects, the particle size distribution refers to the particle size distribution of all the drug particles in the composition. The particle size distribution of a sample is measured by laser diffraction spectroscopy. Laser diffraction spectrometers are commercially available as, e.g., MASTERSIZER® 3000 from Malvern Instruments Ltd, and HORIBA® LA-950 by Horiba Instruments, Inc., Irvine Calif. For laser diffraction spectroscopy, particle size distribution is generally described by D values, such as D90. In aspects, the laser diffraction spectroscopy can be analyzed by the Fraunhofer theory. In aspects, the laser diffraction spectroscopy can be analyzed by the Mie scattering theory. In aspects, the laser diffraction spectroscopy can be analyzed by a combination of the Fraunhofer theory and the Mie scattering theory.

"D90" is the point in particle size distribution in which 90% of the total volume of material (e.g., drug particles) in the sample is below that specified size, as measured by laser diffraction spectroscopy. That is, D90 refers to a particle size distribution in which 90% of the total volume of material of drug particles in a sample is below a specified size. For example, if the D90 is 20 microns, this means that 90% of the materials in the sample have a particle size of 20 microns or less. "D90" is also known as Dv(90) or $D_{90}$. The particle size distribution of a sample is measured by laser diffraction spectroscopy. Laser diffraction spectrometers are commercially available as, e.g., MASTERSIZER® 3000 from Malvern Instruments Ltd, and HORIBA® LA-950 by Horiba Instruments, Inc., Irvine Calif.

"D50" is the point in particle size distribution in which 50% of the total volume of material (e.g., drug particles) in the sample is below that specified size. That is, D50 refers to a particle size distribution in which 50% of the total volume of material of drug particles in a sample is below a specified size. For example, if the D50 is 6 microns, this means that 50% of the materials in the sample have a particle size of 6 microns or less. "D50" is also known as Dv(50) or $D_{50}$. The particle size distribution of a sample is measured by laser diffraction spectroscopy. Laser diffraction spectrometers are commercially available as, e.g., MASTERSIZER® 3000 from Malvern Instruments Ltd, and HORIBA® LA-950 by Horiba Instruments, Inc., Irvine Calif.

"D10" is the point in particle size distribution in which 10% of the total volume of material (e.g., drug particles) in the sample is below that specified size. That is, D10 refers to a particle size distribution in which 10% of the total volume of material of drug particles in a sample is below a specified size. For example, if the D10 is 1.8 microns, this means that 10% of the materials in the sample have a particle size of 1.8 microns or less. "D10" is also known as Dv(10) or $D_{10}$. The particle size distribution of a sample is measured by laser diffraction spectroscopy. Laser diffraction spectrometers are commercially available as, e.g., MASTERSIZER® 3000 from Malvern Instruments Ltd, and HORIBA® LA-950 by Horiba Instruments, Inc., Irvine Calif.

"Crystalline" refers to a compound that has an ordered, three-dimensional lattice of atoms and/or molecules, as determined by methods known in the art, such as X-ray powder diffraction, IR-spectroscopy, Raman spectroscopy, differential scanning calorimetry (DSC), solid-state NMR, polarized light microscopy, or by its melting point. See, e.g., Remington: The Science and Practice of Pharmacy, $21^{st}$ Ed., Lippincott, Williams and Wilkins, Baltimore, Md. (2005); The United States Pharmacopeia, 23rd Ed., (1995). To be clear, where a compound is disclosed herein as being crystalline, a person having ordinary skill in the art will immediately recognize that the compound forms part of a crystalline solid that includes a plurality of that compound.

"Amorphous" refers to a solid compound (i.e. a solid that includes a plurality of a compound) or a solid composition without long-range crystalline order. In aspects, amorphous refers to a compound or composition that is substantially free of crystalline forms. That is, amorphous refers to a solid that includes a compound (e.g. a plurality of pharmaceutically active agents or drugs) wherein the solid is substantially free of crystalline forms. In aspects, an amorphous compound (i.e. a solid that includes a plurality of a compound) or composition has less than 10% of the compound (i.e. a solid that includes a plurality of a compound) or composition in a crystalline form; or less than 5%; or less than 2% of the compound (i.e. a solid that includes a plurality of a compound) or composition in crystalline form. In aspects, an amorphous compound or composition has less than 1% of the compound (i.e. a solid that includes a plurality of a compound) or composition in crystalline form. In aspects, an amorphous compound (i.e. a solid that includes a plurality of a compound) or composition does not have crystallinity as determined by X-ray powder diffraction, IR-spectroscopy, Raman spectroscopy, differential scanning calorimetry (DSC), solid-state NMR, polarized light microscopy, or by its melting point. In aspects, an amorphous compound (i.e. a solid that includes a plurality of a compound), an amorphous solid dispersion, an amorphous composition (i.e. a solid that includes a plurality of a composition), or an amorphous extrudate, as described herein, remain amorphous for a period of time longer than 18 months; longer than 2 years; longer than 3 years; longer than 4 years; or longer than 5 years. To be clear, where a compound (e.g. drug or active agent) is disclosed herein as being amorphous, a person having ordinary skill in the art will immediately recognize that the compound forms part of an amorphous solid that includes a plurality of that compound. Likewise, where a compound is disclosed herein as being a solid (e.g. "solid compound"), a person having ordinary skill in the art will immediately recognize that the compound forms part of a solid that includes a plurality of that compound.

"Pharmaceutically acceptable excipient" refers to a substance that aids the administration of an adenosine A2A receptor antagonist to and absorption by a patient, or to a substance that assists in the manufacture of the granules, beads, powders, tablets, compositions, and formulations described herein. Pharmaceutically acceptable excipients are inert. Non-limiting examples of pharmaceutically acceptable excipients include pharmaceutically acceptable polymers, water, NaCl, normal saline solutions, normal sucrose, normal glucose, binders, fillers, disintegrants, lubricants, surfactants, coatings, sweeteners, flavors, salt solutions, alcohols, oils, gelatins, carbohydrates, colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like. Pharmaceutically acceptable excipients are described in the Handbook of Pharmaceutical Excipients, 8$^{th}$ Edition, published by the Pharmaceutical Press (2017), and in the United States Food and Drug Administration Inactive Ingredient Database (July 2017), the disclosures of which are incorporated by reference herein. The pharmaceutical compositions (including granules, beads, powders, tablets, capsules, and oral formulations) described herein may comprise one or more pharmaceutically acceptable excipients. One of skill in the art will recognize that other pharmaceutically acceptable excipients would be useful in the compositions descried herein.

A "filler" is a pharmaceutically acceptable excipient used in pharmaceutical compositions to add volume to low-dose active ingredients. Exemplary fillers include polyols, maltodextrin, microcrystalline cellulose, and the like. Other fillers will be known to those skilled in the art.

A "disintegrant" is a pharmaceutically acceptable excipient that expands and/or dissolves when exposed to water or bodily fluids (e.g., gastric acid, saliva) that cause pharmaceutical composition to break apart (generally in the digestive tract, such as the stomach, small intestine, or large intestine) and release the active ingredient. In aspects, the disintegrant is a super disintegrant. Exemplary disintegrants include carboxyalkyl cellulose (e.g., carboxymethyl cellulose or crosslinked carboxymethyl cellulose), sodium starch glycolate, crosslinked polyvinylpyrrolidone polymers, and the like. Other disintegrants and superdisintegrants will be known to those skilled in the art.

A "binder" is a pharmaceutically acceptable excipient that holds one or more other compounds or active ingredients together. Binders provide tablets, granules, beads, or capsules with mechanical strength. Exemplary binders include hydroxyalkyl celluloses, alkyl celluloses, corn starch, gelatin, polyethylene glycol, polyethylene oxide, polyvinylpyrrolidone, and the like. Other binders will be known to those skilled in the art.

A "lubricant" is a pharmaceutically acceptable excipient that prevents other compounds or active ingredients from aggregation and/or prevents compounds or active ingredients from sticking to devices or equipment during the manufacturing process. Exemplary lubricants include magnesium stearate, calcium stearate, sodium stearate stearic acid, talcum, sodium stearyl fumarate, boric acid, sodium benzoate, sodium oleate, sodium acetate, sodium lauryl sulfate, magnesium lauryl sulfate, glyceryl behenate, and the like. Other lubricants will be known to those skilled in the art.

A "glidant" is a pharmaceutically acceptable excipient that is used to improve flowability of a compound or composition. Exemplary glidants include calcium phosphate, cellulose, colloidal silicon dioxide, hydrophobic colloidal silica, magnesium oxide, magnesium silicate, magnesium trisilicate, silicon dioxide, talc, and the like.

"Polyol" is an organic alcohol having two or more hydroxyl groups. In aspects, the polyol is a monomeric polyol. Exemplary polyols include mannitol, sorbitol, isomaltose, maltitol, lactose, sucrose, amylose, glucose, dextrose, lactitol, erythritol, arabitol, xylitol, trehalose, ribitol, inositol, and the like.

"Mannitol" refers to the compound HO—CH$_2$—(CH(OH))$_4$—CH$_2$—OH. In aspects, the mannitol is D-mannitol. Mannitol is commercially available, e.g., as PEARLITOL® from Roquette Freres Corporation, France.

"Cellulose" or "cellulose compound" or "cellulose polymer" refers to an organic polysaccharide compound comprising a chain of β(1→4) linked D-glucose units having the formula (C$_6$H$_{10}$O$_5$)$_n$.

"Microcrystalline cellulose" refers to a refined wood pulp that meets USP standards. Microcrystalline cellulose can be natural or synthetic, and is commercially available from numerous suppliers, such as Sigma-Aldrich, Miles Scientific, JRS Pharma, and FMC.

"Hydroxyalkyl cellulose" refers to an ether derivative of a cellulose compound having a hydroxyalkyl group. Examples of hydroxyalkyl cellulose include hydroxypropyl cellulose, hydroxyethyl cellulose, hydroxyethylmethyl cellulose, ethyl hydroxyethyl cellulose, hydroxypropylmethyl cellulose, and the like.

"Alkyl cellulose" refers to an ether derivative of a cellulose compound having an alkyl group. Examples of alkyl cellulose include methyl cellulose, ethyl cellulose, ethylmethyl cellulose, and the like.

"Carboxyalkyl cellulose" refers to an ether derivative of a cellulose compound having a carboxyl alkyl group. Examples of carboxyalkyl cellulose include carboxymethyl cellulose, crosslinked carboxymethyl cellulose, and the like.

"HPC" refers to hydroxypropyl cellulose. HPC is an ether of cellulose in which some of the hydroxyl groups in the repeating glucose units are hydroxypropylated using propylene oxide. HPC is an exemplary pharmaceutically acceptable polymer.

"HPMC" refers to hydroxypropyl methylcellulose or hypromellose. HPMC is a propylene glycol ether of methyl cellulose, hydroxypropyl and methyl combined with an anhydrous glucose ring by an ether bond. The percentage of each component (e.g., methoxyl groups, hydroxypropyl groups) and molecular weights can vary.

"Pharmaceutically acceptable polymer" refers to any polymer known in the art that can be used as a pharmaceutically acceptable excipient. Exemplary pharmaceutically acceptable polymers include polyvinylpyrrolide polymers, polyvinylpyrrolide copolymers, cellulose compounds, poly (lactide), poly(glycolide), poly(lactide-co-glycolide) copolymers, poloxamers, polysorbates (e.g., polysorbate 80, polysorbate 20), enteric coating materials, polyethylene oxide, pullulan, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl copolymers, starch, gelatin, polydioxanes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and the like.

"PVP" refers to polyvinylpyrrolidone or a polymer of vinylpyrrolidone. PVP is a class of polymers that can have an average molecular weight from about 1,000 Daltons to about 1,500,000 Daltons. In aspects, the PVP can be a crosslinked PVP. In aspects, the polyvinylpyrrolidone polymer has an average molecular weight from about 1,000 Daltons to about 1,000,000 Daltons; or from about 1,000 Daltons to about 500,000 Daltons; or from about 1,000 Daltons to about 200,000. In aspects, the polyvinylpyrrolidone polymer has an average molecular weight from about 1,000 Daltons to about 150,000 Daltons. In aspects, the polyvinylpyrrolidone polymer has an average molecular weight from about 10,000 Daltons to about 150,000 Daltons. In aspects, the polyvinylpyrrolidone polymer has an average molecular weight from about 50,000 Daltons to about 150,000 Daltons. In aspects, the polyvinylpyrrolidone polymer has an average molecular weight from about 60,000 Daltons to about 120,000 Daltons. PVP is commercially available from numerous sources, such as Sigma Aldrich, BASF, and Ashland.

"Polyvinylpyrrolidone copolymer" or "copolymer of vinylpyrrolidone" refers to copolymers comprising vinylpyrrolidone and one or more other monomers, such as acrylic monomers, styrene, vinyl acetate, and the like. Polyvinylpyrrolidone vinyl acetate copolymer and PVP-VA are exemplary polyvinylpyrrolidone copolymers. In aspects, the polyvinylpyrrolidone copolymer has an average molecular weight from about 1,000 Daltons to about 1,000,000 Daltons; or from about 1,000 Daltons to about 500,000 Daltons; or from about 1,000 Daltons to about 200,000. In aspects, the polyvinylpyrrolidone copolymer has an average molecular weight from about 1,000 Daltons to about 150,000 Daltons. In aspects, the polyvinylpyrrolidone copolymer has an average molecular weight from about 10,000 Daltons to about 150,000 Daltons. In aspects, the polyvinylpyrrolidone copolymer has an average molecular weight from about 50,000 Daltons to about 150,000 Daltons.

"Polyvinylpyrrolidone vinyl acetate copolymer" or "copolymer of polyvinylpyrrolidone and vinyl acetate" or "copolymer of vinylpyrrolidone and vinyl acetate" all refer to a class of copolymers of vinylpyrrolidone and vinyl acetate that having varying wt % ratios of vinylpyrrolidone to vinyl acetate, such as from about 30:70 to about 70:30, including 30:70, 35:65, 50:50, 60:40, and 70:30. The wt % ratios of vinylpyrrolidone to vinyl acetate can determine different properties of the copolymer, including the glass transition temperature. Polyvinylpyrrolidone vinyl acetate copolymer is commercially available from numerous sources, such as BASF and Ashland.

"Copovidone" refers to a copolymer of 1-vinyl-2-pyrrolidone and vinyl acetate at the weight ratio of 1-vinyl-2-pyrrolidone to vinyl acetate of about 3:2. "Copovidone" is commercially available as KOLLIDON® VA64 from BASF Corporation, Florham Park, N.J.

"Polyethylene oxide" or "polyoxyethylene" or "polyethylene glycol" or "PEO" refers to a polyether compound having the chemical structure H—(OCH$_2$CH$_2$)$_n$—OH. A polyethylene oxide may have an average molecular weight from 100 Daltons to about 10,000,000 Daltons. In aspects, the polyethylene oxide has an average molecular weight from about 1,000 Daltons to about 2,000,000 Daltons. In aspects of the compositions, granules, and beads described herein, two or more polyethylene oxide compounds having different average molecular weights may be used. Polyethylene oxide is commercially available from, e.g., Dow Chemical.

"Surfactant" refers to a wetting agent that lowers the surface or interfacial tension between two liquids. A surfactant can be anionic, cationic, nonionic, or zwitterionic.

"Anionic surfactant" refers to a surfactant that has a negatively charged head group moiety, such as a carboxylate group, a sulfate group, a sulfonate group, a phosphate ester group, or a combination of two or more thereof. In aspects, anionic surfactants include alkyl sulfates, acyl sulfates, salts of bile acids, and fatty acids. In aspects, the anionic surfactants include sodium lauryl sulfate, ammonium lauryl sulfate, sodium laureth sulfate, sodium myreth sulfate, sodium stearate, dioctyl sodium sulfosuccinate, and the like. In aspects, the anionic surfactants include cholic acid, deoxycholic acid, glycocholic acid, taurocholic acid, glycodeoxycholic acid, taurodeoxycholic acid, ursocholic acid, ursodeoxycholic acid, chenodeoxycholic acid, glycochenodeoxycholic acid, taurochenodeoxycholic acid, oleic acid, and the like. In aspects, anionic surfactants include aliphatic sulfonates, primary alkane (e.g., $C_5$-$C_{25}$) sulfonates, primary alkane (e.g., $C_5$-$C_{25}$) disulfonates, ($C_5$-$C_{25}$)alkene sulfonates, $C_5$-$C_{25}$ hydroxyalkane sulfonates, alkyl glyceryl ether sulfonates, aromatic sulfonates (e.g., alkyl benzene sulfonates), sodium $C_{10}$-$C_{20}$ olefin sulfonates (e.g., sodium $C_{14}$-$C_{16}$ olefin sulfonate), phosphonic acids (e.g., octylphosphonic acid, laurylphosphonic acid, salts of octylphosphonic acid, salts of laurylphosphonic acid), and the like.

"Cationic surfactant" refers to a surfactant that has a positively charged head group moiety. Exemplary cationic surfactants include cetyl pyridinium chloride and cetyl trimethylammonium bromide.

"Nonionic surfactant" refers to a surfactant that has covalently bonded oxygen-containing hydrophilic groups. Exemplary nonionic surfactants include long chain alcohols; fatty acid esters (e.g., monolaurates, monooleates, monopalmitates, monostearates); sorbitans (e.g., polyoxyethylene (20) sorbitan monooleate, monostearate, monolaurate); ethoxylated fatty acids (e.g., polyoxythelene (40) stearate, ethoxylated lauric acid); ethoxylated alcohols (e.g., polyoxyethylene lauryl ether); ethoxylated alkyl phenols (e.g., nonylphenoxypoly(ethyleneoxy)ethanol); and polyglycolized glycerides.

"Zwitterionic surfactant" refers to a surfactant that has both a cationic moiety and an anionic moiety. Generally, a zwitterionic surfactant has a cationic portion based on a primary amine, a secondary amine, a tertiary amine, or a quaternary ammonium cation. The anionic portion may comprise a phosphate anion with an amine or ammonium, such as phosphatidylserine, phosphatidylethanolamine, phosphatidylcholine, sphingomyelins, and the like.

"Capsule" refers to a shell encapsulating a composition. The shell can be a hard shell or a soft shell, and generally comprise gelatin, a polymer (such as a hydroxyalkyl cellulose, an alkyl cellulose, a carboxyalkyl cellulose, or a combination of two or more thereof), or a combination thereof. In aspects, the capsule shell comprises a hydroxyalkyl cellulose. In aspects, the capsule shell comprises hydroxypropylmethyl cellulose. In aspects, the capsule shell comprises an enteric polymer.

"Outer layer" refers to a layer completely surrounding a composition, tablet, capsule, bead, or granule. In aspects, the outer layer is a polymer, such as a hydroxyalkyl cellulose, an alkyl cellulose, a carboxyalkyl cellulose, a polyvinyl alcohol, or a combination of two or more thereof. In aspects, the outer layer is a protective coating or an aesthetic coating. In aspects, the outer layer is an enteric coating. In aspects, the outer layer is a protective coating, an aesthetic coating, an enteric coating, or a combination of two or more thereof.

"Enteric coating" refers to a coating containing one or more materials that dissolve or disintegrate in the small intestine, but not in the stomach or gastric environment. Exemplary enteric coating materials include enteric polymers.

"Enteric polymer" refers to a polymer that will dissolve or disintegrate at a pH from about 5 to about 7.4, but that will not dissolve or disintegrate at a pH from about 1 to about 4.5. Exemplary enteric polymers include polymerized gelatin, shellac, methacrylic acid copolymers, cellulose butyrate phthalate, cellulose hydrogen phthalate, cellulose propionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, and acrylic acid polymers and copolymers, typically formed from methyl acrylate, ethyl acrylate, methyl methacrylate and/or ethyl methacrylate with copolymers of acrylic and methacrylic acid esters (e.g., EUDRAGIT® NE, EUDRAGIT® RL, EUDRAGIT® RS by Evonik Roehm GMBH).

"Inert core" refers to a pharmacologically inactive particle of any shape. The inert core can be soluble, insoluble, or a combination thereof. In aspects an inert core is spherical. In aspects, an inert core comprises sugar, microcrystalline cellulose, carnauba wax, mannitol, or a combination of two or more thereof. An inert core has a size greater than 25 microns; or from about 50 microns to about 3 mm; or from about 1 mm to about 2.5 mm. Inert cores are commercially available, e.g., Pharmatrans Sanaq AG, Switzerland. When used in reference to a bead, an "inert core" is surrounded by a "drug layer," which is a layer of any thickness comprising the adenosine A2A receptor antagonists described herein and a pharmaceutically acceptable excipient. The drug layer can be a single layer or multiple layers.

"Therapeutically effective amount" or "effective amount" refers to an amount sufficient to treat or prevent a disease or symptom (e.g. achieve the effect for which it is administered, treat a disease, reduce enzyme activity, increase enzyme activity, reduce protein function, reduce one or more symptoms of a disease or condition). In aspects, a therapeutically effective amount is an amount sufficient to treat cancer. The exact amounts will depend on the purpose of the treatment, whether the adenosine A2A receptor antagonists are being used as a sole therapeutic agent to treat cancer or whether they are being used in combination with other chemotherapeutic or immunomodulatory compounds. The dose of the adenosine A2A receptor antagonist can be different if it is being used as a sole therapeutic agent or if it is being used in combination therapy, and the skilled artisan will appreciate that the amount of adenosine A2A receptor antagonist may be adjusted higher or lower depending on the patient, other chemotherapeutic or immunomodulatory compounds being used, and the type of cancer being treated.

"Patient" or "subject" refers to a mammal suffering from or prone to a disease (e.g., cancer) that can be treated by administration of a compound or pharmaceutical composition or by a method, as provided herein. Non-limiting examples of a patient include humans, bovines, rats, mice, dogs, cats, monkeys, goat, sheep, and the like. In aspects, a patient is human. In aspects, a patient is a dog or a cat. In aspects, the patient is a human adult. In aspects, the patient is a human child.

A "month refers" to a period of time from about 28 days to about 31 days. In aspects, one month is 28 days. In aspects, one month is 29 days. In aspects, one month is 30 days. In aspects, one month is 31 days.

The term "rapidly-disintegrating" refers to a pharmaceutical composition described herein (e.g., oral formulation, granule, bead, tablet, capsule) that can disintegrate within a short period of time. Disintegration is measured by US Pharmacopoeia (USP), Chapter <701>, Disintegration Test. Briefly, the composition is placed in a basket-rack assembly, in 1000 mL deionized water, at about 37° C., at 30 cycles/minute. In aspects, the short period of time is about 30 minutes or less.

The term "rapidly-dissolving" refers to a pharmaceutical composition described herein (e.g., oral formulation, granule, bead, tablet, capsule) which provides for the dissolution of the adenosine A2A receptor antagonist from the pharmaceutical composition within a short period of time. Dissolution is measured by US Pharmacopoeia (USP), Chapter <711>, Dissolution Test. Briefly, the composition is placed in a USP Apparatus 2 at a paddle speed of 50 rpm, in a dissolution medium of 0.1N HCl, 900 mL, at about 37° C., In aspects, a short period of time is dissolution of at least 50% of the composition in 60 minutes. In aspects, a short period of time is dissolution of at least 50% of the composition in 30 minutes. In aspects, a short period of time is dissolution of at least 50% of the composition in 10 minutes.

"Total impurities" refers to in the common pharmaceutical nomenclature as the total sum of all measured impurities and degradation products from the drug substance and is also referred to as total related substances. The total impurities are obtained from a stability-indicating HPLC method by integration of all peaks other than solvent or peaks related to the excipients. Gradient method was used with 0.1% (V/V) methanesulfonic acid in water as the first mobile phase and acetonitrile as the second. A $C_{18}$ column with UV detection at 225 nm was used. An acetonitrile-water mixture was used for dilution of the samples.

The term "bioequivalent" or "bioequivalent formulation" or "bioequivalent product" is a formulation that is pharmaceutically equivalent to its reference listed drug (e.g., Pharmaceutical Composition No. 5; Pharmaceutical Composition No. 6), i.e., has the same active ingredient, dosage form, strength, and route of administration under the same conditions of use. A bioequivalent formulation shows no significant difference in the rate and extent of absorption of the active pharmaceutical ingredient; and, such that it is therapeutically equivalent, i.e., substitutable for the reference listed drug with the expectation that the bioequivalent product will have the same safety and efficacy as its reference listed drug (e.g., Pharmaceutical Composition No. 5; Pharmaceutical Composition No. 6).

The terms "disease" or "condition" refer to a state of being or health status of a patient or subject capable of being treated with a compound, pharmaceutical composition, or method provided herein. In aspects, the disease is cancer, such as lung cancer (e.g., non-small cell lung cancer), melanoma (e.g., malignant melanoma), renal cell cancer, breast cancer (e.g., triple negative breast cancer), colorectal cancer (e.g., microsatellite instable colorectal cancer), bladder cancer, prostate cancer (e.g., metastatic castration resistant prostate cancer, castration resistant prostate cancer), or a head and neck cancer. In aspects, the disease is a metastatic cancer.

"QD" refers to administration of the compounds and compositions described herein once daily.

"BID" refers to administration of the compounds and compositions described herein twice daily (BID). In aspects, twice daily administration is after the patient wakes up and before the patient goes to bed. In aspects, twice daily administration is about every 8 hours to about every 16 hours. In aspects, twice daily administration is about every 9 hours to about every 15 hours. In aspects, twice daily administration is about every 10 hours to about every 14 hours. In aspects, twice daily administration is about every 11 hours to about every 13 hours. In aspects, twice daily administration is about every 12 hours.

"Cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

As used herein, the terms "metastasis," "metastatic," "metastatic tumor," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor.

"Adenosine A2A receptor" or "A2A receptor" refer to and include any of the recombinant or naturally-occurring forms of the adenosine A2A receptor also known as ADORA2A or isoforms or variants or homologs thereof that maintain adenosine A2A receptor activity (e.g., within at least 50%, 80%, 90%, 95%, 96%, 97%, 98%, 99% or 100% activity compared to adenosine A2A receptor). In some aspects, the isoforms, variants, or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring adenosine A2A receptor. In aspects, the adenosine A2A receptor is substantially identical to the protein identified by the UniProt reference number P29274 or an isoform, variant, or homolog having substantial identity thereto. In aspects, the adenosine A2A receptor is substantially identical to the protein identified by the UniProt reference number Q60613 or an isoform, variant or homolog having substantial identity thereto.

"Adenosine A2A receptor antagonist" is a compound that inhibits an adenosine A2A receptor, e.g., by binding, partially or totally blocking, decreasing, preventing, delaying, inactivating, desensitizing, or down-regulating adenosine A2A receptor activity. "Inhibition," "inhibit," "inhibiting" and the like in reference to an adenosine A2A receptor interaction means negatively affecting (e.g., decreasing) the activity or function of the protein (e.g., decreasing the activity of an A2A receptor) relative to the activity or function of the protein in the absence of the inhibitor (e.g., an A2A receptor antagonist). In aspects, inhibition refers to reduction of a disease or symptoms of disease (e.g., cancer). Thus, inhibition includes, at least in part, partially or totally blocking stimulation, decreasing, preventing, or delaying activation, or inactivating, desensitizing, or down-regulating signal transduction or enzymatic activity of an adenosine A2A receptor. In aspects, the adenosine A2A receptor antagonist is a pharmaceutically acceptable salt of an adenosine A2A receptor antagonist.

In embodiments, the adenosine A2A receptor antagonist is a compound of Formula (I) or a pharmaceutically acceptable salt thereof:

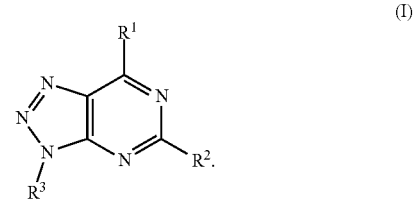

In Formula (I): $R^1$ is independently hydrogen, halogen, $-CX^a{}_3$, $-CN$, $-SO_2Cl$, $-SO_{n1}R^9$, $-SO_{v1}NR^9R^{10}$, $-NHNH_2$, $-ONR^9R^{10}$, $-NHC=(O)NHNH_2$, $-NHC=(O)NR^9R^{10}$, $-N(O)_{m1}$, $-NR^9R^{10}$, $-NH-O-R^9$, $-C(O)R^9$, $-C(O)-OR^9$, $-C(O)NR^9R^{10}$, $-OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or
substituted or unsubstituted heteroaryl.

In Formula (I): $R^2$ is independently hydrogen, halogen, $-CX^b{}_3$, $-CN$, $-SO_2Cl$, $-SO_{n1}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, $-OR^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In Formula (I): $R^3$ is independently hydrogen, halogen, $-CX^c{}_3$, $-CN$, $-SO_2Cl$, $-SO_{n1}R^{13}$, $-SO_{v3}NR^{13}R^{14}$, $-NHNH_2$, $-ONR^{13}R^{14}$, $-NHC=(O)NHNH_2$, $-NHC=(O)NR^{13}R^{14}$, $-N(O)_{m3}$, $-NR^{13}R^{14}$, $-NH-O-R^{13}$, $-C(O)R^{13}$, $-C(O)-OR^{13}$, $-C(O)NR^{13}R^{14}$, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In Formula (I): $R^9$, $R^{10}$, $R^{11}$, $R^{12}$, $R^{13}$ and $R^{14}$ are independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In aspects, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In Formula (I): $X^a$, $X^b$ and $X^c$ are independently $-F$, $-Cl$, $-Br$, or $-I$.

In Formula (I): The symbols $n_1$, $n_2$ and $n_3$ are independently an integer from 0 to 4. In aspects, $n_1$ is 0. In aspects, $n_1$ is 1. In aspects, $n_1$ is 3. In aspects, $n_1$ is 4. In aspects, $n_2$ is 0. In aspects, $n_2$ is 1. In aspects, $n_2$ is 3. In aspects, $n_2$ is 4. In aspects, $n_3$ is 0. In aspects, $n_3$ is 1. In aspects, $n_3$ is 3. In aspects, $n_3$ is 4.

In Formula (I): The symbols $m_1$, $m_2$ and $m_3$ are independently an integer from 1 to 2. In aspects, $m_1$ is 0. In aspects, $m_1$ is 1. In aspects, $m_1$ is 2. In aspects, $m_2$ is 0. In aspects, $m_2$ is 1. In aspects, $m_2$ is 2. In aspects, $m_3$ is 0. In aspects, $m_3$ is 1. In aspects, $m_2$ is 2.

In Formula (I): The symbols $v_1$, $v_2$ and $v_3$ are independently an integer from 1 to 2. In aspects, $v_1$ is 0. In aspects, $v_1$ is 1. In aspects, $v_1$ is 2. In aspects, $v_2$ is 0. In aspects, $v_2$ is 1. In aspects, $v_2$ is 2. In aspects, $v_3$ is 0. In aspects, $v_3$ is 1. In aspects, $v_3$ is 2.

In embodiments, $R^1$ is independently hydrogen, halogen, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, $R^{1A}$-substituted or unsubstituted alkyl, $R^{1A}$-substituted or unsubstituted heteroalkyl, $R^{1A}$-substituted or unsubstituted cycloalkyl, $R^{1A}$-substituted or unsubstituted heterocycloalkyl, $R^{1A}$-substituted or unsubstituted aryl, or $R^{1A}$-substituted or unsubstituted heteroaryl. $R^1$ may be $R^{1A}$-substituted or unsubstituted (e.g., $C_1$-$C_{20}$ or $C_1$-$C_6$) alkyl, $R^{1A}$-substituted or unsubstituted (e.g., 2 to 20 membered or 2 to 6 membered) heteroalkyl, $R^{1A}$-substituted or unsubstituted (e.g., $C_3$-$C_8$ or $C_5$-$C_7$)cycloalkyl, $R^{1A}$-substituted or unsubstituted (e.g., 3 to 8 membered or 3 to 6 membered) heterocycloalkyl, $R^{1A}$-substituted or unsubstituted (e.g., $C_5$-$C_{10}$ or $C_5$-$C_6$) aryl, or $R^{1A}$-substituted or unsubstituted (e.g., 5 to 10 membered or 5 to 6 membered) heteroaryl.

In embodiments, $R^{1A}$ is independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, $R^{1B}$-substituted or unsubstituted alkyl, $R^{1B}$-substituted or unsubstituted heteroalkyl, $R^{1B}$-substituted or unsubstituted cycloalkyl, $R^{1B}$-substituted or unsubstituted heterocycloalkyl, $R^{1B}$-substituted or unsubstituted aryl, or $R^{1B}$-substituted or unsubstituted heteroaryl. $R^{1A}$ may be $R^{1B}$-substituted or unsubstituted (e.g., $C_1$-$C_{20}$ or $C_1$-$C_6$)alkyl, $R^{1B}$-substituted or unsubstituted (e.g., 2 to 20 membered or 2 to 6 membered) heteroalkyl, $R^{1B}$-substituted or unsubstituted (e.g., $C_3$-$C_8$ or $C_5$-$C_7$) cycloalkyl, $R^{1B}$-substituted or unsubstituted (e.g., 3 to 8 membered or 3 to 6 membered) heterocycloalkyl, $R^{1B}$-substituted or unsubstituted (e.g., $C_5$-$C_{10}$ or $C_5$-$C_6$) aryl, or $R^{1B}$-substituted or unsubstituted (e.g., 5 to 10 membered or 5 to 6 membered) heteroaryl.

In embodiments, $R^{1B}$ is independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, $R^{1C}$-substituted or unsubstituted alkyl, $R^{1C}$-substituted or unsubstituted heteroalkyl, $R^{1C}$-substituted or unsubstituted cycloalkyl, $R^{1C}$-substituted or unsubstituted heterocycloalkyl, $R^{1C}$-substituted or unsubstituted aryl, or $R^{1C}$-substituted or unsubstituted heteroaryl. $R^{1B}$ may be $R^{1C}$-substituted or unsubstituted (e.g., $C_1$-$C_{20}$ or $C_1$-$C_6$) alkyl, $R^{1C}$-substituted or unsubstituted (e.g., 2 to 20 membered or 2 to 6 membered) heteroalkyl, $R^{1C}$-substituted or unsubstituted (e.g., $C_3$-$C_8$ or $C_5$-$C_7$) cycloalkyl, $R^{1C}$-substituted or unsubstituted (e.g., 3 to 8 membered or 3 to 6 membered) heterocycloalkyl, $R^{1C}$-substituted or unsubstituted (e.g., $C_5$-$C_{10}$ or $C_5$-$C_6$) aryl, or $R^{1C}$-substituted or unsubstituted (e.g., 5 to 10 membered or 5 to 6 membered) heteroaryl.

In embodiments, $R^{1C}$ is independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, unsubstituted alkyl, unsubstituted heteroalkyl, unsubstituted cycloalkyl, unsubstituted heterocycloalkyl, unsubstituted aryl, or unsubstituted heteroaryl. $R^{1C}$ may be independently unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, $R^1$ is independently $R^{1A}$-substituted or unsubstituted alkyl, $R^{1A}$-substituted or unsubstituted heteroalkyl, $R^{1A}$-substituted or unsubstituted cycloalkyl, $R^{1A}$-substituted or unsubstituted heterocycloalkyl, $R^{1A}$-substituted or unsubstituted aryl, or s $R^{1A}$-substituted or unsubstituted heteroaryl. In aspects, $R^1$ is $R^{1A}$-substituted or unsubstituted (e.g., 5 to 10 membered or 5 to 6 membered) heteroaryl. In aspects, $R^1$ is unsubstituted 5 to 6 membered heteroaryl. In aspects, $R^1$ is $R^{1A}$-substituted 5 to 6 membered heteroaryl. In aspects, $R^1$ is unsubstituted 5 membered heteroaryl. In aspects, $R^1$ is $R^{1A}$-substituted 5 membered heteroaryl. In aspects, $R^1$ is $R^{1A}$-substituted furanyl.

In embodiments, $R^{1A}$ is $R^{1B}$-substituted or unsubstituted (e.g., $C_1$-$C_{20}$ or $C_1$-$C_6$) alkyl. In aspects, $R^{1A}$ is $R^{1B}$-substituted $C_1$-$C_6$ alkyl. In aspects, $R^{1A}$ is unsubstituted $C_1$-$C_6$ alkyl. In aspects, $R^{1A}$ is $R^{1B}$-substituted $C_1$-$C_4$ alkyl. In aspects, $R^{1A}$ is unsubstituted $C_1$-$C_4$ alkyl. In aspects, $R^{1A}$ is $R^{1B}$-substituted $C_1$-$C_3$ alkyl. In aspects, $R^{1A}$ is unsubstituted $C_1$-$C_3$ alkyl. In aspects, $R^{1A}$ is methyl.

In embodiments, $R^2$ is independently hydrogen, halogen, $-CX^b_3$, $-CN$, $-SO_2Cl$, $-SO_{n2}R^{11}$, $-SO_{v2}NR^{11}R^{12}$, $-NHNH_2$, $-ONR^{11}R^{12}$, $-NHC=(O)NHNH_2$, $-NHC=(O)NR^{11}R^{12}$, $-N(O)_{m2}$, $-NR^{11}R^{12}$, $-NH-O-R^{11}$, $-C(O)R^{11}$, $-C(O)-OR^{11}$, $-C(O)NR^{11}R^{12}$, or $-OR^{11}$. In aspects of the methods provided herein, $R^2$ is independently hydrogen, halogen, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, unsubstituted alkyl, unsubstituted heteroalkyl, unsubstituted cycloalkyl, unsubstituted heterocycloalkyl, unsubstituted aryl, or unsubstituted heteroaryl. In aspects, $R^2$ is $-NR^{11}R^{12}$. In aspects, $R^{11}$ and $R^{12}$ are independently hydrogen or substituted or unsubstituted (e.g., $C_1$-$C_{20}$ or $C_1$-$C_6$) alkyl. In aspects, $R^{11}$ and $R^{12}$ are independently substituted or unsubstituted $C_1$-$C_6$ alkyl. In aspects, $R^{11}$ and $R^{12}$ are independently substituted or unsubstituted $C_1$-$C_4$ alkyl. In aspects, $R^{11}$ and $R^{12}$ are independently substituted or unsubstituted $C_1$-$C_3$ alkyl. In aspects, $R^{11}$ and $R^{12}$ are independently unsubstituted $C_1$-$C_6$ alkyl. In aspects, $R^{11}$ and $R^{12}$ are independently substituted or unsubstituted $C_1$-$C_4$ alkyl. In aspects, $R^{11}$ and $R^{12}$ are independently unsubstituted $C_1$-$C_3$ alkyl. In aspects, $R^{11}$ and $R^{12}$ are independently hydrogen.

In embodiments, $R^3$ is independently hydrogen, halogen, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, $R^4$-substituted or unsubstituted alkyl, $R^4$-substituted or unsubstituted heteroalkyl, $R^4$-substituted or unsubstituted cycloalkyl, $R^4$-substituted or unsubstituted heterocycloalkyl, $R^4$-substituted or unsubstituted aryl, or $R^4$-substituted or unsubstituted heteroaryl. $R^3$ may be $R^4$-substituted or unsubstituted (e.g., $C_1$-$C_{20}$ or $C_1$-$C_6$) alkyl, $R^4$-substituted or unsubstituted (e.g., 2 to 20 membered or 2 to 6 membered) heteroalkyl, $R^4$-substituted or unsubstituted (e.g., $C_3$-$C_8$ or $C_5$-$C_7$) cycloalkyl, $R^4$-substituted or unsubstituted (e.g., 3 to 8 membered or 3 to 6 membered) heterocycloalkyl, $R^4$-substituted or unsubstituted (e.g., $C_5$-$C_{10}$ or $C_5$-$C_6$) aryl, or $R^4$-substituted or unsubstituted (e.g., 5 to 10 membered or 5 to 6 membered) heteroaryl.

In embodiments, $R^4$ is independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, $R^5$-substituted or unsubstituted alkyl, $R^5$-substituted or unsubstituted heteroalkyl, $R^5$-substituted or unsubstituted cycloalkyl, $R^5$-substituted or unsubstituted heterocycloalkyl, $R^5$-substituted or unsubstituted aryl, or $R^5$-substituted or unsubstituted heteroaryl. $R^4$ may be $R^5$-substituted or unsubstituted (e.g., $C_1$-$C_{20}$ or $C_1$-$C_6$) alkyl, $R^5$-substituted or unsubstituted (e.g., 2 to 20 membered or 2 to 6 membered) heteroalkyl, $R^5$-substituted or unsubstituted (e.g., $C_3$-$C_8$ or $C_5$-$C_7$) cycloalkyl, $R^5$-substituted or unsubstituted (e.g., 3 to 8 membered or 3 to 6 membered) heterocycloalkyl, $R^5$-substituted or unsubstituted (e.g., $C_5$-$C_{10}$ or $C_5$-$C_6$) aryl, or $R^5$-substituted or unsubstituted (e.g., 5 to 10 membered or 5 to 6 membered) heteroaryl.

In embodiments, $R^5$ is independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, $R^6$-substituted or unsubstituted alkyl, $R^6$-substituted or unsubstituted heteroalkyl, $R^6$-substituted or unsubstituted cycloalkyl, $R^6$-substituted or unsubstituted heterocycloalkyl, $R^6$-substituted or unsubstituted aryl, or $R^6$-substituted or unsubstituted heteroaryl. $R^5$ may be $R^6$-substituted or unsubstituted (e.g., $C_1$-$C_{20}$ or $C_1$-$C_6$) alkyl, $R^6$-substituted or unsubstituted (e.g., 2 to 20 membered or 2 to 6 membered) heteroalkyl, $R^6$-substituted or unsubstituted (e.g., $C_3$-$C_8$ or $C_5$-$C_7$) cycloalkyl, $R^6$-substituted or unsubstituted (e.g., 3 to 8 membered or 3 to 6 membered) heterocycloalkyl, $R^6$-substituted or unsubstituted (e.g., $C_5$-$C_{10}$ or $C_5$-$C_6$) aryl, or $R^6$-substituted or unsubstituted (e.g., 5 to 10 membered or 5 to 6 membered) heteroaryl.

In embodiments, $R^6$ is independently hydrogen, halogen, $=O$, $=S$, $-CF_3$, $-CN$, $-CCl_3$, $-COOH$, $-CH_2COOH$, $-CONH_2$, $-OH$, $-SH$, $-SO_2Cl$, $-SO_3H$, $-SO_4H$, $-SO_2NH_2$, $-NO_2$, $-NH_2$, $-NHNH_2$, $-ONH_2$, $-NHC=(O)NHNH_2$, $R^7$-substituted or unsubstituted alkyl, $R^7$-substituted or unsubstituted heteroalkyl, $R^7$-substituted or unsubstituted cycloalkyl, $R^7$-substituted or unsubstituted heterocycloalkyl, $R^7$-substituted or unsubstituted aryl, or $R^7$-substituted or unsubstituted heteroaryl. $R^6$ may be $R^7$-substituted or unsubstituted (e.g., $C_1$-$C_{20}$ or $C_1$-$C_6$) alkyl, $R^7$-substituted or unsubstituted (e.g., 2 to 20 membered or 2 to 6 membered) heteroalkyl, $R^7$-substituted or unsubstituted (e.g., $C_3$-$C_8$ or $C_5$-$C_7$) cycloalkyl, $R^7$-substituted or unsubstituted (e.g., 3 to 8 membered or 3 to 6 membered) heterocycloalkyl, $R^7$-substituted or unsubstituted (e.g., $C_5$-$C_{10}$ or $C_5$-$C_6$) aryl, or $R^7$-substituted or unsubstituted (e.g., 5 to 10 membered or 5 to 6 membered) heteroaryl.

In embodiments, $R^3$ is independently hydrogen, halogen, $R^4$-substituted or unsubstituted alkyl, $R^4$-substituted or unsubstituted heteroalkyl, $R^4$-substituted or unsubstituted cycloalkyl, $R^4$-substituted or unsubstituted heterocycloalkyl, $R^4$-substituted or unsubstituted aryl, or $R^4$-substituted or unsubstituted heteroaryl. In aspects, $R^3$ is independently $R^4$-substituted or unsubstituted (e.g., $C_1$-$C_{20}$ or $C_1$-$C_6$) alkyl. In aspects, $R^3$ is independently $R^4$-substituted or unsubstituted $C_1$-$C_6$ alkyl. In aspects, $R^3$ is independently $R^4$-substituted or unsubstituted $C_1$-$C_5$ alkyl. In aspects, $R^3$ is independently $R^4$-substituted or unsubstituted $C_1$-$C_4$ alkyl. In aspects, $R^3$ is independently $R^4$-substituted or unsubstituted $C_1$-$C_3$ alkyl. In aspects, $R^3$ is independently unsubstituted $C_1$-$C_6$ alkyl. In aspects, $R^3$ is independently unsubstituted $C_1$-$C_5$ alkyl. In aspects, $R^3$ is independently $R^4$-unsubstituted $C_1$-$C_4$ alkyl. In aspects, $R^3$ is independently unsubstituted $C_1$-$C_3$ alkyl. In aspects, $R^3$ is independently $R^4$-substituted $C_1$-$C_6$ alkyl. In aspects, $R^3$ is independently $R^4$-substituted $C_1$-$C_5$ alkyl. In aspects, $R^3$ is independently $R^4$-substituted $C_1$-$C_4$ alkyl. In aspects, $R^3$ is independently $R^4$-substituted $C_1$-$C_3$ alkyl. In aspects, $R^3$ is $R^4$-substituted $C_1$ alkyl.

In embodiments, $R^4$ is $R^5$-substituted or unsubstituted (e.g., $C_1$-$C_{20}$ or $C_1$-$C_6$) alkyl, $R^5$-substituted or unsubstituted (e.g., 2 to 20 membered or 2 to 6 membered) heteroalkyl, $R^5$-substituted or unsubstituted (e.g., $C_3$-$C_8$ or $C_5$-$C_7$) cycloalkyl, $R^5$-substituted or unsubstituted (e.g., 3 to 8 membered or 3 to 6 membered) heterocycloalkyl, $R^5$-substituted or unsubstituted (e.g., $C_5$-$C_{10}$ or $C_5$-$C_6$) aryl, or $R^5$-substituted or unsubstituted (e.g., 5 to 10 membered or 5 to 6 membered) heteroaryl. In aspects, $R^4$ is $R^5$-substituted or unsubstituted 5 to 6 membered heteroaryl. In aspects, $R^4$ is $R^5$-substituted or unsubstituted 6 membered heteroaryl. In aspects, $R^4$ is unsubstituted 6 membered heteroaryl. In aspects, $R^4$ is $R^5$-substituted 6 membered heteroaryl. In aspects, $R^4$ is $R^5$-substituted pyridinyl.

In embodiments, $R^5$ is $R^6$-substituted or unsubstituted (e.g., $C_1$-$C_{20}$ or $C_1$-$C_6$) alkyl, $R^6$-substituted or unsubstituted (e.g., 2 to 20 membered or 2 to 6 membered) heteroalkyl, $R^6$-substituted or unsubstituted (e.g., $C_3$-$C_8$ or $C_5$-$C_7$) cycloalkyl, $R^6$-substituted or unsubstituted (e.g., 3 to 8 membered or 3 to 6 membered) heterocycloalkyl, $R^6$-substituted or unsubstituted (e.g., $C_5$-$C_{10}$ or $C_5$-$C_6$) aryl, or $R^6$-substituted or unsubstituted (e.g., 5 to 10 membered or 5 to 6 membered) heteroaryl. In aspects, $R^5$ is $R^6$-substituted or unsubstituted 2 to 6 membered heteroalkyl. In aspects, $R^5$ is $R^6$-substituted or unsubstituted 2 to 5 membered heteroalkyl. In aspects, $R^5$ is $R^6$-substituted or unsubstituted 2 to 4 membered heteroalkyl. In aspects, $R^5$ is $R^6$-substituted or unsubstituted 2 to 3 membered heteroalkyl. In aspects, $R^5$ is $R^6$-substituted or unsubstituted 2 membered heteroalkyl. In aspects, $R^5$ is unsubstituted 2 to 6 membered heteroalkyl. In aspects, $R^5$ is unsubstituted 2 to 5 membered heteroalkyl. In aspects, $R^5$ is unsubstituted 2 to 4 membered heteroalkyl. In aspects, $R^5$ unsubstituted 2 to 3 membered heteroalkyl. In aspects, $R^5$ is unsubstituted 2 membered heteroalkyl. In aspects, $R^5$ is $R^6$-substituted 2 to 6 membered heteroalkyl. In aspects, $R^5$ is $R^6$-substituted 2 to 5 membered heteroalkyl. In aspects, $R^5$ is $R^6$-substituted 2 to 4 membered heteroalkyl. In aspects, $R^5$ is $R^6$-substituted 2 to 3 membered heteroalkyl. In aspects, $R^5$ is $R^6$-substituted 2 membered heteroalkyl.

In embodiments, $R^6$ is $R^7$-substituted or unsubstituted (e.g., $C_1$-$C_{20}$ or $C_1$-$C_6$) alkyl, $R^7$-substituted or unsubstituted (e.g., 2 to 20 membered or 2 to 6 membered) heteroalkyl, $R^7$-substituted or unsubstituted (e.g., $C_3$-$C_8$ or $C_5$-$C_7$) cycloalkyl, $R^7$-substituted or unsubstituted (e.g., 3 to 8 membered or 3 to 6 membered) heterocycloalkyl, $R^7$-substituted or unsubstituted (e.g., $C_5$-$C_{10}$ or $C_5$-$C_6$) aryl, or $R^7$-substituted or unsubstituted (e.g., 5 to 10 membered or 5 to 6 membered) heteroaryl. In aspects, $R^6$ is $R^7$-substituted or unsubstituted 3 to 6 membered heterocycloalkyl. In aspects, $R^6$ is $R^7$-substituted or unsubstituted 5 membered heterocycloalkyl. In aspects, $R^6$ is $R^7$-substituted 5 membered heterocycloalkyl. In aspects, $R^6$ is unsubstituted 5 membered heterocycloalkyl. In aspects, $R^6$ is unsubstituted tetrahydrofuranyl.

In embodiments, $R^9$, $R^{10}$, $R^{11}$, $R^{12}$, $R^{13}$ and $R^{14}$ are independently hydrogen, halogen, =O, =S, —$CF_3$, —CN, —$CCl_3$, —COOH, —$CH_2$COOH, —$CONH_2$, —OH, —SH, —$SO_2$Cl, —$SO_3$H, —$SO_4$H, —$SO_2NH_2$, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$ is $R^{14}$-substituted furanyl. In aspects, $R^{14}$ is methyl. In aspects, $R^2$ is —$NR^{11}R^{12}$. In aspects, $R^{11}$ and $R^{12}$ are independently hydrogen. In aspects, $R^3$ is $R^4$-substituted $C_1$ alkyl. In aspects, $R^4$ is $R^5$-substituted pyridinyl. In aspects, $R^5$ is $R^6$-substituted 2 membered heteroalkyl. In aspects, $R^6$ is unsubstituted tetrahydrofuranyl.

In embodiments, the adenosine A2A receptor antagonist is a compound of Formula (II) or a pharmaceutically acceptable salt thereof:

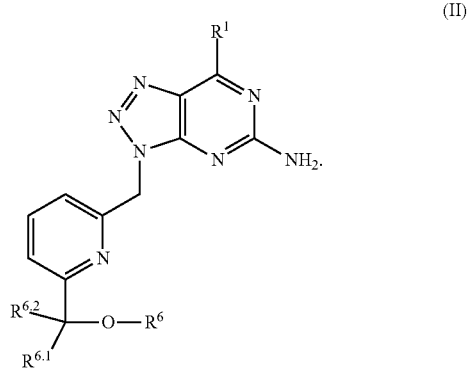

(II)

In Formula (II): $R^6$, $R^{6.1}$ and $R^{6.2}$ are independently hydrogen, halogen, —$CF_3$, —CN, —$CCl_3$, —COOH, —$CH_2$COOH, —$CONH_2$, —OH, —SH, —$SO_2$Cl, —$SO_3$H, —$SO_4$H, —$SO_2NH_2$, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In aspects, $R^6$, $R^{6.1}$ and $R^{6.2}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In aspects, $R^{6.1}$ and $R^{6.2}$ are hydrogen and R6 is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In aspects, $R^{6.1}$ and $R^{6.2}$ are hydrogen and R6 is substituted or unsubstituted heterocycloalkyl. In aspects, $R^{6.1}$ and $R^{6.2}$ are hydrogen and R6 is unsubstituted heterocycloalkyl. In aspects, $R^1$ is substituted (e.g. with an unsubstituted $C_1$-$C_5$ alkyl) or unsubstituted heteroaryl. In aspects, $R^1$ is substituted (e.g. with an unsubstituted $C_1$-$C_5$ alkyl) or unsubstituted furanyl. In aspects, $R^1$ is methyl-substituted furanyl.

In Formula (II): $R^1$ and $R^6$ are as described above (e.g., $R^6$ may be $R^7$-substituted or unsubstituted 3 to 6 membered heterocycloalkyl and $R^1$ may be $R^{1.4}$-substituted 5 to 6 membered heteroaryl). In aspects, $R^6$ is unsubstituted tetrahydrofuranyl and $R^1$ is $R^{1.4}$-substituted furanyl.

In Formula (II): $R^{6.1}$ may be independently hydrogen, halogen, —$CF_3$, —CN, —$CCl_3$, —COOH, —$CH_2$COOH, —$CONH_2$, —OH, —SH, —$SO_2$Cl, —$SO_3$H, —$SO_4$H, —$SO_2NH_2$, —$NO_2$, —$NH_2$, —$NHNH_2$, —$ONH_2$, —NHC=(O)$NHNH_2$, $R^{7.1}$-substituted or unsubstituted alkyl, $R^{7.1}$-substituted or unsubstituted heteroalkyl, $R^{7.1}$ substituted or unsubstituted cycloalkyl, $R^{7.1}$-substituted or unsubstituted heterocycloalkyl, $R^{7.1}$-substituted or unsubstituted aryl, or $R^{7.1}$-substituted or unsubstituted heteroaryl. $R^{6.1}$ may be $R^{7.1}$-substituted or unsubstituted (e.g., $C_1$-$C_{20}$ or $C_1$-$C_6$) alkyl, $R^{7.1}$-substituted or unsubstituted (e.g., 2 to 20 membered or 2 to 6 membered) heteroalkyl, $R^{7.1}$-substituted or unsubstituted (e.g., $C_3$-$C_8$ or $C_5$-$C_7$) cycloalkyl, $R^{7.1}$-substituted or unsubstituted (e.g., 3 to 8 membered or 3 to 6 membered) heterocycloalkyl, $R^{7.1}$-substituted or unsubstituted (e.g., $C_5$-$C_{10}$ or $C_5$-$C_6$) aryl, or $R^{7.1}$-substituted or unsubstituted (e.g., 5 to 10 membered or 5 to 6 membered) heteroaryl. In aspects, $R^{6.1}$ is $R^{7.1}$-substituted or unsubstituted $C_1$-$C_6$ alkyl. In aspects, $R^{6.1}$ is $R^{7.1}$-substituted or unsubstituted $C_1$-$C_5$ alkyl. In aspects, $R^{6.1}$ is $R^{7.1}$-substituted or unsubstituted $C_1$-$C_4$ alkyl. In aspects, $R^{6.1}$ is $R^{7.1}$-substituted or unsubstituted $C_1$-$C_3$ alkyl. In aspects, $R^{6.1}$ is $R^{7.1}$-substituted $C_1$-$C_6$ alkyl. In aspects, $R^{6.1}$ is $R^{7.1}$-substituted $C_1$-$C_5$ alkyl. In aspects, $R^{6.1}$ is $R^{7.1}$-substituted $C_1$-$C_4$ alkyl. In aspects, $R^{6.1}$ is $R^{7.1}$-substituted $C_1$-$C_3$ alkyl. In aspects, $R^{6.1}$ is unsubstituted $C_1$-$C_6$ alkyl. In aspects, $R^{6.1}$ is unsubstituted $C_1$-$C_5$ alkyl. In aspects, $R^{6.1}$ is unsubstituted $C_1$-$C_4$ alkyl. In aspects, $R^{6.1}$ is unsubstituted $C_1$-$C_3$ alkyl. In aspects, $R^{6.1}$ is unsubstituted methyl.

In Formula (II): $R^{6.2}$ is independently hydrogen, halogen, =O, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, $R^{7.2}$-substituted or unsubstituted alkyl, $R^{7.2}$-substituted or unsubstituted heteroalkyl, $R^{7.1}$-substituted or unsubstituted cycloalkyl, $R^{7.2}$-substituted or unsubstituted heterocycloalkyl, $R^{7.1}$-substituted or unsubstituted aryl, or $R^{7.2}$-substituted or unsubstituted heteroaryl. $R^{6.2}$ may be $R^{7.2}$-substituted or unsubstituted (e.g., $C_1$-$C_{20}$ or $C_1$-$C_6$) alkyl, $R^{7.2}$-substituted or unsubstituted (e.g., 2 to 20 membered or 2 to 6 membered) heteroalkyl, $R^{7.2}$-substituted or unsubstituted (e.g., $C_3$-$C_8$ or $C_5$-$C_7$) cycloalkyl, $R^{7.1}$-substituted or unsubstituted (e.g., 3 to 8 membered or 3 to 6 membered) heterocycloalkyl, $R^{7.1}$-substituted or unsubstituted (e.g., $C_5$-$C_{10}$ or $C_5$-$C_6$) aryl, or $R^{7.2}$-substituted or unsubstituted (e.g., 5 to 10 membered or 5 to 6 membered) heteroaryl. In aspects, $R^{6.2}$ is $R^{7.1}$-substituted or unsubstituted $C_1$-$C_6$ alkyl. In aspects, $R^{6.2}$ is $R^{7.2}$-substituted or unsubstituted $C_1$-$C_5$ alkyl. In aspects, $R^{6.2}$ is $R^{7.2}$-substituted or unsubstituted $C_1$-$C_4$ alkyl. In aspects, $R^{6.2}$ is $R^{7.2}$-substituted or unsubstituted $C_1$-$C_3$ alkyl. In aspects, $R^{6.2}$ is $R^{7.2}$-substituted $C_1$-$C_6$ alkyl. In aspects, $R^{6.2}$ is $R^{7.1}$-substituted $C_1$-$C_5$ alkyl. In aspects, $R^{6.2}$ is $R^{7.2}$-substituted $C_1$-$C_4$ alkyl. In aspects, $R^{6.2}$ is $R^{7.1}$-substituted $C_1$-$C_3$ alkyl. In aspects, $R^{6.2}$ is unsubstituted $C_1$-$C_6$ alkyl. In aspects, $R^{6.2}$ is unsubstituted $C_1$-$C_5$ alkyl. In aspects, $R^{6.2}$ is unsubstituted $C_1$-$C_4$ alkyl. In aspects, $R^{6.2}$ is unsubstituted $C_1$-$C_3$ alkyl. In aspects, $R^{6.2}$ is unsubstituted methyl.

In Formula (II): $R^7$, $R^{7.1}$ and $R^{7.2}$ are independently hydrogen, halogen, =O, =S, —$CF_3$, —CN, —$CCl_3$, —COOH, —$CH_2$COOH, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $R^7$, $R^{7.1}$ and $R^{7.2}$ may be independently unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, the A2A receptor antagonist is a compound of Formula (III) or a pharmaceutically acceptable salt thereof:

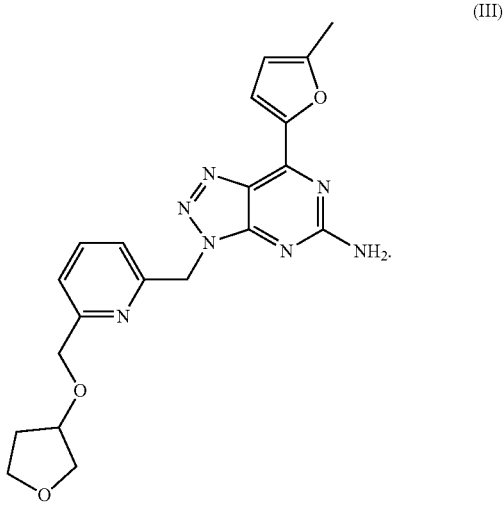 [SMILES: Cc1ccc(-c2nc(N)nc3c2nnn3Cc2cccc(COC3CCOC3)n2)o1]

(III)

The "compound of Formula (III)" may also be referred to herein as "Formula (III)" or as CPI-444. In aspects, the compound of Formula (III) is a compound of Formula (IIIA). In aspects, the compound of Formula (III) is a compound of Formula (IIIB). In aspects, the compound of Formula (III) is a mixture of the compounds of Formula (IIIA) and (IIIB). In aspects, the compound of Formula (III) is a racemic mixture of the compounds of Formula (IIIA) and Formula (IIIB).

In embodiments, the compound of Formula (III) is the compound of Formula (IIIA) or a pharmaceutically acceptable salt thereof:

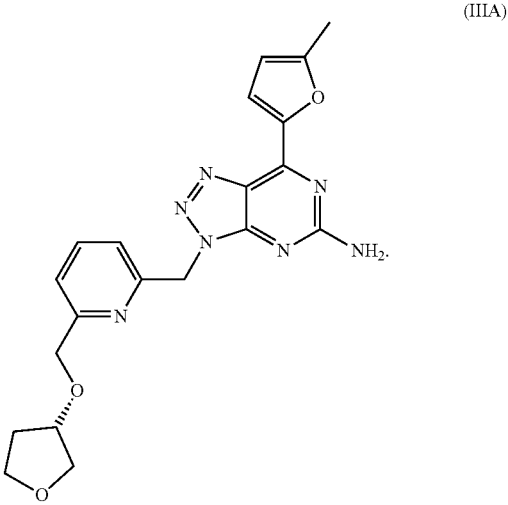

(IIIA)

In embodiments, the compound of Formula (III) is the compound of Formula (IIIB) or a pharmaceutically acceptable salt thereof:

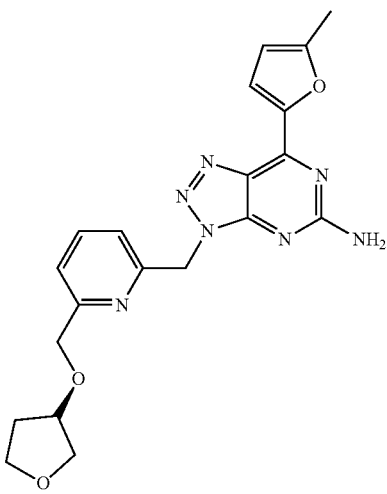

(IIIB)

Methods for making adenosine A2A receptor antagonists, including those of Formula (I), Formula (II), Formula (III), Formula (IIIA), and Formula (IIIB), are known in the art and described, for example, in WO 2017/112917, U.S. Pat. Nos. 8,450,328, 8,987,279, 9,376,443, and 9,765,080, the disclosures of which are incorporated by reference herein in their entirety.

The abbreviations used herein have their conventional meaning within the chemical and biological arts. The chemical structures and formulae set forth herein are constructed according to the standard rules of chemical valency known in the chemical arts. Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl," by itself or as part of another substituent, means a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

"Alkylene," by itself or as part of another substituent, means a divalent radical derived from an alkyl, as exemplified, but not limited by, —CH$_2$CH$_2$CH$_2$CH$_2$—. Typically, an alkyl (or alkyl ene) group will have from 1 to 24 carbon atoms, with those groups having 10 or fewer carbon atoms being preferred, and with 6 or fewer carbon atoms or 4 or few carbon atoms more preferred. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

"Heteroalkyl," by itself or in combination with another term, means a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond.

A heteroalkynyl may optionally include more than one triple bond and/or one or more double bonds in additional to the one or more triple bonds.

"Heteroalkylene," by itself or as part of another substituent, means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylene-diamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity.

Thus, the term "heteroalkyl" should not be interpreted herein as excluding specific heteroalkyl groups, such as —NR'R" or the like.

"Cycloalkyl" and "heterocycloalkyl," by themselves or in combination with other terms, mean non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

"Halo" or "halogen," by themselves or as part of another substituent, mean a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

"Acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

"Aryl" means a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5, 6-fused ring heteroarylene refers to two rings fused together, wherein one ring has 5 members and the other ring has 6 members, and wherein at least one ring is a heteroaryl ring. Likewise, a 6, 6-fused ring heteroaryl ene refers to two rings fused together, wherein one ring has 6 members and the other ring has 6 members, and wherein at least one ring is a heteroaryl ring. And a 6, 5-fused ring heteroaryl ene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

"Oxo" means an oxygen that is double bonded to a carbon atom.

"Alkylsulfonyl" means a moiety having the formula —S($O_2$)—R', where R' is a substituted or unsubstituted alkyl group as defined above. R' may have a specified number of carbons (e.g., "$C_1$-$C_4$ alkyl sulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkyl ene, alkenyl, heteroalkyl ene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R, —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, —R, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one aspect, the ring-forming substituents are attached to adjacent members of the base structure. For example, two ring-forming substituents attached to adjacent members of a cyclic base structure create a fused ring structure. In another aspect, the ring-forming substituents are attached to a single member of the base structure. For example, two ring-forming substituents attached to a single member of a cyclic base structure create a spirocyclic structure. In yet another aspect, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

"Heteroatom" or "ring heteroatom" are meant to include, oxygen (O), nitrogen (N), sulfur (S), phosphorus (P), and silicon (Si).

A "substituent group," as used herein, means a group selected from the following moieties: (A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from: (i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from: (a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)

NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, in some aspects, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other aspects, at least one or all of these groups are substituted with at least one size-limited substituent group. In other aspects, at least one or all of these groups are substituted with at least one lower substituent group.

In embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In aspects, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In aspects, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkyl ene, each substituted or unsubstituted aryl ene is a substituted or unsubstituted C$_6$-C$_{10}$ aryl ene, and/or each substituted or unsubstituted heteroaryl ene is a substituted or unsubstituted 5 to 9 membered heteroarylene.

The term "pharmaceutically acceptable salts" is meant to include salts of the active compounds that are prepared with relatively nontoxic acids or bases, depending on the particular substituents found on the compounds described herein. When the compounds described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When the compounds described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen-carbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain of the compounds described herein contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Compounds described herein can exist in unsolvated forms as well as solvated forms, including hydrated forms. In general, the solvated forms are equivalent to unsolvated forms.

Compounds described herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the disclosure. The disclosure is meant to include compounds in racemic and optically pure forms. Optically active (R)- and (S)-, or (D)- and (L)-isomers may be prepared using chiral synthons or chiral reagents, or resolved using conventional techniques. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. When the compounds described herein contain olefinic bonds or other centers of geometric asymmetry, and unless specified otherwise, it is intended that the compounds include both E and Z geometric isomers.

"Tautomer," as used herein, refers to one of two or more structural isomers which exist in equilibrium and which are readily converted from one isomeric form to another. It will be apparent to one skilled in the art that certain compounds may exist in tautomeric forms.

Unless otherwise stated, structures depicted herein are also meant to include compounds which differ only in the presence of one or more isotopically enriched atoms. For example, compounds may have the present structures except for the replacement of a hydrogen by a deuterium or tritium, or the replacement of a carbon by $^{13}C-$ or $^{14}C$-enriched carbon. The compounds described herein may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$).

The symbol denotes the point of attachment of a chemical moiety to the remainder of a molecule or chemical formula.

In embodiments, the compounds described herein may include multiple instances of $R^2$ and/or other variables. In aspects, each variable may optional be different and be appropriately labeled to distinguish each group for greater clarity. For example, where each $R^2$ is different, they may be referred to, for example, as $R^{2.1}$, $R^{2.2}$, $R^{2.3}$, and/or $R^{2.4}$ respectively, wherein the definition of $R^2$ is assumed by $R^{2.1}$, $R^{2.2}$, $R^{2.3}$, and/or $R^{2.4}$. The variables used within a definition of $R^2$ and/or other variables that appear at multiple instances and are different may similarly be appropriately labeled to distinguish each group for greater clarity. In aspects, the compound is a compound described herein (e.g., in an aspect, embodiment, example, claim, table, scheme, drawing, or figure).

The terms "a" or "an," as used in herein means one or more. In addition, the phrase "substituted with an," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{12}$-substituted or unsubstituted alkyl, a plurality of $R^{12}$ substituents may be attached to the alkyl moiety wherein each $R^{12}$ substituent is optionally different. Where an R-substituted moiety is substituted with a plurality R substituents, each of the R-substituents may be differentiated herein using a prime symbol (') such as R', R", etc. For example, where a moiety is $R^{12}$-substituted or unsubstituted alkyl, and the moiety is substituted with a plurality of $R^{12}$ substituents, the plurality of $R^{12}$ substituents may be differentiated as $R^{12\prime}$, $R^{12\prime\prime}$, $R^{12\prime\prime\prime}$, etc. In aspects, the plurality of R substituents is 3. In aspects, the plurality of R substituents is 2.

In embodiments, a compound as described herein may include multiple instances of $R^1$, $R^2$, $R^3$, $R^4$, $R^5$, $R^6$, $R^7$, $R^9$, $R^{10}$, $R^{11}$, $R^{12}$, $R^{13}$, $R^{14}$ and/or other variables. In such aspects, each variable may optional be different and be appropriately labeled to distinguish each group for greater clarity. For example, where each $R^1$, $R^2$, $R^3$, $R^4$, $R^5$, $R^6$, $R^7$, $R^9$, $R^{10}$, $R^{11}$, $R^{12}$, $R^{13}$, and/or $R^{14}$, is different, they may be referred to, for example, as $R^{1.1}$, $R^{1.2}$, $R^{1.3}$, $R^{1.4}$, $R^{2.1}$, $R^{2.2}$, $R^{2.3}$, $R^{2.4}$, $R^{3.1}$, $R^{3.2}$, $R^{3.3}$, $R^{3.4}$, $R^{4.1}$, $R^{4.2}$, $R^{4.3}$, $R^{4.4}$, $R^{5.1}$, $R^{5.2}$, $R^{5.3}$, $R^{5.4}$, $R^{6.1}$, $R^{6.2}$, $R^{6.3}$, $R^{6.4}$, $R^{7.1}$, $R^{7.2}$, $R^{7.3}$, $R^{7.4}$, $R^{9.1}$, $R^{9.2}$, $R^{9.3}$, $R^{9.4}$, $R^{10.1}$, $R^{10.2}$, $R^{10.3}$, $R^{10.4}$, $R^{11.1}$, $R^{11.2}$, $R^{11.3}$, $R^{11.4}$, $R^{12.1}$, $R^{12.2}$, $R^{12.3}$, $R^{12.4}$, $R^{13.1}$, $R^{13.2}$, $R^{13.3}$, $R^{13.4}$, $R^{14.1}$, $R^{14.2}$, $R^{14.3}$, and/or $R^{14.4}$, respectively, wherein the definition of $R^1$ is assumed by $R^{1.1}$, $R^{1.2}$, $R^{1.3}$, and/or $R^{1.4}$, the definition of $R^2$ is assumed by $R^{2.1}$, $R^{2.2}$, $R^{2.3}$, and/or $R^{2.4}$, the definition of $R^3$ is assumed by $R^{3.1}$, $R^{3.2}$, $R^{3.3}$, and/or $R^{3.4}$, the definition of $R^4$ is assumed by $R^{4.1}$, $R^{4.2}$, $R^{4.3}$, and/or $R^{4.4}$, the definition of $R^5$ is assumed by $R^{5.1}$, $R^{5.2}$, $R^{5.3}$, and/or $R^{5.4}$, the definition of $R^6$ is assumed by $R^{6.1}$, $R^{6.2}$, $R^{6.3}$, and/or $R^{6.4}$, the definition of $R^7$ is assumed by $R^{7.1}$, $R^{7.2}$, $R^{7.3}$, and/or $R^{7.4}$, the definition of $R^9$ is assumed by $R^{9.1}$, $R^{9.2}$, $R^{9.3}$, and/or $R^{9.4}$, the definition of $R^{10}$ is assumed by $R^{10.1}$, $R^{10.2}$, $R^{10.3}$, and/or $R^{10.4}$, the definition of $R^{11}$ is assumed by $R^{11.1}$, $R^{11.2}$, $R^{11.3}$, and/or $R^{11.4}$, the definition of $R^{12}$ is assumed by $R^{12.1}$, $R^{12.2}$, $R^{12.3}$, and/or $R^{12.4}$, the definition of $R^{13}$ is assumed by $R^{13.1}$, $R^{13.2}$, $R^{13.3}$, and/or $R^{13.4}$, the definition of $R^{14}$ is assumed by $R^{14.1}$, $R^{14.2}$, $R^{14.3}$, and/or $R^{14.4}$. The variables used within a definition of $R^1$, $R^2$, $R^3$, $R^4$, $R^5$, $R^6$, $R^7$, $R^9$, $R^{10}$, $R^{11}$, $R^{12}$, $R^{13}$ and/or $R^{14}$, and/or other variables that appear at multiple instances and are different may similarly be appropriately labeled to distinguish each group for greater clarity.

Descriptions of compounds herein are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Pharmaceutical Formulations

In aspects, the disclosure provides pharmaceutical compositions comprising micronized drug particles and a pharmaceutically acceptable excipient; wherein the micronized drug particles comprise an adenosine A2A receptor antagonist. In aspects, the adenosine A2A receptor antagonist is crystalline. In aspects, the pharmaceutically acceptable excipient comprises a filler, a disintegrant, a binder, or a combination of two or more thereof. In aspects, the pharmaceutically acceptable excipient further comprises a surfactant, a lubricant, a glidant, or a combination of two or more thereof.

In aspects, the disclosure provides granules comprising micronized drug particles and a pharmaceutically acceptable excipient; wherein the micronized drug particles comprise an adenosine A2A receptor antagonist. In aspects, the adenosine A2A receptor antagonist is crystalline. In aspects, the pharmaceutically acceptable excipient comprises a filler, a disintegrant, a binder, or a combination of two or more thereof. In aspects, the pharmaceutically acceptable excipient further comprises a surfactant, a lubricant, a glidant, or a combination of two or more thereof.

In aspects, the disclosure provides oral formulations comprising micronized drug particles and a pharmaceutically acceptable excipient; wherein the micronized drug particles comprise an adenosine A2A receptor antagonist. In aspects, the adenosine A2A receptor antagonist is crystalline. In aspects, the pharmaceutically acceptable excipient comprises a filler, a disintegrant, a binder, or a combination of two or more thereof. In aspects, the pharmaceutically acceptable excipient further comprises a surfactant, a lubricant, a glidant, or a combination of two or more thereof.

In aspects, the disclosure provides tablets comprising micronized drug particles and a pharmaceutically acceptable excipient; wherein the micronized drug particles comprise an adenosine A2A receptor antagonist. In aspects, the adenosine A2A receptor antagonist is crystalline. In aspects, the pharmaceutically acceptable excipient comprises a filler, a disintegrant, a binder, or a combination of two or more thereof. In aspects, the pharmaceutically acceptable excipient further comprises a surfactant, a lubricant, a glidant, or a combination of two or more thereof.

In aspects, the disclosure provides powders comprising micronized drug particles and a pharmaceutically acceptable excipient; wherein the micronized drug particles comprise an adenosine A2A receptor antagonist. In aspects, the adenosine A2A receptor antagonist is crystalline. In aspects, the pharmaceutically acceptable excipient comprises a filler, a disintegrant, a binder, or a combination of two or more thereof. In aspects, the pharmaceutically acceptable excipient further comprises a surfactant, a lubricant, a glidant, or a combination of two or more thereof.

In aspects, the disclosure provides beads comprising an inert core and a drug layer; wherein the drug layer comprises micronized drug particles and a pharmaceutically acceptable excipient; wherein the micronized drug particles comprise an adenosine A2A receptor antagonist. In aspects, the adenosine A2A receptor antagonist is crystalline. In aspects, the pharmaceutically acceptable excipient comprises a filler, a disintegrant, a binder, or a combination of two or more thereof. In aspects, the pharmaceutically acceptable excipient further comprises a surfactant, a lubricant, a glidant, or a combination of two or more thereof. The drug layer surrounds the inert core.

In aspects of the pharmaceutical compositions, oral formulations, granules, tablets, capsules, powders, and beads described herein, the adenosine A2A receptor antagonist is a compound of Formula (I) or a pharmaceutically acceptable salt thereof. In aspects, the compound of Formula (I) is in free base form. In aspects, the compound of Formula (I) is in the form of a pharmaceutically acceptable salt. In aspects, the compound of Formula (I) is crystalline In aspects, the adenosine A2A receptor antagonist is a compound of Formula (II) or a pharmaceutically acceptable salt thereof. In aspects, the compound of Formula (II) is in free base form. In aspects, the compound of Formula (II) is in the form of a pharmaceutically acceptable salt. In aspects, the compound of Formula (II) is crystalline. In aspects, the adenosine A2A receptor antagonist is a compound of Formula (III) or a pharmaceutically acceptable salt thereof. In aspects, the compound of Formula (III) is in the form of a pharmaceutically acceptable salt. In aspects, the compound of Formula (III) is in free base form. In aspects, the compound of Formula (III) is crystalline. In aspects, the adenosine A2A receptor antagonist is a compound of Formula (IIIA) or a pharmaceutically acceptable salt thereof. In aspects, the compound of Formula (IIIA) is in free base form. In aspects, the compound of Formula (IIIA) is in the form of a pharmaceutically acceptable salt. In aspects, the compound of Formula (IIIA) is crystalline. In aspects, the adenosine A2A receptor antagonist is a compound of Formula (IIIB) or a pharmaceutically acceptable salt thereof. In aspects, the compound of Formula (IIIB) is in free base form. In aspects, the compound of Formula (IIIB) is in the form of a pharmaceutically acceptable salt. In aspects, the compound of Formula (IIIB) is crystalline. In aspects, the adenosine A2A receptor antagonist is a mixture of a compound of Formula (IIIA) or a pharmaceutically acceptable salt thereof and a compound of Formula (IIIB) or a pharmaceutically acceptable salt thereof. In aspects, the adenosine A2A receptor antagonist is a racemic mixture of a compound of Formula (IIIA) or a pharmaceutically acceptable salt thereof and a compound of Formula (IIIB) or a pharmaceutically acceptable salt thereof.

In aspects of the pharmaceutical compositions, oral formulations, granules, tablets, capsules, powders, and beads described herein, the adenosine A2A receptor antagonist is present in an effective amount. In aspects, the adenosine A2A receptor antagonist is present in an amount of about 1 wt % to about 50 wt %. In aspects, the adenosine A2A receptor antagonist is present in an amount of about 1 wt % to about 40 wt %. In aspects, the adenosine A2A receptor antagonist is in an amount of about 1 wt % to about 30 wt %. In aspects, the adenosine A2A receptor antagonist is in an amount of about 1 wt % to about 25 wt %. In aspects, the adenosine A2A receptor antagonist is in an amount of about 1 wt % to about 20 wt %. In aspects, the adenosine A2A receptor antagonist is in an amount of about 1 wt % to about 15 wt %. In aspects, the adenosine A2A receptor antagonist is in an amount of about 1 wt % to about 10 wt %. In aspects, the adenosine A2A receptor antagonist is in an amount of about 2 wt % to about 48 wt %. In aspects, the adenosine A2A receptor antagonist is in an amount of about 3 wt % to about 47 wt %. In aspects, the adenosine A2A receptor antagonist is in an amount of about 4 wt % to about 46 wt %. In aspects, the adenosine A2A receptor antagonist is in an amount of about 5 wt % to about 45 wt %. In aspects, the adenosine A2A receptor antagonist is in an amount of about 6 wt % to about 44 wt %. In aspects, the adenosine A2A receptor antagonist is in an amount of about 7 wt % to about 43 wt %. In aspects, the adenosine A2A receptor antagonist is in an amount of about 8 wt % to about 42 wt %. In aspects, the adenosine A2A receptor antagonist is in an amount of about 9 wt % to about 41 wt %. In aspects, the adenosine A2A receptor antagonist is in an amount of about 10 wt % to about 40 wt %. In aspects, the adenosine A2A receptor antagonist is in an amount of about 11 wt % to about 39 wt %. In aspects, the adenosine A2A receptor antagonist is in an amount of about 12 wt % to about 38 wt %. In aspects, the adenosine A2A receptor antagonist is in an amount of about 13 wt % to about 37 wt %. In aspects, the adenosine A2A receptor antagonist is in an amount of about 14 wt % to about 36 wt %. In aspects, the adenosine A2A receptor antagonist is in an amount of about 15 wt % to about 35 wt %. In aspects, the adenosine A2A receptor antagonist is in an amount of about 16 wt % to about 34 wt %. In aspects, the adenosine A2A receptor antagonist is in an amount of about 17 wt % to about 33 wt %. In aspects, the adenosine A2A receptor antagonist is in an amount of about 18 wt % to about 32 wt %. In aspects, the adenosine A2A receptor antagonist is in an amount of about 19 wt % to about 31 wt %. In aspects, the adenosine A2A receptor antagonist is in an amount of about 20 wt % to about 30 wt %. In aspects, the adenosine A2A receptor antagonist is in an amount of about 21 wt % to about 29 wt %. In aspects, the adenosine A2A receptor antagonist is in an amount of about 22 wt % to about 28 wt %. In aspects, the adenosine A2A receptor antagonist is in an amount of about 23 wt % to about 27 wt %. In aspects, the adenosine A2A receptor antagonist is in an amount of about 24 wt % to about 26 wt %. In aspects, the adenosine A2A receptor antagonist is in an amount of about 15 wt %. In aspects, the adenosine A2A receptor antagonist is in an amount of about 16 wt %. In aspects, the adenosine A2A receptor antagonist is in an amount of about 17 wt %. In aspects, the adenosine A2A receptor antagonist is in an amount of about 18 wt %. In aspects, the adenosine A2A receptor antagonist is in an amount of about 19 wt %. In aspects, the adenosine A2A receptor antagonist is in an amount of about 20 wt %. In aspects, the adenosine A2A receptor antagonist is in an amount of about 21 wt %. In aspects, the adenosine A2A receptor antagonist is in an amount of about 22 wt %. In aspects, the adenosine A2A receptor antagonist is in an amount of about 23 wt %. In aspects, the adenosine A2A receptor antagonist is in an amount of about 24 wt %. In aspects, the adenosine A2A receptor antagonist is in an amount of about 25 wt %. In aspects, the adenosine A2A receptor antagonist is in an amount of about 26 wt %. In aspects, the adenosine A2A receptor antagonist is in an amount of about 27 wt %. In aspects, the adenosine A2A receptor antagonist is in an amount of about 28 wt %. In aspects, the adenosine A2A receptor antagonist is in an amount of about 29 wt %. In aspects, the adenosine A2A receptor antagonist is in an amount of about 30 wt %. In aspects, the adenosine A2A receptor antagonist is in an amount of about 31 wt %. In aspects, the adenosine A2A receptor antagonist is in an amount of about 32 wt %. In aspects, the adenosine A2A receptor antagonist is in an amount of about 33 wt %. In aspects, the adenosine A2A receptor antagonist is in an amount of about 34 wt %. In aspects, the adenosine A2A receptor antagonist is in an amount of about 35 wt %.

In aspects of the pharmaceutical compositions, oral formulations, granules, tablets, capsules, powders, and beads described herein, the micronized drug particles have a size distribution with a D90 of about 50 microns or less. In aspects, the micronized drug particles have a size distribution with a D90 of about 45 microns or less. In aspects, the micronized drug particles have a size distribution with a D90 of about 40 microns or less. In aspects, the micronized drug particles have a size distribution with a D90 of about 35 microns or less. In aspects, the micronized drug particles have a size distribution with a D90 of about 30 microns or less. In aspects, the micronized drug particles have a size distribution with a D90 of about 29 microns or less. In aspects, the micronized drug particles have a size distribution with a D90 of about 28 microns or less. In aspects, the micronized drug particles have a size distribution with a D90 of about 27 microns or less. In aspects, the micronized drug particles have a size distribution with a D90 of about 26 microns or less. In aspects, the micronized drug particles have a size distribution with a D90 of about 25 microns or less. In aspects, the micronized drug particles have a size distribution with a D90 of about 24 microns or less. In aspects, the micronized drug particles have a size distribution with a D90 of about 23 microns or less. In aspects, the micronized drug particles have a size distribution with a D90 of about 22 microns or less. In aspects, the micronized drug particles have a size distribution with a D90 of about 21 microns or less. In aspects, the micronized drug particles have a size distribution with a D90 of about 20 microns or less. In aspects, the micronized drug particles have a size distribution with a D90 of about 19 microns or less. In aspects, the micronized drug particles have a size distribution with a D90 of about 18 microns or less. In aspects, the micronized drug particles have a size distribution with a D90 of about 17 microns or less. In aspects, the micronized drug particles have a size distribution with a D90 of about 16 microns or less. In aspects, the micronized drug particles have a size distribution with a D90 of about 15 microns or less. In aspects, the micronized drug particles have a size distribution with a D90 of about 14 microns or less. In aspects, the micronized drug particles have a size distribution with a D90 of about 13 microns or less. In aspects, the micronized drug particles have a size distribution with a D90 of about 12 microns or less. In aspects, the micronized drug particles have a size distribution with a D90 of about 11 microns or less. In aspects, the micronized drug particles have a size distribution with a D90 of about 10 microns or less. In aspects, the micronized drug particles have a size distribution with a D90 of about 9 microns or less. In aspects, the micronized drug particles have a size distribution with a D90 of about 8 microns or less. In aspects, the micronized drug particles have a size distribution with a D90 of about 7 microns or less. In aspects, the micronized drug particles have a size distribution with a D90 of about 6 microns or less. In aspects, the micronized drug particles have a size distribution with a D90 of about 5 microns or less. The particle size distribution of the micronized drug particles described herein is measured by laser diffraction spectroscopy.

In aspects of the pharmaceutical compositions, oral formulations, granules, tablets, capsules, powders, and beads described herein, the micronized drug particles have a size distribution with a D50 of about 15 microns or less. In aspects, the micronized drug particles have a size distribution with a D50 of about 14 microns or less. In aspects, the micronized drug particles have a size distribution with a D50 of about 13 microns or less. In aspects, the micronized drug particles have a size distribution with a D50 of about 12 microns or less. In aspects, the micronized drug particles have a size distribution with a D50 of about 11 microns or less. In aspects, the micronized drug particles have a size distribution with a D50 of about 10 microns or less. In aspects, the micronized drug particles have a size distribution with a D50 of about 9.5 microns or less. In aspects, the micronized drug particles have a size distribution with a D50 of about 9 microns or less. In aspects, the micronized drug particles have a size distribution with a D50 of about 8.5 microns or less. In aspects, the micronized drug particles have a size distribution with a D50 of about 8 microns or less. In aspects, the micronized drug particles have a size distribution with a D50 of about 7.5 microns or less. In aspects, the micronized drug particles have a size distribution with a D50 of about 7 microns or less. In aspects, the micronized drug particles have a size distribution with a D50 of about 6.5 microns or less. In aspects, the micronized drug particles have a size distribution with a D50 of about 6 microns or less. In aspects, the micronized drug particles have a size distribution with a D50 of about 5.5 microns or less. In aspects, the micronized drug particles have a size distribution with a D50 of about 5 microns or less. In aspects, the micronized drug particles have a size distribution with a D50 of about 4.5 microns or less. In aspects, the micronized drug particles have a size distribution with a D50 of about 4 microns or less. In aspects, the micronized drug particles have a size distribution with a D50 of about 3.5 microns or less. In aspects, the micronized drug particles have a size distribution with a D50 of about 3 microns or less. In aspects, the micronized drug particles have a size distribution with a D50 of about 2.5 microns or less. In aspects, the micronized drug particles have a size distribution with a D50 of about 2 microns or less. The particle size distribution of the micronized drug particles described herein is measured by laser diffraction spectroscopy.

In aspects of the pharmaceutical compositions, oral formulations, granules, tablets, capsules, powders, and beads described herein, the micronized drug particles have a size distribution with a D10 of about 10 microns or less. In aspects, the micronized drug particles have a size distribution with a D10 of about 9 microns or less. In aspects, the micronized drug particles have a size distribution with a D10 of about 8 microns or less. In aspects, the micronized drug particles have a size distribution with a D10 of about 7 microns or less. In aspects, the micronized drug particles have a size distribution with a D10 of about 6 microns or less. In aspects, the micronized drug particles have a size distribution with a D10 of about 5 microns or less. In aspects, the micronized drug particles have a size distribution with a D10 of about 4 microns or less. In aspects, the micronized drug particles have a size distribution with a D10 of about 3 microns or less. In aspects, the micronized drug particles have a size distribution with a D10 of about 2.9 microns or less. In aspects, the micronized drug particles have a size distribution with a D10 of about 2.8 microns or less. In aspects, the micronized drug particles have a size distribution with a D10 of about 2.7 microns or less. In aspects, the micronized drug particles have a size distribution with a D10 of about 2.6 microns or less. In aspects, the micronized drug particles have a size distribution with a D10 of about 2.5 microns or less. In aspects, the micronized drug particles have a size distribution with a D10 of about 2.4 microns or less. In aspects, the micronized drug particles have a size distribution with a D10 of about 2.3 microns or less. In aspects, the micronized drug particles have a size distribution with a D10 of about 2.2 microns or less. In aspects, the micronized drug particles have a size distribution with a D10 of about 2.1 microns or less. In aspects, the micronized drug particles have a size distribution with a D10 of about 2 microns or less. In aspects, the micronized drug particles have a size distribution with a D10 of about 1.9 microns or less. In aspects, the micronized drug particles have a size distribution with a D10 of about 1.8 microns or less. In aspects, the micronized drug particles have a size distribution with a D10 of about 1.7 microns or less. In aspects, the micronized drug particles have a size distribution with a D10 of about 1.6 microns or less. In aspects, the micronized drug particles have a size distribution with a D10 of about 1.5 microns or less. In aspects, the micronized drug particles have a size distribution with a D10 of about 1.4 microns or less. In aspects, the micronized drug particles have a size distribution with a D10 of about 1.3 microns or less. In aspects, the micronized drug particles have a size distribution with a D10 of about 1.2 microns or less. In aspects, the micronized drug particles have a size distribution with a D10 of about 1.1 microns or less. In aspects, the micronized drug particles have a size distribution with a D10 of about 1 microns or less. In aspects, the micronized drug particles have a size distribution with a D10 of about 0.9 microns or less. In aspects, the micronized drug particles have a size distribution with a D10 of about 0.8 microns or less. In aspects, the micronized drug particles have a size distribution with a D10 of about 0.7 microns or less. In aspects, the micronized drug particles have a size distribution with a D10 of about 0.6 microns or less. In aspects, the micronized drug particles have a size distribution with a D10 of about 0.5 microns or less. The particle size distribution of the micronized drug particles described herein is measured by laser diffraction spectroscopy.

In aspects of the pharmaceutical compositions, oral formulations, granules, tablets, capsules, powders, and beads described herein, the micronized drug particles have a size distribution with a D90 of less than 20 microns; a D50 of less than 10 microns; and a D10 of less than 5 microns. In aspects, the micronized drug particles have a size distribution with a D90 of less than 20 microns; a D50 of less than 6 microns; and a D10 of less than 2 micron. In aspects, the micronized drug particles have a size distribution with a D90 of less than 15 microns; a D50 of less than 8 microns; and a D10 of less than 3 microns. In aspects, the micronized drug particles have a size distribution with a D90 of less than 12 microns; a D50 of less than 5 microns; and a D10 of less than 1.5 microns. In aspects, the micronized drug particles have a size distribution with a D90 of less than 11 microns; a D50 of less than 4.5 microns; and a D10 of less than 1.2 microns. In aspects, the micronized drug particles have a size distribution with a D90 of less than 10 microns; a D50 of less than 4 microns; and a D10 of less than 1.1 microns. In aspects, the micronized drug particles have a size distribution with a D90 of less than 9 microns; a D50 of less than 3.5 microns; and a D10 of less than 1 micron. The particle size distribution of the micronized drug particles described herein is measured by laser diffraction spectroscopy.

In aspects of the pharmaceutical compositions, oral formulations, granules, tablets, capsules, powders, and beads described herein, any pharmaceutically acceptable excipient known in the art can be used. In aspects, the pharmaceutically acceptable excipient comprises a filler. In aspects, the pharmaceutically acceptable excipient comprises a disintegrant. In aspects, the pharmaceutically acceptable excipient comprises a binder. In aspects, the pharmaceutically acceptable excipient comprises a filler and a disintegrant. In aspects, the pharmaceutically acceptable excipient comprises a filler and a binder. In aspects, the pharmaceutically acceptable excipient comprises a disintegrant and a binder. In aspects, the pharmaceutically acceptable excipient comprises a filler, a disintegrant, and a binder. In aspects, the pharmaceutically acceptable excipient comprises a filler and a lubricant. In aspects, the pharmaceutically acceptable excipient comprises a disintegrant and a lubricant. In aspects, the pharmaceutically acceptable excipient comprises a binder and a lubricant. In aspects, the pharmaceutically acceptable excipient comprises a filler, a disintegrant, and a lubricant. In aspects, the pharmaceutically acceptable excipient comprises a filler, a binder, and a lubricant. In aspects, the pharmaceutically acceptable excipient comprises a disintegrant, a binder, and a lubricant. In aspects, the pharmaceutically acceptable excipient comprises a filler, a disintegrant, a binder, and a lubricant. In aspects, the pharmaceutically acceptable excipient further comprises a surfactant, a glidant, or a combination thereof. In aspects, the pharmaceutically acceptable excipient may further comprise one or more additional compounds to enhance the manufacture, powder flow, chemical properties (e.g., stability), or biological properties (e.g., absorption) of the pharmaceutical compositions, granules, tablets, capsules, powders, and beads described herein.

In aspects of the pharmaceutical compositions, oral formulations, granules, tablets, capsules, powders, and beads described herein, the filler can be any filler known in the art. In aspects, the filler comprises polyols, maltodextrin, microcrystalline cellulose, or a combination of two or more thereof. In aspects, the filler is a polyol. In aspects, the filler is mannitol, sorbitol, isomaltose, maltitol, lactose, sucrose, amylose, glucose, dextrose, lactitol, erythritol, arabitol, xylitol, trehalose, ribitol, inositol, or a combination of two or more thereof. In aspects, the filler is mannitol. In aspects, the filler is maltitol. In aspects, the filler is lactose. In aspects, the filler is maltodextrin. In aspects, the filler is microcrystalline cellulose. In aspects, the filler is a polyol and maltodextrin. In aspects, the filler comprises: (i) maltodextrin and (ii) mannitol, sorbitol, isomaltose, maltitol, lactose, sucrose, amylose, glucose, dextrose, lactitol, erythritol, arabitol, xylitol, trehalose, ribitol, inositol, or a combination of two or more thereof. In aspects, the filler comprises: (i) maltodextrin and (ii) mannitol. In aspects, the filler comprises: (i) maltodextrin and (ii) lactose. In aspects, the filler is a polyol and microcrystalline cellulose. In aspects, the filler comprises: (i) microcrystalline cellulose and (ii) mannitol, sorbitol, isomaltose, maltitol, lactose, sucrose, amylose, glucose, dextrose, lactitol, erythritol, arabitol, xylitol, trehalose, ribitol, inositol, or a combination of two or more thereof. In aspects, the filler comprises: (i) microcrystalline cellulose and (ii) mannitol. In aspects, the filler comprises: (i) microcrystalline cellulose and (ii) lactose. In aspects, the filler is a maltodextrin and microcrystalline cellulose. In aspects, the filler is a polyol, maltodextrin, and microcrystalline cellulose. In aspects, the filler comprises: (i) maltodextrin, (ii) microcrystalline cellulose, and (iii) mannitol, sorbitol, isomaltose, maltitol, lactose, sucrose, amylose, glucose, dextrose, lactitol, erythritol, arabitol, xylitol, trehalose, ribitol, inositol, or a combination of two or more thereof. In aspects, the filler comprises: (i) maltodextrin, (ii) microcrystalline cellulose, and (iii) mannitol. In aspects, the filler comprises: (i) maltodextrin, (ii) microcrystalline cellulose, and (iii) lactose.

When the filler in the compositions, oral formulations, granules, tablets, capsules, powders, and beads described herein comprises mannitol, the mannitol is crystalline mannitol, spray-dried mannitol, or a combination thereof. In aspects, the mannitol is a crystalline mannitol. In aspects, the mannitol is a spray-dried mannitol. In aspects, the mannitol comprises crystalline mannitol and spray-dried mannitol, wherein the ratio of the crystalline mannitol to the spray-dried mannitol is from about 25:1 to about 1:25; or from about 20:1 to about 1:20; or from about 15:1 to about 1:15; or from about 10:1 to about 1:10; or from about 8:1 to about 1:8. In aspects, the ratio of the crystalline mannitol to the spray-dried mannitol is from about 5:1 to about 1:5. In aspects, the ratio of the crystalline mannitol to the spray-dried mannitol is from about 3:1 to about 1:3. In aspects, the ratio of the crystalline mannitol to the spray-dried mannitol is from about 3:1 to about 1:1. In aspects, the ratio of the crystalline mannitol to the spray-dried mannitol is from about 2.5:1 to about 1.5:1.

In aspects, the ratio of the crystalline mannitol to the spray-dried mannitol is about 2:1. In aspects, the mannitol has a particle size (mean diameter, measured by laser diffraction) from about 10 microns to about 600 microns. In aspects, the mannitol has a particle size (mean diameter, measured by laser diffraction) from about 25 microns to about 250 microns. In aspects, the mannitol is a crystalline mannitol having a particle size (mean diameter, measured by laser diffraction) from about 25 microns to about 160 microns. In aspects, the mannitol is a crystalline mannitol having a particle size (mean diameter, measured by laser diffraction) from about 40 microns to about 60 microns. In aspects, the mannitol is a crystalline mannitol having a particle size (mean diameter, measured by laser diffraction) of about 50 microns (commercially available as PEARLITOL® 50C). In aspects, the mannitol is spray-dried mannitol having a particle size from about 100 microns to about 500 microns. In aspects, the mannitol is spray-dried mannitol having a particle size from about 100 microns to about 200 microns. In aspects, the mannitol is spray-dried mannitol having a particle size of about 180 microns (commercially available as PEARLITOL® 200 SD). In aspects, the mannitol comprises a crystalline mannitol having a particle size from about 25 microns to about 160 microns, and a spray-dried mannitol having a particle size from about 80 microns to about 200 microns, where the ratio of the crystalline mannitol to the spray-dried mannitol is from about 10:1 to about 1:10; or from about 5:1 to about 1:5; or the ratio is from about 3:1 to about 1:3, or the ratio is from about 3:1 to about 1:1; or the ratio is from about 2.5:1 to about 1.5:1; or the ratio is about 2:1; or the ratio is about 1.9:1; or the ratio is from about 2:1 to about 1.9:1.

In aspects of the pharmaceutical compositions, oral formulations, granules, tablets, capsules, powders, and beads described herein, the filler is present in the pharmaceutical compositions, granules, tablets, capsules, powders, and beads in an appropriate amount. In aspects, the filler is present in an amount from about 10 wt % to about 95 wt %; or from about 15 wt % to about 90 wt %; or from about 20 wt % to about 80 wt %; or from about 20 wt % to about 75 wt %; or from about 20 wt % to about 70 wt %. In aspects, the filler is present in an amount from about 30 wt % to about 80 wt %. In aspects, the filler is present in an amount from about 30 wt % to about 75 wt %. In aspects, the filler is in an amount from about 30 wt % to about 70 wt %. In aspects, the filler is in an amount from about 30 wt % to about 65 wt %. In aspects, the filler is in an amount from about 40 wt % to about 80 wt %. In aspects, the filler is in an amount from about 40 wt % to about 75 wt %. In aspects, the filler is in an amount from about 40 wt % to about 70 wt %. In aspects, the filler is in an amount from about 40 wt % to about 65 wt %. In aspects, the filler is in an amount from about 50 wt % to about 80 wt %. In aspects, the filler is in an amount from about 50 wt % to about 75 wt %. In aspects, the filler is in an amount from about 50 wt % to about 70 wt %. In aspects, the filler is in an amount from about 50 wt % to about 65 wt %. In aspects, the filler is in an amount from about 55 wt % to about 80 wt %. In aspects, the filler is in an amount from about 55 wt % to about 75 wt %. In aspects, the filler is in an amount from about 55 wt % to about 70 wt %. In aspects, the filler is in an amount from about 51 wt % to about 69 wt %. In aspects, the filler is in an amount from about 52 wt % to about 68 wt %. In aspects, the filler is in an amount from about 53 wt % to about 67 wt %. In aspects, the filler is in an amount from about 54 wt % to about 66 wt %. In aspects, the filler is in an amount from about 55 wt % to about 65 wt %. In aspects, the filler is in an amount from about 56 wt % to about 64 wt %. In aspects, the filler is in an amount from about 57 wt % to about 63 wt %. In aspects, the filler is in an amount from about 58 wt % to about 62 wt %. In aspects, the filler is in an amount from about 59 wt % to about 61 wt %. In aspects, the filler is in an amount from about 60 wt % to about 61 wt %. In aspects, the filler is in an amount from about 60 wt % to about 62 wt %. In aspects, the filler is in an amount of about 50 wt %. In aspects, the filler is in an amount of about 51 wt %. In aspects, the filler is in an amount of about 52 wt %. In aspects, the filler is in an amount of about 53 wt %. In aspects, the filler is in an amount of about 54 wt %. In aspects, the filler is in an amount of about 55 wt %. In aspects, the filler is in an amount of about 56 wt %. In aspects, the filler is in an amount of about 57 wt %. In aspects, the filler is in an amount of about 58 wt %. In aspects, the filler is in an amount of about 59 wt %. In aspects, the filler is in an amount of about 60 wt %. In aspects, the filler is in an amount of about 60.25 wt %. In aspects, the filler is in an amount of about 60.5 wt %. In aspects, the filler is in an amount of about 60.75 wt %. In aspects, the filler is in an amount of about 61 wt %. In aspects, the filler is in an amount of about 61.25 wt %. In aspects, the filler is in an amount of about 61.5 wt %. In aspects, the filler is in an amount of about 61.75 wt %. In aspects, the filler is in an amount of about 62 wt %. In aspects, the filler is in an amount of about 62.25 wt %. In aspects, the filler is in an amount of about 62.5 wt %. In aspects, the filler is in an amount of about 62.75 wt %. In aspects, the filler is in an amount of about 63 wt %. In aspects, the filler is in an amount of about 64 wt %. In aspects, the filler is in an amount of about 65 wt %. In aspects, the filler is in an amount of about 66 wt %. In aspects, the filler is in an amount of about 67 wt %. In aspects, the filler is in an amount of about 68 wt %. In aspects, the filler is in an amount of about 69 wt %. In aspects, the filler is in an amount of about 70 wt %.

In aspects of the pharmaceutical compositions, oral formulations, granules, tablets, capsules, powders, and beads described herein, the disintegrant can be any disintegrant known in the art. In aspects, the disintegrant is a super disintegrant. In aspects, the disintegrant is a pharmaceutically acceptable polymer. In aspects, the disintegrant comprises carboxyalkyl cellulose (e.g., carboxymethyl cellulose or crosslinked carboxymethyl cellulose), sodium starch glycolate, crosslinked polyvinylpyrrolidone polymers, or a combination of two or more thereof. In aspects, the disintegrant comprises a carboxyalkyl cellulose. In aspects, the disintegrant comprises carboxymethyl cellulose. In aspects, the disintegrant comprises crosslinked carboxymethyl cellulose. In aspects, the disintegrant comprises sodium starch glycolate. In aspects, the disintegrant comprises a crosslinked polyvinylpyrrolidone polymer. In aspects, the disintegrant comprises a carboxyalkyl cellulose and sodium starch glycolate. In aspects, the disintegrant comprises a crosslinked carboxyalkyl cellulose and sodium starch glycolate. In aspects, the disintegrant comprises a carboxyalkyl cellulose and a crosslinked polyvinylpyrrolidone polymer. In aspects, the disintegrant comprises a crosslinked carboxyalkyl cellulose and a crosslinked polyvinylpyrrolidone polymer. In aspects, the disintegrant comprises a carboxyalkyl cellulose, sodium starch glycolate, and a crosslinked polyvinylpyrrolidone polymer. In aspects, the disintegrant comprises a crosslinked carboxyalkyl cellulose, sodium starch glycolate, and a crosslinked polyvinylpyrrolidone polymer. In aspects, the disintegrant comprises sodium starch glycolate and a crosslinked polyvinylpyrrolidone polymer.

In aspects of the pharmaceutical compositions, oral formulations, granules, tablets, capsules, powders, and beads described herein, the disintegrant is present in the pharmaceutical compositions, granules, tablets, capsules, powders, and beads in an appropriate amount. In aspects, the disintegrant is present in an amount from about 0.5 wt % to about 30 wt %. In aspects, the disintegrant is present in an amount from about 1 wt % to about 25 wt %. In aspects, the disintegrant is present in an amount from about 1 wt % to about 20 wt %. In aspects, the disintegrant is in an amount from about 1 wt % to about 15 wt %. In aspects, the disintegrant is in an amount from about 1 wt % to about 14 wt %. In aspects, the disintegrant is in an amount from about 1 wt % to about 13 wt %. In aspects, the disintegrant is in an amount from about 1 wt % to about 12 wt %. In aspects, the disintegrant is in an amount from about 1 wt % to about 11 wt %. In aspects, the disintegrant is in an amount from about 1 wt % to about 10 wt %. In aspects, the disintegrant is in an amount from about 2 wt % to about 15 wt %. In aspects, the disintegrant is in an amount from about 2 wt % to about 14 wt %. In aspects, the disintegrant is in an amount from about 2 wt % to about 13 wt %. In aspects, the disintegrant is in an amount from about 2 wt % to about 12 wt %. In aspects, the disintegrant is in an amount from about 2 wt % to about 11 wt %. In aspects, the disintegrant is in an amount from about 2 wt % to about 10 wt %. In aspects, the disintegrant is in an amount from about 3 wt % to about 11 wt %. In aspects, the disintegrant is in an amount from about 4 wt % to about 10 wt %. In aspects, the disintegrant is in an amount from about 5 wt % to about 9 wt %. In aspects, the disintegrant is in an amount from about 6 wt % to about 8 wt %. In aspects, the disintegrant is in an amount of about 7 wt %. In aspects, the disintegrant is in an amount of about 5 wt %. In aspects, the disintegrant is in an amount of about 6 wt %. In aspects, the disintegrant is in an amount from about 4 wt % to about 12 wt %. In aspects, the disintegrant is in an amount from about 5 wt % to about 11 wt %. In aspects, the disintegrant is in an amount from about 6 wt % to about 10 wt %. In aspects, the disintegrant is in an amount from about 7 wt % to about 9 wt %. In aspects, the disintegrant is in an amount of about 8 wt %. In aspects, the disintegrant is in an amount from about 5 wt % to about 13 wt %. In aspects, the disintegrant is in an amount from about 6 wt % to about 12 wt %. In aspects, the disintegrant is in an amount from about 7 wt % to about 11 wt %. In aspects, the disintegrant is in an amount from about 8 wt % to about 10 wt %. In aspects, the disintegrant is in an amount of about 9 wt %. In aspects, the disintegrant is in an amount of about 10 wt %. In aspects, the disintegrant is in an amount of about 11 wt %.

In aspects of the pharmaceutical compositions, oral formulations, granules, tablets, capsules, powders, and beads described herein, the binder can be any binder known in the art. In aspects, the binder is a pharmaceutically acceptable polymer. In aspects, the binder comprises a hydroxyalkyl cellulose, an alkyl cellulose, corn starch, polyethylene glycol, polyethylene oxide, polyvinylpyrrolidone, or a combination of two or more thereof. In aspects, the binder comprises a hydroxyalkyl cellulose. In aspects, the binder comprises an alkyl cellulose. In aspects, the binder comprises corn starch. In aspects, the binder comprises polyethylene glycol. In aspects, the binder comprises polyethylene oxide. In aspects, the binder comprises polyvinylpyrrolidone. In aspects, the binder comprises a hydroxyalkyl cellulose and an alkyl cellulose. In aspects, the binder comprises a hydroxyalkyl cellulose, an alkyl cellulose, and polyethylene glycol. In aspects, the binder comprises a hydroxyalkyl cellulose and polyethylene glycol. In aspects, the binder comprises an alkyl cellulose and polyethylene glycol. In aspects, the binder comprises hydroxypropyl cellulose, hydroxyethyl cellulose, hydroxypropylmethyl cellulose, or a combination of two or more thereof. In aspects, the hydroxyalkyl cellulose is hydroxypropyl cellulose. In aspects, the binder comprises hydroxyethyl cellulose. In aspects, the binder comprises hydroxypropylmethyl cellulose. In aspects, the binder comprises hydroxypropyl cellulose and hydroxyethyl cellulose. In aspects, the binder comprises hydroxypropyl cellulose and hydroxypropylmethyl cellulose. In aspects, the binder comprises hydroxyethyl cellulose and hydroxypropylmethyl cellulose. In aspects, the binder comprises hydroxypropyl cellulose, hydroxyethyl cellulose, and hydroxypropylmethyl cellulose. In aspects, the binder comprises methyl cellulose, ethyl cellulose, ethylmethyl cellulose, or a combination of two or more thereof. In aspects, the alkyl cellulose is methyl cellulose. In aspects, the binder comprises ethyl cellulose. In aspects, the binder comprises ethylmethyl cellulose. In aspects, the binder comprises methyl cellulose, ethyl cellulose, and ethylmethyl cellulose. In aspects, the binder comprises methyl cellulose and ethylmethyl cellulose. In aspects, the binder comprises ethyl cellulose and ethylmethyl cellulose. In aspects, the binder comprises methyl cellulose and ethyl cellulose.

In aspects of the pharmaceutical compositions, oral formulations, granules, tablets, capsules, powders, and beads described herein binder is present in the pharmaceutical compositions, granules, tablets, capsules, powders, and beads in an appropriate amount. In aspects, the binder is present in an amount from about 0.1 wt % to about 50 wt %; or from about 0.1 wt % to about 45 wt %; or from about 0.1 wt % to about 40 wt %; or from about 0.1 wt % to about 35 wt %; or from about 0.1 wt % to about 30 wt %. In aspects, the binder is present in an amount from about 0.5 wt % to about 25 wt %. In aspects, the binder is present in an amount from about 0.5 wt % to about 20 wt %. In aspects, the binder is in an amount from about 0.5 wt % to about 15 wt %. In aspects, the binder is in an amount from about 0.5 wt % to about 10 wt %. In aspects, the binder is in an amount from about 1 wt % to about 10 wt %. In aspects, the binder is in an amount from about 2 wt % to about 10 wt %. In aspects, the binder is in an amount from about 0.1 wt % to about 8 wt %. In aspects, the binder is in an amount from about 0.5 wt % to about 7 wt %. In aspects, the binder is in an amount from about 1 wt % to about 6 wt %. In aspects, the binder is in an amount from about 2 wt % to about 5 wt %. In aspects, the binder is in an amount from about 1 wt % to about 9 wt %. In aspects, the binder is in an amount from about 2 wt % to about 8 wt %. In aspects, the binder is in an amount from about 3 wt % to about 7 wt %. In aspects, the binder is in an amount from about 4 wt % to about 6 wt %. In aspects, the binder is in an amount from about 0.5 wt % to about 8 wt %. In aspects, the binder is in an amount from about 1 wt % to about 7 wt %. In aspects, the binder is in an amount from about 2 wt % to about 6 wt %. In aspects, the binder is in an amount from about 3 wt % to about 5 wt %. In aspects, the binder is in an amount of about 1 wt %. In aspects, the binder is in an amount of about 2 wt %. In aspects, the binder is in an amount of about 3 wt %. In aspects, the binder is in an amount of about 4 wt %. In aspects, the binder is in an amount of about 5 wt %. In aspects, the binder is in an amount of about 6 wt %. In aspects, the binder is in an amount of about 7 wt %. In aspects, the binder is in an amount of about 8 wt %.

In aspects, the pharmaceutical compositions, oral formulations, granules, tablets, capsules, powders, and beads described herein further comprise a lubricant. The lubricant can be any lubricant known in the art. In aspects, the lubricant is magnesium stearate, stearic acid, calcium stearate, sodium stearate, talcum, sodium stearyl fumarate, glyceryl behenate, boric acid, sodium benzoate, sodium oleate, sodium acetate, sodium lauryl sulfate, magnesium lauryl sulfate, or a combination of two or more thereof. In aspects, the lubricant comprises magnesium stearate. In aspects, the lubricant comprises stearic acid. In aspects, the lubricant comprises magnesium stearate and stearic acid. In aspects, the lubricant comprises magnesium stearate, calcium stearate, sodium stearate, stearic acid, or a combination of two or more thereof. In aspects, the lubricant comprises magnesium stearate, calcium stearate, sodium stearate, or a combination of two or more thereof.

In aspects of the pharmaceutical compositions, oral formulations, granules, tablets, capsules, powders, and beads described herein, the lubricant is present in the pharmaceutical compositions, granules, tablets, capsules, powders, and beads in an appropriate amount. In aspects, the lubricant is present in an amount from about 0.1 wt % to about 5 wt %. In aspects, the lubricant is in an amount from about 1 wt % to about 4 wt %. In aspects, the lubricant is in an amount from about 1.5 wt % to about 3.5 wt %. In aspects, the lubricant is in an amount from about 2 wt % to about 3 wt %. In aspects, the lubricant is in an amount from about 2 wt % to about 2.5 wt %. In aspects, the lubricant is in an amount of about 0.5 wt %. In aspects, the lubricant is in an amount of about 1 wt %. In aspects, the lubricant is in an amount of about 1.25 wt %. In aspects, the lubricant is in an amount of about 1.5 wt %. In aspects, the lubricant is in an amount of about 1.75 wt %. In aspects, the lubricant is in an amount of about 2 wt %. In aspects, the lubricant is in an amount of about 2.25 wt %. In aspects, the lubricant is in an amount of about 2.5 wt %. In aspects, the lubricant is in an amount of about 2.75 wt %. In aspects, the lubricant is in an amount of about 3 wt %. In aspects, the lubricant is in an amount of about 4 wt %. In aspects, the lubricant is in an amount of about 5 wt %.

In aspects, the pharmaceutical compositions, oral formulations, granules, tablets, capsules, powders, and beads described herein further comprise a surfactant. In aspects, the surfactant is anionic, such as ammonium lauryl sulfate, sodium lauryl sulfate, sodium lauryl ether sulfate, sodium myreth sulfate, dioctyl sodium sulfosuccinate, and the like. In aspects, the surfactant is zwitterionic, such as phospholipids, phosphatidylserine, phosphatidylethanolamine, phosphatidylcholine, and the like. In aspects, the surfactant is cationic, such as quaternary ammonium and pyridinium cationic surfactants. In aspects, the surfactant is non-ionic, such as sorbitan esters, polysorbates, poloxamers, and the like.

In aspects of the pharmaceutical compositions, oral formulations, granules, tablets, capsules, powders, and beads described herein further comprise a glidant. In aspects, the glidant is colloidal silica, silicon dioxide, talc, or a combination thereof. In aspects, the glidant is colloidal silica. In aspects, the glidant is talc.

In aspects, the disclosure provides a pharmaceutical compositions, oral formulations, tablets, capsules, granules, powders, and beads comprising: (i) a compound of Formula (III) or a pharmaceutically acceptable salt thereof having a particle size distribution with a D90 of about 10 microns or less; and (ii) a polyol, maltodextrin, microcrystalline cellulose, dicalcium phosphate, or a combination of two or more thereof. In aspects, (ii) is a polyol. In aspects, (ii) is maltodextrin. In aspects, (ii) is microcrystalline cellulose. In aspects, (ii) is a polyol and maltodextrin. In aspects, (ii) is a polyol and microcrystalline cellulose. In aspects, (ii) is maltodextrin and microcrystalline cellulose. In aspects, (ii) is a polyol, maltodextrin, and microcrystalline cellulose. In aspects, the polyol is mannitol, sorbitol, isomaltose, maltitol, lactose, sucrose, amylose, glucose, dextrose, lactitol, erythritol, arabitol, xylitol, trehalose ribitol, inositol, or a combination of two or more thereof. In aspects, (ii) is a mannitol. In aspects, (ii) is mannitol and maltodextrin. In aspects, (ii) is mannitol and microcrystalline cellulose. In aspects, (ii) comprises mannitol, maltodextrin, and microcrystalline cellulose.

In aspects, the disclosure provides pharmaceutical compositions, oral formulations, tablets, capsules, granules, powders, and beads comprising: (i) a compound of Formula (III) or a pharmaceutically acceptable salt thereof having a particle size distribution with a D90 of about 10 microns or less, and (ii) carboxymethyl cellulose, sodium starch glycolate, a crosslinked polyvinylpyrrolidone polymer, or a combination of two or more thereof. In aspects, (ii) is carboxymethyl cellulose. In aspects, the carboxymethyl cellulose is a crosslinked carboxymethyl cellulose. In aspects, the carboxymethyl cellulose is crosslinked sodium carboxymethyl cellulose. In aspects, (ii) is a polyvinylpyrrolidone polymer. In aspects, (ii) comprises carboxymethyl cellulose and a polyvinylpyrrolidone polymer.

In aspects, the disclosure provides pharmaceutical compositions, oral formulations, tablets, capsules, granules, powders, and beads comprising: (i) a compound of Formula (III) or a pharmaceutically acceptable salt thereof having a particle size distribution with a D90 of about 10 microns or less, and (ii) a hydroxyalkyl cellulose, an alkyl cellulose, corn starch, polyethylene glycol, polyethylene oxide, polyvinylpyrrolidone, or a combination of two or more thereof. In aspects, (ii) is a hydroxyalkyl cellulose. In aspects, (ii) is a hydroxypropyl cellulose. In aspects, (ii) is an alkyl cellulose. In aspects, (ii) comprises a hydroxyalkyl cellulose and an alkyl cellulose.

In aspects, the disclosure provides pharmaceutical compositions, oral formulations, tablets, capsules, granules, powders, and beads comprising: (i) a compound of Formula (III) or a pharmaceutically acceptable salt thereof having a particle size distribution with a D90 of about 10 microns or less; (ii) a polyol, maltodextrin, microcrystalline cellulose, dicalcium phosphate, or a combination of two or more thereof; and (iii) carboxymethyl cellulose, sodium starch glycolate, a crosslinked polyvinylpyrrolidone polymer, or a combination of two or more thereof. In aspects, (ii) is a polyol and (iii) is carboxymethyl cellulose. In aspects, (ii) is maltodextrin and (iii) is carboxymethyl cellulose. In aspects, (ii) is microcrystalline cellulose and (iii) is carboxymethyl cellulose. In aspects, (ii) comprises a polyol and maltodextrin and (iii) is carboxymethyl cellulose. In aspects, (ii) comprises a polyol and microcrystalline cellulose and (iii) is carboxymethyl cellulose. In aspects, (ii) comprises maltodextrin and microcrystalline cellulose and (iii) is carboxymethyl cellulose. In aspects, (ii) comprises a polyol, maltodextrin, and microcrystalline cellulose and (iii) is carboxymethyl cellulose. In aspects, the polyol is mannitol, sorbitol, isomaltose, maltitol, lactose, sucrose, amylose, glucose, dextrose, lactitol, erythritol, arabitol, xylitol, trehalose ribitol, inositol, or a combination of two or more thereof. In aspects, (ii) is a mannitol and (iii) is carboxymethyl cellulose. In aspects, (ii) comprises mannitol and maltodextrin and (iii) is carboxymethyl cellulose. In aspects, (ii) comprises mannitol and microcrystalline cellulose and (iii) is carboxymethyl cellulose. In aspects, (ii) comprises mannitol, maltodextrin, and microcrystalline cellulose and (iii) is carboxymethyl cellulose.

In aspects, the disclosure provides pharmaceutical compositions, oral formulations, tablets, capsules, granules, powders, and beads comprising: (i) a compound of Formula (III) or a pharmaceutically acceptable salt thereof having a particle size distribution with a D90 of about 10 microns or less; (ii) a polyol, maltodextrin, microcrystalline cellulose, dicalcium phosphate, or a combination of two or more thereof; and (iii) a hydroxyalkyl cellulose, an alkyl cellulose, corn starch, polyethylene glycol, polyethylene oxide, polyvinylpyrrolidone, or a combination of two or more thereof. In aspects, (ii) is a polyol, and (iii) is a hydroxyalkyl cellulose. In aspects, (ii) is maltodextrin and (iii) is a hydroxyalkyl cellulose. In aspects, (ii) comprises microcrystalline cellulose and (iii) is a hydroxyalkyl cellulose. In aspects, (ii) comprises a polyol and maltodextrin and (iii) is a hydroxyalkyl cellulose. In aspects, (ii) comprises a polyol and microcrystalline cellulose and (iii) is a hydroxyalkyl cellulose. In aspects, (ii) comprises maltodextrin and microcrystalline cellulose and (iii) is a hydroxyalkyl cellulose. In aspects, (ii) comprises a polyol, maltodextrin, and microcrystalline cellulose and (iii) is a hydroxyalkyl cellulose. In aspects, the polyol is mannitol, sorbitol, isomaltose, maltitol, lactose, sucrose, amylose, glucose, dextrose, lactitol, erythritol, arabitol, xylitol, trehalose ribitol, inositol, or a combination of two or more thereof. In aspects, (ii) is a mannitol and (iii) is a hydroxyalkyl cellulose. In aspects, (ii) comprises mannitol and maltodextrin and (iii) is a hydroxyalkyl cellulose. In aspects, (ii) comprises mannitol and microcrystalline cellulose and (iii) is a hydroxyalkyl cellulose. In aspects, (ii) comprises mannitol, maltodextrin, and microcrystalline cellulose and (iii) is a hydroxyalkyl cellulose. In aspects, the hydroxyalkyl cellulose is hydroxypropyl cellulose.

In aspects, the disclosure provides pharmaceutical compositions, oral formulations, tablets, capsules, granules, powders, and beads comprising: (i) a compound of Formula (III) or a pharmaceutically acceptable salt thereof having a particle size distribution with a D90 of about 10 microns or less, (ii) carboxymethyl cellulose, sodium starch glycolate, a crosslinked polyvinylpyrrolidone polymer, or a combination of two or more thereof; and (iii) a hydroxyalkyl cellulose, an alkyl cellulose, corn starch, polyethylene glycol, polyethylene oxide, polyvinylpyrrolidone, or a combination of two or more thereof. In aspects, (ii) is carboxymethyl cellulose, and (iii) is a hydroxyalkyl cellulose. In aspects, the carboxymethyl cellulose is a crosslinked carboxymethyl cellulose. In aspects, the carboxymethyl cellulose is crosslinked sodium carboxymethyl cellulose. In aspects, (ii) is a polyvinylpyrrolidone polymer and (iii) is a hydroxyalkyl cellulose. In aspects, (ii) comprises carboxymethyl cellulose and a polyvinylpyrrolidone polymer and (iii) is a hydroxyalkyl cellulose. In aspects, the hydroxyalkyl cellulose is hydroxypropyl cellulose.

In aspects, the disclosure provides pharmaceutical compositions, oral formulations, tablets, capsules, granules, powders, and beads comprising: (i) a compound of Formula (III) or a pharmaceutically acceptable salt thereof having a particle size distribution with a D90 of about 10 microns or less; (ii) a polyol, maltodextrin, microcrystalline cellulose, dicalcium phosphate, or a combination of two or more thereof; (iii) carboxymethyl cellulose, sodium starch glycolate, a crosslinked polyvinylpyrrolidone polymer, or a combination of two or more thereof; and (iv) a hydroxyalkyl cellulose, an alkyl cellulose, corn starch, polyethylene glycol, polyethylene oxide, polyvinylpyrrolidone, or a combination of two or more thereof. In aspects, (ii) is a polyol, (iii) is carboxymethyl cellulose, and (iv) is a hydroxyalkyl cellulose. In aspects, (ii) is maltodextrin, (iii) is carboxymethyl cellulose, and (iv) is a hydroxyalkyl cellulose. In aspects, (ii) is microcrystalline cellulose, (iii) is carboxymethyl cellulose, and (iv) is a hydroxyalkyl cellulose. In aspects, (ii) comprises a polyol and maltodextrin, (iii) is carboxymethyl cellulose, and (iv) is a hydroxyalkyl cellulose. In aspects, (ii) comprises a polyol and microcrystalline cellulose, (iii) is carboxymethyl cellulose, and (iv) is a hydroxyalkyl cellulose. In aspects, (ii) comprises maltodextrin and microcrystalline cellulose, (iii) is carboxymethyl cellulose, and (iv) is a hydroxyalkyl cellulose. In aspects, (ii) comprises a polyol, maltodextrin, and microcrystalline cellulose, (iii) is carboxymethyl cellulose, and (iv) is a hydroxyalkyl cellulose. In aspects, the polyol is mannitol, sorbitol, isomaltose, maltitol, lactose, sucrose, amylose, glucose, dextrose, lactitol, erythritol, arabitol, xylitol, trehalose ribitol, inositol, or a combination of two or more thereof. In aspects, the hydroxyalkyl cellulose is hydroxypropyl cellulose, hydroxyethyl cellulose, hydroxypropylmethyl cellulose, or a combination of two or more thereof. In aspects, (ii) is a mannitol, (iii) is a crosslinked carboxymethyl cellulose, and (iv) is hydroxypropyl cellulose. In aspects, (ii) comprises mannitol and maltodextrin, (iii) is a crosslinked carboxymethyl cellulose, and (iv) is hydroxypropyl cellulose. In aspects, (ii) comprises mannitol and microcrystalline cellulose, (iii) is a crosslinked carboxymethyl cellulose, and (iv) is hydroxypropyl cellulose. In aspects, (ii) comprises mannitol, maltodextrin, and microcrystalline cellulose, (iii) is a crosslinked carboxymethyl cellulose, and (iv) is hydroxypropyl cellulose.

In aspects, the disclosure provides pharmaceutical compositions, oral formulations, tablets, capsules, granules, powders, and beads comprising: (i) about 25 wt % to about 35 wt % of an adenosine A2A receptor antagonist or a pharmaceutically acceptable salt thereof; (ii) about 50 wt % to about 70 wt % of a filler; and (iii) about 1 wt % to about 10 wt % of a disintegrant. In aspects, the pharmaceutical compositions further comprise about 1 wt % to about 10 wt % of a binder.

In aspects, the disclosure provides pharmaceutical compositions, oral formulations, tablets, capsules, granules, powders, and beads comprising: (i) about 25 wt % to about 35 wt % of a compound of Formula (III) or a pharmaceutically acceptable salt thereof; (ii) about 40 wt % to about 60 wt % of mannitol; (iii) about 5 wt % to about 20 wt % of microcrystalline cellulose; and (iv) about 1 wt % to about 10 wt % of crosslinked sodium carboxymethyl cellulose. In aspects, the pharmaceutical compositions further comprise about 1 wt % to about 10 wt % of hydroxypropyl cellulose.

In aspects, the disclosure provides pharmaceutical compositions, oral formulations, tablets, capsules, granules, powders, and beads comprising: (i) about 25 wt % to about 35 wt % of a compound of Formula (III) or a pharmaceutically acceptable salt thereof; (ii) about 45 wt % to about 55 wt % of mannitol; (iii) about 10 wt % to about 15 wt % of microcrystalline cellulose; and (iv) about 4 wt % to about 8 wt % of crosslinked sodium carboxymethyl cellulose. In aspects, the pharmaceutical compositions further comprise about 1 wt % to about 8 wt % of hydroxypropyl cellulose.

In aspects, the disclosure provides pharmaceutical compositions, oral formulations, tablets, capsules, granules, powders, and beads comprising: (i) about 20 wt % to about 30 wt % of a compound of Formula (III) or a pharmaceutically acceptable salt thereof; (ii) about 30 wt % to about 50 wt % of mannitol; (iii) about 15 wt % to about 30 wt % of microcrystalline cellulose; and (iv) about 1 wt % to about 15 wt % of crosslinked sodium carboxymethyl cellulose. In aspects, the pharmaceutical compositions further comprise about 1 wt % to about 10 wt % of hydroxypropyl cellulose. In aspects, the mannitol comprises a spray-dried mannitol and a crystalline mannitol in a weight ratio from about 1:1.5 to about 1:2.5.

In aspects, the disclosure provides pharmaceutical compositions, oral formulations, tablets, capsules, granules, powders, and beads comprising: (i) about 23 wt % to about 27 wt % of a compound of Formula (III) or a pharmaceutically acceptable salt thereof; (ii) about 37 wt % to about 40 wt % of mannitol; (iii) about 21 wt % to about 24 wt % of microcrystalline cellulose; and (iv) about 5 wt % to about 10 wt % of crosslinked sodium carboxymethyl cellulose. In aspects, the pharmaceutical compositions further comprise about 2 wt % to about 6 wt % of hydroxypropyl cellulose. In aspects, the mannitol comprises a spray-dried mannitol and a crystalline mannitol in a weight ratio from about 1:1.5 to about 1:2.5.

In aspects, the disclosure provides pharmaceutical compositions, oral formulations, tablets, capsules, granules, powders, and beads comprising: (i) about 24 wt % to about 26 wt % of a compound of Formula (III) or a pharmaceutically acceptable salt thereof; (ii) about 38 wt % to about 39 wt % of mannitol; (iii) about 22 wt % to about 23 wt % of microcrystalline cellulose; and (iv) about 7 wt % to about 9 wt % of crosslinked sodium carboxymethyl cellulose. In aspects, the pharmaceutical compositions further comprise about 3 wt % to about 5 wt % of hydroxypropyl cellulose. In aspects, the mannitol comprises a spray-dried mannitol and a crystalline mannitol in a weight ratio from about 1:1.5 to about 1:2.5.

In aspects, the disclosure provides pharmaceutical compositions, oral formulations, tablets, capsules, granules, powders, and beads comprising: (i) about 25 wt % of a compound of Formula (III) or a pharmaceutically acceptable salt thereof; (ii) about 38.25 wt % of mannitol; (iii) about 22.5 wt % of microcrystalline cellulose; and (iv) about 8 wt % of crosslinked sodium carboxymethyl cellulose. In aspects, the pharmaceutical compositions further comprise about 4 wt % of hydroxypropyl cellulose. In aspects, the mannitol comprises a spray-dried mannitol and a crystalline mannitol in a weight ratio from about 1:1.5 to about 1:2.5.

In aspects, the disclosure provides a bioequivalent formulation of the pharmaceutical compositions, oral formulations, granules, tablets, powders, oral formulations, and beads described herein. In aspects, the disclosure provides Pharmaceutical Composition No. 6. In aspects, the disclosure provides Pharmaceutical Composition No. 6 as shown in Table 11A or a bioequivalent formulation thereof. In aspects, the disclosure provides Pharmaceutical Composition No. 6 as shown in Table 11B or a bioequivalent formulation thereof. In aspects, the disclosure provides Pharmaceutical Composition No. 5. In aspects, the disclosure provides Pharmaceutical Composition No. 5 as shown in Table 9A or a bioequivalent formulation thereof. In aspects, the disclosure provides Pharmaceutical Composition No. 5 as shown in Table 9B or a bioequivalent formulation thereof. In aspects, the disclosure provides Pharmaceutical Composition No. 4. In aspects, the disclosure provides Pharmaceutical Composition No. 3 or a bioequivalent formulation thereof. In aspects, the disclosure provides Pharmaceutical Composition No. 2 or a bioequivalent formulation thereof. In aspects, the disclosure provides Pharmaceutical Composition No. 1 or a bioequivalent formulation thereof.

In embodiment of the compositions provided herein, including pharmaceutical compositions and oral formulations (e.g., tablets, capsules, granules, powders, and beads), the composition includes no other active pharmaceutical ingredients other than one or more A2A receptor antagonists. In aspect of the compositions provided herein, including pharmaceutical compositions, oral formulations (e.g., tablets, capsules, granules, powders, and beads), the composition includes only a single type of A2A receptor antagonist. In aspects of the compositions provided herein, including pharmaceutical compositions and oral formulations (e.g., tablets, capsules, granules, powders, and beads), the composition include only a single type of A2A receptor antagonist and no other active pharmaceutical ingredient. In aspects of the compositions provided herein, including pharmaceutical compositions and oral formulations (e.g., tablets, capsules, granules, powders, and beads), the composition includes only a single type of A2A receptor antagonist and no pharmaceutical excipients or other active pharmaceutical ingredients.

Oral Formulations

In aspects, the pharmaceutical compositions described herein are oral formulations. Oral formulations include tablets, pills, powder, sachets, stickpacks, film, dragees, capsules, wafers, films, liquids, lozenges, gels, syrups, slurries, suspensions, etc., suitable for ingestion by the patient. Solid oral formulations include powders, tablets, granules, beads, capsules, films, wafers, chewable formulations, and dispersible granules. Liquid oral formulations include solutions, suspensions, and emulsions. Other oral dosage formulations include oral mucosal formulations, such as sublingual or buccal formulations, such as tablets, films or wafers.

In aspects, the oral formulation is a tablet as described herein. In aspects, the tablet is a compressed tablet. In aspects, the tablet is encapsulated within an outer layer. In aspects, the tablet is encapsulated within an outer enteric layer. In aspects, the tablet is a rapidly-disintegrating tablet. In aspects, the tablet is a sublingual tablet. In aspects, the tablet is a buccal tablet. In aspects, the tablet is a rapidly-disintegrating sublingual tablet. In aspects, the tablet is a rapidly-disintegrating buccal tablet. In aspects, the tablet is formed by compressing the pharmaceutical composition described herein. In aspects, the tablet is formed by compressing the granules described herein. In aspects, the tablet is formed by compressing the granules described herein, wherein the granules have an outer coating layer, and wherein the tablet optionally further comprises an outer coating layer. In aspects, the tablet is formed by compressing the pharmaceutical composition described herein. In aspects, the tablet is formed by compressing the powders described herein. In aspects, the tablet is formed by compressing the beads described herein. In aspects, the tablet is formed by compressing the beads described herein, wherein the beads have an outer coating layer, and wherein the tablet optionally further comprises an outer coating layer. In aspects, the outer coating layer comprises an enteric coating.

In aspects, the oral formulation is a capsule. In aspects, the capsule comprises the pharmaceutical compositions described herein encapsulated within a capsule shell, wherein the capsule shell is optionally further encapsulated within an outer coating layer. In aspects, the capsule comprises the granules described herein encapsulated within a capsule shell, wherein the capsule shell is optionally further encapsulated within an outer coating layer. In aspects, the capsule comprises the granules described herein encapsulated within a capsule shell, wherein the granules comprise an outer coating layer, and wherein the capsule shell is optionally further encapsulated within an outer coating layer. In aspects, the capsule comprises the beads described herein encapsulated within a capsule shell, wherein the beads comprise an outer coating layer, and wherein the capsule shell is optionally further encapsulated within an outer coating layer. In aspects, the capsule comprises the powders described herein encapsulated within a capsule shell, wherein the capsule shell is optionally further encapsulated within an outer coating layer. In aspects, the oral formulation is a solid capsule. In aspects, the capsule is a rapidly-disintegrating capsule. In aspects, the outer coating layer comprises an enteric coating. In aspects, the capsule shell comprises an enteric polymer.

In aspects, the oral formulation is a granule, where the granule comprises the pharmaceutical compositions described herein. In aspects, the granules comprise a coating layer. In aspects, a plurality of granules comprise a coating layer and a plurality of granules do not comprise an coating layer. In aspects, the granule is sprinkled on or in food or liquid or given directly for oral administration.

In aspects, the oral formulation is a powder, where the powder comprises the pharmaceutical compositions described herein. In aspects, the oral formulation is a reconstitutable powder. A reconstitutable powder can be added to a liquid for ingestion, where the powder dissolves in the liquid or the powder forms a suspension in the liquid. In aspects, the powder is sprinkled on or in food for oral administration.

In aspects, the disclosure provides sachets containing the pharmaceutical compositions described herein. In aspects, the disclosure provides sachets containing the granules described herein. In aspects, the disclosure provides sachets containing the powder described herein. In aspects, the disclosure provides sachets containing the beads described herein. A sachet is a useful packaging material where the contents are intended to be sprinkled in food or added to a liquid.

In embodiments, the disclosure provides stick packs containing the pharmaceutical compositions described herein. In aspects, the disclosure provides stick packs containing the granules described herein. In aspects, the disclosure provides stick packs containing the powder described herein. In aspects, the disclosure provides stick packs containing the beads described herein. A stick pack is a useful packaging material where the contents are intended to be sprinkled in food or added to a liquid.

In embodiments, the oral formulations described herein, including the tablets, capsules, granules, and beads comprise an coating. In aspects, the coating surrounds the formulation, i.e., the coating forms a layer where the formulation is enclosed within (surrounded by) the layer. In aspects, the coating partially surrounds the formulation. In aspects, the oral formulation is a tablet comprising a coating. In aspects, the oral formulation is a compressed tablet comprising a coating. In aspects, the oral formulation is a capsule comprising a coating. In aspects, the oral formulation comprises granules surrounded by a coating. In aspects, the oral formulation comprises beads surrounded by a coating. In aspects, the coating is an enteric coating.

In aspects, the oral formulations described herein, including the tablets, capsules, granules, powders, and beads comprise a dose of the adenosine A2A receptor antagonist from about 1 mg to about 1,000 mg. In aspects, the dose of the adenosine A2A receptor antagonist is from about 1 mg to about 900 mg. In aspects, the dose of the adenosine A2A receptor antagonist from about 1 mg to about 800 mg. In aspects, the dose of the adenosine A2A receptor antagonist is from about 1 mg to about 700 mg. In aspects, the dose of the adenosine A2A receptor antagonist is from about 1 mg to about 600 mg. In aspects, the dose of the adenosine A2A receptor antagonist is from about 1 mg to about 500 mg. In aspects, the dose of the adenosine A2A receptor antagonist is from about 1 mg to about 400 mg.

In aspects, the oral formulations, such as tablets and capsules, comprise a dose of the adenosine A2A receptor antagonist from about 1 mg to about 50 mg. In aspects, the oral formulations, such as tablets and capsules, comprise a dose of the adenosine A2A receptor antagonist from about 5 mg to about 40 mg. In aspects, the oral formulations, such as tablets and capsules, comprise a dose of the adenosine A2A receptor antagonist from about 5 mg to about 30 mg. In aspects, the oral formulations, such as tablets and capsules, comprise a dose of the adenosine A2A receptor antagonist from about 5 mg to about 20 mg. In aspects, the oral formulations, such as tablets and capsules, comprise a dose of the adenosine A2A receptor antagonist from about 5 mg to about 10 mg. In aspects, the oral formulations, such as tablets and capsules, comprise a dose of the adenosine A2A receptor antagonist of about 5 mg. In aspects, the oral formulations, such as tablets and capsules, comprise a dose of the adenosine A2A receptor antagonist of about 10 mg. In aspects, the oral formulations, such as tablets and capsules, comprise a dose of the adenosine A2A receptor antagonist of about 20 mg. In aspects, the oral formulations, such as tablets and capsules, comprise a dose of the adenosine A2A receptor antagonist of about 25 mg.

In aspects, the oral formulations, such as tablets and capsules, comprise a dose of the adenosine A2A receptor antagonist from about 20 mg to about 100 mg. In aspects, the oral formulations, such as tablets and capsules, comprise a dose of the adenosine A2A receptor antagonist from about 25 mg to about 75 mg. In aspects, the oral formulations, such as tablets and capsules, comprise a dose of the adenosine A2A receptor antagonist from about 30 mg to about 70 mg. In aspects, the oral formulations, such as tablets and capsules, comprise a dose of the adenosine A2A receptor antagonist from about 40 mg to about 60 mg. In aspects, the oral formulations, such as tablets and capsules, comprise a dose of the adenosine A2A receptor antagonist from about 45 mg to about 55 mg. In aspects, the oral formulations, such as tablets and capsules, comprise a dose of the adenosine A2A receptor antagonist of about 50 mg.

In aspects, the oral formulations, such as tablets and capsules, comprise a dose of the adenosine A2A receptor antagonist from about 50 mg to about 150 mg. In aspects, the oral formulations, such as tablets and capsules, comprise a dose of the adenosine A2A receptor antagonist from about 75 mg to about 125 mg. In aspects, the oral formulations, such as tablets and capsules, comprise a dose of the adenosine A2A receptor antagonist from about 80 mg to about 120 mg. In aspects, the oral formulations, such as tablets and capsules, comprise a dose of the adenosine A2A receptor antagonist from about 85 mg to about 115 mg. In aspects, the oral formulations, such as tablets and capsules, comprise a dose of the adenosine A2A receptor antagonist from about 90 mg to about 110 mg. In aspects, the oral formulations, such as tablets and capsules, comprise a dose of the adenosine A2A receptor antagonist from about 95 mg to about 105 mg. In aspects, the oral formulations, such as tablets and capsules, comprise a dose of the adenosine A2A receptor antagonist of about 100 mg.

In aspects, the oral formulations, such as tablets and capsules, comprise a dose of the adenosine A2A receptor antagonist from about 100 mg to about 200 mg. In aspects, the oral formulations, such as tablets and capsules, comprise a dose of the adenosine A2A receptor antagonist from about 110 mg to about 190 mg. In aspects, the oral formulations, such as tablets and capsules, comprise a dose of the adenosine A2A receptor antagonist from about 120 mg to about 180 mg. In aspects, the oral formulations, such as tablets and capsules, comprise a dose of the adenosine A2A receptor antagonist from about 130 mg to about 170 mg. In aspects, the oral formulations, such as tablets and capsules, comprise a dose of the adenosine A2A receptor antagonist from about 140 mg to about 160 mg. In aspects, the oral formulations, such as tablets and capsules, comprise a dose of the adenosine A2A receptor antagonist of about 150 mg.

In aspects, the oral formulations, such as tablets and capsules, comprise a dose of the adenosine A2A receptor antagonist from about 150 mg to about 250 mg. In aspects, the oral formulations, such as tablets and capsules, comprise a dose of the adenosine A2A receptor antagonist from about 170 mg to about 230 mg. In aspects, the oral formulations, such as tablets and capsules, comprise a dose of the adenosine A2A receptor antagonist from about 180 mg to about 220 mg. In aspects, the oral formulations, such as tablets and capsules, comprise a dose of the adenosine A2A receptor antagonist from about 185 mg to about 215 mg. In aspects, the oral formulations, such as tablets and capsules, comprise a dose of the adenosine A2A receptor antagonist from about 190 mg to about 210 mg. In aspects, the oral formulations, such as tablets and capsules, comprise a dose of the adenosine A2A receptor antagonist from about 195 mg to about 205 mg. In aspects, the oral formulations, such as tablets and capsules, comprise a dose of the adenosine A2A receptor antagonist of about 200 mg.

In aspects, the oral formulations, such as tablets and capsules, comprise a dose of the adenosine A2A receptor antagonist from about 200 mg to about 300 mg. In aspects, the oral formulations, such as tablets and capsules, comprise a dose of the adenosine A2A receptor antagonist from about 210 mg to about 290 mg. In aspects, the oral formulations, such as tablets and capsules, comprise a dose of the adenosine A2A receptor antagonist from about 220 mg to about 280 mg. In aspects, the oral formulations, such as tablets and capsules, comprise a dose of the adenosine A2A receptor antagonist from about 230 mg to about 270 mg. In aspects, the oral formulations, such as tablets and capsules, comprise a dose of the adenosine A2A receptor antagonist from about 240 mg to about 260 mg. In aspects, the oral formulations, such as tablets and capsules, comprise a dose of the adenosine A2A receptor antagonist of about 250 mg.

In aspects, the oral formulations, such as tablets and capsules, comprise a dose of the adenosine A2A receptor antagonist from about 250 mg to about 350 mg. In aspects, the oral formulations, such as tablets and capsules, comprise a dose of the adenosine A2A receptor antagonist from about 270 mg to about 330 mg. In aspects, the oral formulations, such as tablets and capsules, comprise a dose of the adenosine A2A receptor antagonist from about 280 mg to about 320 mg. In aspects, the oral formulations, such as tablets and capsules, comprise a dose of the adenosine A2A receptor antagonist from about 285 mg to about 315 mg. In aspects, the oral formulations, such as tablets and capsules, comprise a dose of the adenosine A2A receptor antagonist from about 290 mg to about 310 mg. In aspects, the oral formulations, such as tablets and capsules, comprise a dose of the adenosine A2A receptor antagonist from about 295 mg to about 305 mg. In aspects, the oral formulations, such as tablets and capsules, comprise a dose of the adenosine A2A receptor antagonist of about 300 mg.

In aspects, the oral formulations, such as tablets and capsules, comprise a dose of the adenosine A2A receptor antagonist from about 300 mg to about 400 mg. In aspects, the oral formulations, such as tablets and capsules, comprise a dose of the adenosine A2A receptor antagonist from about 310 mg to about 390 mg. In aspects, the oral formulations, such as tablets and capsules, comprise a dose of the adenosine A2A receptor antagonist from about 320 mg to about 380 mg. In aspects, the oral formulations, such as tablets and capsules, comprise a dose of the adenosine A2A receptor antagonist from about 330 mg to about 370 mg. In aspects, the oral formulations, such as tablets and capsules, comprise a dose of the adenosine A2A receptor antagonist from about 340 mg to about 360 mg. In aspects, the oral formulations, such as tablets and capsules, comprise a dose of the adenosine A2A receptor antagonist of about 350 mg.

In aspects, the oral formulations, such as tablets and capsules, comprise a dose of the adenosine A2A receptor antagonist from about 350 mg to about 450 mg. In aspects, the oral formulations, such as tablets and capsules, comprise a dose of the adenosine A2A receptor antagonist from about 370 mg to about 430 mg. In aspects, the oral formulations, such as tablets and capsules, comprise a dose of the adenosine A2A receptor antagonist from about 380 mg to about 420 mg. In aspects, the oral formulations, such as tablets and capsules, comprise a dose of the adenosine A2A receptor antagonist from about 385 mg to about 415 mg. In aspects, the oral formulations, such as tablets and capsules, comprise a dose of the adenosine A2A receptor antagonist from about 390 mg to about 410 mg. In aspects, the oral formulations, such as tablets and capsules, comprise a dose of the adenosine A2A receptor antagonist from about 395 mg to about 405 mg. In aspects, the oral formulations, such as tablets and capsules, comprise a dose of the adenosine A2A receptor antagonist of about 400 mg.

In aspects, the oral formulations, such as tablets and capsules, comprise a dose of the adenosine A2A receptor antagonist from about 400 mg to about 500 mg. In aspects, the oral formulations, such as tablets and capsules, comprise a dose of the adenosine A2A receptor antagonist from about 410 mg to about 490 mg. In aspects, the oral formulations, such as tablets and capsules, comprise a dose of the adenosine A2A receptor antagonist from about 420 mg to about 480 mg. In aspects, the oral formulations, such as tablets and capsules, comprise a dose of the adenosine A2A receptor antagonist from about 430 mg to about 470 mg. In aspects, the oral formulations, such as tablets and capsules, comprise a dose of the adenosine A2A receptor antagonist from about 440 mg to about 460 mg. In aspects, the oral formulations, such as tablets and capsules, comprise a dose of the adenosine A2A receptor antagonist of about 450 mg.

In aspects, the oral formulations, such as tablets and capsules, comprise a dose of the adenosine A2A receptor antagonist from about 450 mg to about 550 mg. In aspects, the oral formulations, such as tablets and capsules, comprise a dose of the adenosine A2A receptor antagonist from about 470 mg to about 530 mg. In aspects, the oral formulations, such as tablets and capsules, comprise a dose of the adenosine A2A receptor antagonist from about 480 mg to about 520 mg. In aspects, the oral formulations, such as tablets and capsules, comprise a dose of the adenosine A2A receptor antagonist from about 485 mg to about 515 mg. In aspects, the oral formulations, such as tablets and capsules, comprise a dose of the adenosine A2A receptor antagonist from about 490 mg to about 510 mg. In aspects, the oral formulations, such as tablets and capsules, comprise a dose of the adenosine A2A receptor antagonist from about 495 mg to about 505 mg. In aspects, the oral formulations, such as tablets and capsules, comprise a dose of the adenosine A2A receptor antagonist of about 500 mg.

In aspects, the oral formulations, such as tablets and capsules, comprise a dose of the adenosine A2A receptor antagonist from about 500 mg to about 600 mg. In aspects, the oral formulations, such as tablets and capsules, comprise a dose of the adenosine A2A receptor antagonist from about 510 mg to about 590 mg. In aspects, the oral formulations, such as tablets and capsules, comprise a dose of the adenosine A2A receptor antagonist from about 520 mg to about 580 mg. In aspects, the oral formulations, such as tablets and capsules, comprise a dose of the adenosine A2A receptor antagonist from about 530 mg to about 570 mg. In aspects, the oral formulations, such as tablets and capsules, comprise a dose of the adenosine A2A receptor antagonist from about 540 mg to about 560 mg. In aspects, the oral formulations, such as tablets and capsules, comprise a dose of the adenosine A2A receptor antagonist of about 550 mg.

In aspects, the oral formulations, such as tablets and capsules, comprise a dose of the adenosine A2A receptor antagonist from about 550 mg to about 650 mg. In aspects, the oral formulations, such as tablets and capsules, comprise a dose of the adenosine A2A receptor antagonist from about 570 mg to about 630 mg. In aspects, the oral formulations, such as tablets and capsules, comprise a dose of the adenosine A2A receptor antagonist from about 580 mg to about 620 mg. In aspects, the oral formulations, such as tablets and capsules, comprise a dose of the adenosine A2A receptor antagonist from about 585 mg to about 615 mg. In aspects, the oral formulations, such as tablets and capsules, comprise a dose of the adenosine A2A receptor antagonist from about 590 mg to about 610 mg. In aspects, the oral formulations, such as tablets and capsules, comprise a dose of the adenosine A2A receptor antagonist from about 595 mg to about 605 mg. In aspects, the oral formulations, such as tablets and capsules, comprise a dose of the adenosine A2A receptor antagonist of about 600 mg.

Properties

The pharmaceutical compositions (e.g., oral formulations, tablets, capsules, beads, granules, powders) described herein have excellent chemical properties (e.g., stability, dissolution, disintegration) and biological properties (e.g., pharmacokinetic properties).

In embodiments, the pharmaceutical compositions (e.g., oral formulations, tablets, beads, capsules, granules) are rapidly-dissolving, as measured by US Pharmacopeia (USP), Chapter <711>, Type II (Paddle) Dissolution Apparatus. In aspects, the dissolution is at least 55% in 60 minutes. In aspects, the dissolution is at least 60% in 60 minutes. In aspects, the dissolution is at least 65% in 60 minutes. In aspects, the dissolution is at least 70% in 60 minutes. In aspects, the dissolution is at least 75% in 60 minutes. In aspects, the dissolution is at least 80% in 60 minutes. In aspects, the dissolution is at least 81% in 60 minutes. In aspects, the dissolution is at least 82% in 60 minutes. In aspects, the dissolution is at least 83% in 60 minutes. In aspects, the dissolution is at least 84% in 60 minutes. In aspects, the dissolution is at least 85% in 60 minutes. In aspects, the dissolution is at least 86% in 60 minutes. In aspects, the dissolution is at least 87% in 60 minutes. In aspects, the dissolution is at least 88% in 60 minutes. In aspects, the dissolution is at least 90% in 60 minutes. In aspects, the dissolution is at least 95% in 60 minutes. "Dissolution" or "dissolution rate" described herein is measured by US Pharmacopeia (USP), Chapter <711>, Type II (Paddle) Dissolution Apparatus.

In embodiments, the dissolution is at least 55% in 30 minutes, as measured by US Pharmacopeia (USP), Chapter <711>, Type II (Paddle) Dissolution Apparatus. In aspects, the dissolution is at least 60% in 30 minutes. In aspects, the dissolution is at least 65% in 30 minutes. In aspects, the dissolution is at least 70% in 30 minutes. In aspects, the dissolution is at least 75% in 30 minutes. In aspects, the dissolution is at least 80% in 30 minutes. In aspects, the dissolution is at least 85% in 30 minutes. In aspects, the dissolution is at least 90% in 30 minutes. In aspects, the dissolution is at least 95% in 30 minutes. "Dissolution" or "dissolution rate" described herein is measured by US Pharmacopeia (USP), Chapter <711>, Type II (Paddle) Dissolution Apparatus.

In embodiments, the dissolution is at least 50% in 10 minutes, as measured by US Pharmacopeia (USP), Chapter <711>, Type II (Paddle) Dissolution Apparatus. In aspects, the dissolution is at least 55% in 10 minutes. In aspects, the dissolution is at least 60% in 10 minutes. In aspects, the dissolution is at least 65% in 10 minutes. In aspects, the dissolution is at least 70% in 10 minutes. In aspects, the dissolution is at least 75% in 10 minutes. In aspects, the dissolution is at least 80% in 10 minutes. In aspects, the dissolution is at least 85% in 10 minutes. In aspects, the dissolution is at least 90% in 10 minutes. "Dissolution" or "dissolution rate" described herein is measured by US Pharmacopeia (USP), Chapter <711>, Type II (Paddle) Dissolution Apparatus.

In embodiments, the pharmaceutical compositions (e.g., oral formulations, tablets, beads, capsules, granules) are rapidly-disintegrating, as measured by US Pharmacopeia (USP), Chapter <701>, Disintegration Test. In aspects, the pharmaceutical compositions have a disintegration time of about 30 minutes or less. In aspects, the pharmaceutical compositions have a disintegration time of about 25 minutes or less. In aspects, the pharmaceutical compositions have a disintegration time of about 20 minutes or less. In aspects, the pharmaceutical compositions have a disintegration time of about 19 minutes or less. In aspects, the disintegration time is about 18 minutes or less. In aspects, the disintegration time is about 17 minutes or less. In aspects, the disintegration time is about 16 minutes or less. In aspects, the disintegration time is about 15 minutes or less. In aspects, the disintegration time is about 14 minutes or less. In aspects, the disintegration time is about 13 minutes or less. In aspects, the disintegration time is about 12 minutes or less. In aspects, the disintegration time is about 11 minutes or less. In aspects, the disintegration time is about 10 minutes or less. In aspects, the disintegration time is about 9 minutes or less. In aspects, the disintegration time is about 8 minutes or less. In aspects, the disintegration time is about 7 minutes or less. In aspects, the disintegration time is about 6 minutes or less. In aspects, the disintegration time is about 5 minutes or less. In aspects, the disintegration time is about 4 minutes or less. In aspects, the disintegration time is about 3 minutes or less. In aspects, the disintegration time is about 2 minutes or less. In aspects, the disintegration time is about 1 minutes or less. "Disintegration" or "disintegration time" or "disintegration rate" is measured by US Pharmacopeia (USP), Chapter <701>, Disintegration Test.

In embodiments, the pharmaceutical compositions (e.g., oral formulations, tablets, beads, capsules, granules) described herein have a total impurity level of less than 3% under the following conditions: closed storage for 4 weeks at 40° C., 75% relative humidity, as measured by high performance liquid chromatography followed by ultraviolet spectroscopy (HPLC-UV). In aspects, the impurity level is less than 2.5%. In aspects, the impurity level is less than 2%. In aspects, the impurity level is less than 1.9%. In aspects, the impurity level is less than 1.8%. In aspects, the impurity level is less than 1.7%. In aspects, the impurity level is less than 1.6%. In aspects, the impurity level is less than 1.5%. In aspects, the impurity level is less than 1.4%. In aspects, the impurity level is less than 1.3%. In aspects, the impurity level is less than 1.2%. In aspects, the impurity level is less than 1.1%. In aspects, the impurity level is less than 1%. In aspects, the impurity level is less than 0.9%. In aspects, the impurity level is less than 0.8%. In aspects, the impurity level is less than 0.7%. In aspects, the impurity level is less than 0.6%. In aspects, the impurity level is less than 0.5%. In aspects, the impurity level is less than 0.4%. In aspects, the total impurity level is from about 0.5% to less than 2.0%. In aspects, the total impurity level is from about 0.5% to less than 1.5%. In aspects, the total impurity level is from about 0.5% to less than 1.4%. In aspects, the total impurity level is from about 0.5% to less than 1.3%. In aspects, the total impurity level is from about 0.5% to less than 1.2%. In aspects, the total impurity level is from about 0.5% to less than 1.1%. In aspects, the total impurity level is from about 0.5% to less than 1.0%. In aspects, the total impurity level is from about 0.5% to less than 0.9%.

In embodiments, the pharmaceutical compositions (e.g., oral formulations, tablets, beads, capsules, granules) described herein have a total impurity level of less than 3% under any of the following conditions: (i) closed storage for 6 months at 40° C., 75% relative humidity, with or without a desiccant, as measured by high performance liquid chromatography followed by ultraviolet spectroscopy (HPLC-UV); (ii) closed storage for 6 months at 25° C., 60% relative humidity, with or without a desiccant, as measured by HPLC-UV; (iii) closed storage for 3 months at 40° C., 75% relative humidity, with or without a desiccant, as measured by HPLC-UV; or (iv) closed storage for 3 months at 25° C., 60% relative humidity, with or without a desiccant, as measured by HPLC-UV. In aspects, the impurity level is less than 2.5%. In aspects, the impurity level is less than 2%. In aspects, the impurity level is less than 1.9%. In aspects, the impurity level is less than 1.8%. In aspects, the impurity level is less than 1.7%. In aspects, the impurity level is less than 1.6%. In aspects, the impurity level is less than 1.5%. In aspects, the impurity level is less than 1.4%. In aspects, the impurity level is less than 1.3%. In aspects, the impurity level is less than 1.2%. In aspects, the impurity level is less than 1.1%. In aspects, the impurity level is less than 1%. In aspects, the impurity level is less than 0.9%. In aspects, the impurity level is less than 0.8%. In aspects, the impurity level is less than 0.7%. In aspects, the impurity level is less than 0.6%. In aspects, the impurity level is less than 0.5%. In aspects, the impurity level is less than 0.4%. In aspects, the total impurity level is from about 0.5% to less than 2.0%. In aspects, the total impurity level is from about 0.5% to less than 1.5%. In aspects, the total impurity level is from about 0.5% to less than 1.4%. In aspects, the total impurity level is from about 0.5% to less than 1.3%. In aspects, the total impurity level is from about 0.5% to less than 1.2%. In aspects, the total impurity level is from about 0.5% to less than 1.1%. In aspects, the total impurity level is from about 0.5% to less than 1.0%. In aspects, the total impurity level is from about 0.5% to less than 0.9%.

In embodiments, the pharmaceutical compositions (e.g., oral formulations, tablets, beads, capsules, granules) described herein have an assay % label claim (LC) from about 90% to about 110%. In aspects, the % LC is from about 91% to about 109%. In aspects, the % LC is from about 92% to about 108%. In aspects, the % LC is from about 93% to about 107%. In aspects, the % LC is from about 94% to about 106%. In aspects, the % LC is from about 95% to about 105%. In aspects, the % LC is from about 96% to about 104%. In aspects, the % LC is from about 97% to about 103%. In aspects, the % LC is from about 97% to about 103%. In aspects, the % LC is from about 98% to about 102%. In aspects, the % LC is from about 99% to about 101%.

Methods of Treatment

In embodiments, the disclosure provides methods of treating cancer in patients by administering to the patients therapeutically effective amounts of the pharmaceutical compositions, oral formulations, granules, beads, tablets, capsules, powders, or oral formulations described herein. The methods are effective to treat any cancer, particularly cancers that are modulated by the adenosine A2A receptor. In aspects, that pharmaceutical compositions, granules, beads, or oral formulations are for treating metastatic cancer. In aspects, the methods are for treating lung cancer, melanoma, renal cell cancer, breast cancer, colorectal cancer, bladder cancer, prostate cancer, or a head and neck cancer. In aspects, the methods are for treating non-small cell lung cancer, malignant melanoma, renal cell cancer, triple negative breast cancer, colorectal cancer, or bladder cancer. In aspects, the methods are for treating lung cancer. In aspects, the methods are for treating non-small cell lung cancer. In aspects, the methods are for treating melanoma. In aspects, the methods are for treating malignant melanoma. In aspects, the methods are for treating renal cell cancer. In aspects, the methods are for treating breast cancer. In aspects, the methods are for treating triple negative breast cancer. In aspects, the methods are for treating colorectal cancer. In aspects, the methods are for treating microsatellite instable colorectal cancer. In aspects, the methods are for treating bladder cancer. In aspect, the methods are for treating head and neck cancers. In aspects, the methods are for treating prostate cancer. In aspects, the methods are for treating castration-resistant prostate cancer. In aspects, the methods are for treating metastatic castration-resistant prostate cancer. The methods of treating cancer encompass methods of treating metastatic cancer, methods of treating cancer tumors, and methods of treating metastatic cancer tumors.

The pharmaceutical compositions, oral formulations, granules, beads, tablets, capsules, powders, and oral formulations described herein contain the adenosine A2A receptor antagonist in a therapeutically effective amount, i.e., in an amount effective to treat cancer. When administered in methods to treat cancer, such compositions will contain an amount of active ingredient effective to achieve the desired results, which include one or more of (i) slowing the progression of the cancer; (ii) enhancing anti-tumor immune memory; (iii) increasing one or more of CD8+ cell infiltration, T cell activation, interferon-gamma pathway gene expression, and T cell clone expansion over baseline; (iv) preventing a tumor from growing in size or volume over time; (v) decreasing a cancerous tumor in size or volume over time; and (vi) preventing the cancerous tumor from metastasizing. Determination of a therapeutically effective amount of the adenosine A2A receptor antagonist is within the capabilities of the skilled artisan, especially in light of the detailed disclosure herein.

In embodiments of the methods of treating cancer with the pharmaceutical compositions and oral formulations (e.g., granules, beads, tablets, capsules, powders) described herein, the therapeutically effective amount of the adenosine A2A receptor antagonist is from about 1 mg to about 1,000 mg. In aspects, the therapeutically effective amount is from about 1 mg to about 900 mg. In aspects, the therapeutically effective amount is from about 1 mg to about 800 mg. In aspects, the therapeutically effective amount is from about 1 mg to about 700 mg. In aspects, the therapeutically effective amount is from about 1 mg to about 600 mg. In aspects, the therapeutically effective amount is from about 1 mg to about 500 mg. In aspects, the therapeutically effective amount is from about 1 mg to about 400 mg.

In embodiments of the methods of treating cancer with the pharmaceutical compositions and oral formulations (e.g., granules, beads, tablets, capsules, powders) described herein, the therapeutically effective amount of the adenosine A2A receptor antagonist is from about 100 mg to about 1,000 mg. In aspects, the therapeutically effective amount is from about 100 mg to about 900 mg. In aspects, the therapeutically effective amount is from about 100 mg to about 850 mg. In aspects, the therapeutically effective amount is from about 100 mg to about 800 mg. In aspects, the therapeutically effective amount is from about 100 mg to about 700 mg. In aspects, the therapeutically effective amount is from about 100 mg to about 600 mg. In aspects, the therapeutically effective amount is from about 100 mg to about 500 mg. In aspects, the therapeutically effective amount is from about 100 mg to about 450 mg. In aspects, the therapeutically effective amount is from about 100 mg to about 400 mg. In aspects, the therapeutically effective amount is from about 100 mg to about 300 mg. In aspects, the therapeutically effective amount is from about 150 mg to about 250 mg. In aspects, the therapeutically effective amount is from about 200 mg to about 400 mg. In aspects, the therapeutically effective amount is from about 250 mg to about 350 mg. In aspects, the therapeutically effective amount is from about 300 mg to about 500 mg. In aspects, the therapeutically effective amount is from about 350 mg to about 450 mg. In aspects, the administration of this therapeutically effective amount is QD. In aspects, the administration of this therapeutically effective amount is BID.

In embodiments of the methods of treating cancer with the pharmaceutical compositions and oral formulations (e.g., granules, beads, tablets, capsules, powders) described herein, the therapeutically effective amount of the adenosine A2A receptor antagonist is about 100 mg. In aspects, the therapeutically effective amount of the adenosine A2A receptor antagonist is about 125 mg. In aspects, the therapeutically effective amount of the adenosine A2A receptor antagonist is about 150 mg. In aspects, the therapeutically effective amount of the adenosine A2A receptor antagonist is about 175 mg. In aspects, the therapeutically effective amount of the adenosine A2A receptor antagonist is about 200 mg. In aspects, the therapeutically effective amount of the adenosine A2A receptor antagonist is about 225 mg. In aspects, the therapeutically effective amount of the adenosine A2A receptor antagonist is about 250 mg. In aspects, the therapeutically effective amount of the adenosine A2A receptor antagonist is about 275 mg. In aspects, the therapeutically effective amount of the adenosine A2A receptor antagonist is about 300 mg. In aspects, the therapeutically effective amount of the adenosine A2A receptor antagonist is about 325 mg. In aspects, the therapeutically effective amount of the adenosine A2A receptor antagonist is about 350 mg. In aspects, the therapeutically effective amount of the adenosine A2A receptor antagonist is about 375 mg. In aspects, the therapeutically effective amount of the adenosine A2A receptor antagonist is about 400 mg. In aspects, the therapeutically effective amount of the adenosine A2A receptor antagonist is about 425 mg. In aspects, the therapeutically effective amount of the adenosine A2A receptor antagonist is about 450 mg. In aspects, the therapeutically effective amount of the adenosine A2A receptor antagonist is about 475 mg. In aspects, the therapeutically effective amount of the adenosine A2A receptor antagonist is about 500 mg. In aspects, the therapeutically effective amount of the adenosine A2A receptor antagonist is about 525 mg. In aspects, the therapeutically effective amount of the adenosine A2A receptor antagonist is about 550 mg. In aspects, the therapeutically effective amount of the adenosine A2A receptor antagonist is about 575 mg. In aspects, the therapeutically effective amount of the adenosine A2A receptor antagonist is about 600 mg. In aspects, the therapeutically effective amount of the adenosine A2A receptor antagonist is about 625 mg. In aspects, the therapeutically effective amount of the adenosine A2A receptor antagonist is about 650 mg. In aspects, the therapeutically effective amount of the adenosine A2A receptor antagonist is about 675 mg. In aspects, the therapeutically effective amount of the adenosine A2A receptor antagonist is about 700 mg. In aspects, the therapeutically effective amount of the adenosine A2A receptor antagonist is about 725 mg. In aspects, the therapeutically effective amount of the adenosine A2A receptor antagonist is about 750 mg. In aspects, the therapeutically effective amount of the adenosine A2A receptor antagonist is about 775 mg. In aspects, the therapeutically effective amount of the adenosine A2A receptor antagonist is about 800 mg. In aspects, the therapeutically effective amount of the adenosine A2A receptor antagonist is about 825 mg. In aspects, the therapeutically effective amount of the adenosine A2A receptor antagonist is about 850 mg. In aspects, the therapeutically effective amount of the adenosine A2A receptor antagonist is about 875 mg. In aspects, the therapeutically effective amount of the adenosine A2A receptor antagonist is about 900 mg. In aspects, the therapeutically effective amount of the adenosine A2A receptor antagonist is about 950 mg. In aspects, the therapeutically effective amount of the adenosine A2A receptor antagonist is about 1,000 mg. In aspects, the administration of this therapeutically effective amount is QD. In aspects, the administration of this therapeutically effective amount is BID.

The frequency (e.g., once per day, twice per day, thrice per day) and duration (e.g., one week, two weeks, one month, two months, six months, 1 year, 5 to 10 years, or until disease progression) of administration of the pharmaceutical compositions described herein can vary depending upon a variety of factors, for example, whether the patient suffers from another disease, and the route of administration; size, age, sex, health, body weight; nature and extent of symptoms of the disease being treated; whether there is concurrent treatment (e.g., with chemotherapeutic agents, radiation, or immunomodulatory compounds), complications from the cancer being treated or other health-related problems. Adjustment and manipulation of the frequency and duration of treatment are within the ability of one skilled in the art. In aspects, the pharmaceutical compositions described herein are administered to the patient once per day (QD). In aspects, the pharmaceutical compositions are administered twice per day (BID). In aspects, the pharmaceutical compositions are administered thrice per day. In aspects, the pharmaceutical compositions are administered once per day for about 7 days. In aspects, the pharmaceutical compositions are administered once per day for about 14 days. In aspects, the pharmaceutical compositions are administered once per day for about 21 days. In aspects, the pharmaceutical compositions are administered once per day for about one month. In aspects, the pharmaceutical compositions are administered once per day until disease progression. In aspects, the pharmaceutical compositions are administered twice per day for about 7 days. In aspects, the pharmaceutical compositions are administered twice per day for about 14 days. In aspects, the pharmaceutical compositions are administered twice per day for about 21 days. In aspects, the pharmaceutical compositions are administered twice per day for one month. In aspects, the pharmaceutical compositions are administered twice per day until disease progression. After administration for 14 days, another cycle of administration can immediately begin or there can be a discontinuation of treatment for 14 days or one month, followed by another cycle of administration. After administration for a month, another cycle of administration can immediately begin or there can be a discontinuation of treatment for 14 days or one month, followed by another cycle of administration. Thus, after administration for one cycle (e.g., once/twice/thrice per day for 7 days, 14 days, 21 days, 1 month), another cycle of administration can immediately begin or there can be a discontinuation of treatment for a period of time (e.g., 7 days, 14, days, 21 days, 1 month), followed by another cycle of administration. The cycles of administration and/or discontinuation can be the same period of time (e.g., 14 days) or different periods of time (e.g., one cycle is 14 days and another cycle is 21 days).

Process of Manufacture

In embodiments, the adenosine A2A receptor antagonist (e.g., compound of Formula (III)) is micronized. The adenosine A2A receptor antagonist can be micronized by any process known in the art. In aspects, the adenosine A2A receptor antagonist is micronized by dry milling, either alone or with one or more pharmaceutically acceptable excipients. An exemplary dry milling device is a jet milling. In aspects, the adenosine A2A receptor antagonist is micronized by wet milling, either alone or with one or more pharmaceutically acceptable excipients. Exemplary wet milling devices include planetary mill, ball mill, agitator bead mill, and spray drying.

After the adenosine A2A receptor antagonist is micronized, it is screened and blended with the pharmaceutically acceptable excipients described herein. The screening step can be performed with any milling device or sieving device known in the art, such as with a gyratory screening machine, a tumbler screening machine, a vibration screening machine, a tumbler-vibration screening machine, or a comil. Any appropriate sieve size may be used in this step of the process. In aspects, the sieve size is a #16 mesh US standard sieve; or a #18 mesh US standard sieve; or a #20 mesh US standard sieve. In aspects, the sieve size is a #20 mesh US standard sieve; or a #30 mesh US standard sieve; or a #35 mesh US standard sieve.

After screening and blending the adenosine A2A receptor antagonist and pharmaceutically acceptable excipients, the blended formulation is granulated to form agglomerates of the adenosine A2A receptor antagonist and pharmaceutically acceptable excipients. Granulation techniques include wet granulation (e.g., low shear, high shear, fluid bed); dry granulation (e.g., roller compaction), and the like. Thereafter, the granules, if not produced from a dry process, are dried (e.g., oven tray drying, fluid bed drying) to remove any moisture.

Following or in series with granulation, the formulation is milled with any milling device known in the art, such as with a gyratory screening machine, a tumbler screening machine, a vibration screening machine, or a tumbler-vibration screening machine. In aspects, a FitzMill® Comminutor (The Fitzpatrick Company) may be used. For certain dry granulation processes, the milling step may be connected to and immediately following the granulation process. Thereafter, the formulation may be further blended with pharmaceutically acceptable excipients, compressed into a tablet, and optionally coated with a coating layer, such as OPADRY®.

These methods of forming the compositions described herein are described in more detail in the Examples.

EMBODIMENTS

Embodiment 1. A pharmaceutical composition comprising drug particles and a pharmaceutically acceptable excipient; wherein the drug particles comprise an adenosine A2A receptor antagonist or a pharmaceutically acceptable salt thereof having a size distribution with a D90 of about 30 microns or less, as measured by laser diffraction spectroscopy.

Embodiment 2. The pharmaceutical composition of claim 1, wherein the adenosine A2A receptor antagonist is a compound of Formula (I).

Embodiment 3. The pharmaceutical composition of claim 1, wherein the adenosine A2A receptor antagonist is a compound of Formula (II).

Embodiment 4. The pharmaceutical composition of claim 1, wherein the adenosine A2A receptor antagonist is a compound of Formula (III).

Embodiment 5. The pharmaceutical composition of claim 1, wherein the adenosine A2A receptor antagonist is a compound of Formula (IIIA).

Embodiment 6. The pharmaceutical composition of claim 1, wherein the adenosine A2A receptor antagonist is a compound of Formula (IIIB).

Embodiment 7. The composition of any one of Embodiments 1 to 6, wherein the drug particles have a size distribution with a D90 of about 25 microns or less, as measured by laser diffraction spectroscopy.

Embodiment 8. The composition of Embodiment 7, wherein the drug particles have a size distribution with a D90 of about 20 microns or less, as measured by laser diffraction spectroscopy.

Embodiment 9. The composition of Embodiment 8, wherein the drug particles have a size distribution with a D90 of about 15 microns or less, as measured by laser diffraction spectroscopy.

Embodiment 10. The composition of Embodiment 9, wherein the drug particles have a size distribution with a D90 of about 10 microns or less, as measured by laser diffraction spectroscopy.

Embodiment 11. The composition of any one of Embodiments 1 to 10, wherein the pharmaceutically acceptable excipient comprises a filler, a disintegrant, a binder, a surfactant, a glidant, or a combination of two or more thereof.

Embodiment 12. The composition of any one of Embodiments 1 to 10, wherein the pharmaceutically acceptable excipient comprises: (i) a polyol, maltodextrin, microcrystalline cellulose, dicalcium phosphate, or a combination of two or more thereof; (ii) carboxymethyl cellulose, sodium starch glycolate, a crosslinked polyvinylpyrrolidone polymer, or a combination of two or more thereof; (iii) a hydroxyalkyl cellulose, an alkyl cellulose, corn starch, polyethylene glycol, polyethylene oxide, polyvinylpyrrolidone, or a combination of two or more thereof; (iv) a compound from (i) and a compound from (ii); (v) a compound from (i) and a compound from (iii); (vi) a compound from (ii) and a compound from (iii); or (vii) a compound from (i), a compound from (ii), and a compound from (iii).

Embodiment 13. The composition of Embodiment 12, comprising a compound from (i), a compound from (ii), and a compound from (iii).

Embodiment 14. The composition of Embodiment 13, comprising about 40 wt % to about 80 wt % of a compound from (i), about 1 wt % to about 20 wt % of a compound from (ii), and about 1 wt % to about 20 wt % of a compound from (iii).

Embodiment 15. The composition of Embodiment 14, comprising about 50 wt % to about 70 wt % of a compound from (i), about 1 wt % to about 15 wt % of a compound from (ii), and about 1 wt % to about 10 wt % of a compound from (iii).

Embodiment 16. The composition of Embodiment 15, comprising about 55 wt % to about 65 wt % of a compound from (i), about 2 wt % to about 12 wt % of a compound from (iii), and about 1 wt % to about 8 wt % of a compound from (iii).

Embodiment 17. The composition of Embodiment 16, comprising about 58 wt % to about 63 wt % of a compound from (i), about 2 wt % to about 10 wt % of a compound from (iii), and about 2 wt % to about 8 wt % of a compound from (iii).

Embodiment 18. The composition of Embodiment 17, comprising about 61 wt % of a compound from (i); about 8 wt % of a compound from (ii); and about 4 wt % of a compound from (iii).

Embodiment 19. The composition of any one of Embodiments 1 to 10, wherein the pharmaceutically acceptable excipient comprises: (i) a polyol; (ii) microcrystalline cellulose; (ii) carboxymethyl cellulose; and (iii) a hydroxy alkyl cellulose.

Embodiment 20. The composition of any one of Embodiments 1 to 10, wherein the pharmaceutically acceptable excipient comprises (i) a polyol, (ii) microcrystalline cellulose, (iii) maltodextrin, (iv) carboxymethyl cellulose, (v) a hydroxy alkyl cellulose, (vi) an alkyl cellulose, or (vii) a combination of two or more thereof.

Embodiment 21. The composition of Embodiment 7, 19, or 20, wherein the hydroxyalkyl cellulose is hydroxypropyl cellulose, hydroxyethyl cellulose, hydroxypropylmethyl cellulose, or a combination of two or more thereof.

Embodiment 22. The composition of Embodiment 21, wherein the hydroxyalkyl cellulose is hydroxypropyl cellulose.

Embodiment 23. The composition of Embodiment 12, 19, 20, 21, or 22, wherein the polyol is mannitol, sorbitol, isomaltose, maltitol, lactose, sucrose, amylose, glucose, dextrose, lactitol, erythritol, arabitol, xylitol, trehalose ribitol, inositol, or a combination of two or more thereof.

Embodiment 24. The composition of Embodiment 23, wherein the polyol is mannitol.

Embodiment 25. The composition of any one of Embodiments 1 to 24, comprising from about 1 wt % to about 50 wt % of the adenosine A2A receptor antagonist.

Embodiment 26. The composition of Embodiment 25, comprising from about 5 wt % to about 45 wt % of the adenosine A2A receptor antagonist.

Embodiment 27. The composition of Embodiment 26, comprising from about 10 wt % to about 40 wt % of the adenosine A2A receptor antagonist.

Embodiment 28. The composition of Embodiment 27, comprising from about 15 wt % to about 35 wt % of the adenosine A2A receptor antagonist.

Embodiment 29. The composition of Embodiment 28, comprising from about 20 wt % to about 30 wt % of the adenosine A2A receptor antagonist.

Embodiment 30. The composition of Embodiment 29, comprising from about 24 wt % to about 26 wt % of the adenosine A2A receptor antagonist.

Embodiment 31. The composition of Embodiment 30, comprising about 25 wt % of the adenosine A2A receptor antagonist.

Embodiment 32. The composition of any one of Embodiments 1 to 31, further comprising about 0.5 wt % to about 4 wt % of a lubricant.

Embodiment 33. The composition of Embodiment 32, comprising about 0.5 wt % to about 2.3 wt % of a lubricant.

Embodiment 34. The composition of Embodiment 33, comprising about 2.25 wt % of a lubricant.

Embodiment 35. The composition of any one of Embodiments 1 to 34, comprising from about 1 mg to about 1,000 mg of the adenosine A2A receptor antagonist.

Embodiment 36. The composition of Embodiment 35, comprising from about 50 mg to about 600 mg of the adenosine A2A receptor antagonist.

Embodiment 37. The composition of Embodiment 36, comprising about 50 mg, about 100 mg, about 150 mg, about 200 mg, about 250 mg, about 300 mg, about 350 mg, about 400 mg, about 450 mg, about 500 mg, about 550 mg, or about 600 mg of the adenosine A2A receptor antagonist.

Embodiment 38. The composition of any one of Embodiments 1 to 37 having a disintegration time of about 15 minutes or less, as measured by US Pharmacopeia (USP), Chapter <701>, Disintegration Test method.

Embodiment 39. The composition of Embodiment 38 having a dissolution of about 10 minutes or less, as measured by US Pharmacopeia (USP), Chapter <701>, Disintegration Test method.

Embodiment 40. The composition of any one of Embodiments 1 to 39 having a dissolution of at least 75% in 60 minutes, as measured by US Pharmacopeia (USP), Chapter <711>, Type II (Paddle) Dissolution Apparatus method.

Embodiment 41. The composition of Embodiment 40 having a dissolution of at least 90% in 60 minutes, as measured by US Pharmacopeia (USP), Chapter <711>, Type II (Paddle) Dissolution Apparatus method.

Embodiment 42. The composition of Embodiment 40 having a dissolution of at least 70% in 10 minutes, as measured by US Pharmacopeia (USP), Chapter <711>, Type II (Paddle) Dissolution Apparatus method.

Embodiment 43. The composition of any one of Embodiments 1 to 42, wherein the composition is an oral formulation.

Embodiment 44. The composition of Embodiment 43, wherein the composition is a tablet.

Embodiment 45. The composition of Embodiment 43, wherein the composition is a powder.

Embodiment 46. The composition of Embodiment 43, wherein the composition is a capsule.

Embodiment 47. A method of treating cancer in a subject in need thereof, the method comprising administering to the subject a therapeutically effective amount of the composition of any one of Embodiments 1 to 46 to treat the cancer.

Embodiment 48. The method of Embodiment 47, wherein the cancer is non-small cell lung cancer, melanoma, renal cell cancer, breast cancer, colorectal cancer, bladder cancer, prostate cancer, or a head and neck cancer.

Embodiment 49. The method of Embodiment 47 or 48, wherein the therapeutically effective amount is about 1 mg to about 1,000 mg per day.

Embodiment 50. The method of Embodiment 49, wherein the therapeutically effective amount is about 10 mg to about 600 mg per day.

Embodiment 51. The method of Embodiment 50, wherein the therapeutically effective amount is about 100 mg to about 400 mg per day.

Embodiment 52. A granule comprising drug particles and a pharmaceutically acceptable excipient; wherein the drug particles comprise an adenosine A2A receptor antagonist or a pharmaceutically acceptable salt thereof having a size distribution with a D90 of about 30 microns or less, as measured by laser diffraction spectroscopy.

Embodiment 53. The granule of Embodiment 52, wherein the adenosine A2A receptor antagonist is a compound of Formula (I).

Embodiment 54. The granule of Embodiment 52, wherein the adenosine A2A receptor antagonist is a compound of Formula (II).

Embodiment 55. The granule of Embodiment 52, wherein the adenosine A2A receptor antagonist is a compound of Formula (III).

Embodiment 56. The granule of Embodiment 52, wherein the adenosine A2A receptor antagonist is a compound of Formula (IIIA).

Embodiment 57. The granule of Embodiment 52, wherein the adenosine A2A receptor antagonist is a compound of Formula (IIIB).

Embodiment 58. The granule of any one of Embodiments 52 to 57, wherein the drug particles have a size distribution with a D90 of about 25 microns or less, as measured by laser diffraction spectroscopy.

Embodiment 59. The granule of Embodiment 58, wherein the drug particles have a size distribution with a D90 of about 20 microns or less, as measured by laser diffraction spectroscopy.

Embodiment 60. The granule of Embodiment 58, wherein the drug particles have a size distribution with a D90 of about 15 microns or less, as measured by laser diffraction spectroscopy.

Embodiment 61. The granule of Embodiment 58, wherein the drug particles have a size distribution with a D90 of about 10 microns or less, as measured by laser diffraction spectroscopy.

Embodiment 62. The granule of any one of Embodiments 52 to 61, wherein the pharmaceutically acceptable excipient comprises a filler, a disintegrant, a binder, a lubricant, a surfactant, a glidant, or a combination of two or more thereof.

Embodiment 63. The granule of Embodiments 52 to 61, wherein the pharmaceutically acceptable excipient comprises: (i) a polyol, maltodextrin, microcrystalline cellulose, dicalcium phosphate, or a combination of two or more thereof; (ii) carboxymethyl cellulose, sodium starch glycolate, a crosslinked polyvinylpyrrolidone polymer, or a combination of two or more thereof; (iii) a hydroxyalkyl cellulose, an alkyl cellulose, corn starch, polyethylene glycol, polyethylene oxide, polyvinylpyrrolidone, or a combination of two or more thereof; (iv) a compound from (i) and a compound from (ii); (v) a compound from (i) and a compound from (iii); (vi) a compound from (ii) and a compound from (iii); or (vii) a compound from (i), a compound from (ii), and a compound from (iii).

Embodiment 64. The granule of Embodiment 63, comprising a compound from (i), a compound from (ii), and a compound from (iii).

Embodiment 65. The granule of Embodiment 64, comprising about 40 wt % to about 80 wt % of a compound from (i), about 1 wt % to about 20 wt % of a compound from (ii), and about 1 wt % to about 20 wt % of a compound from (iii).

Embodiment 66. The granule of Embodiment 65, comprising about 50 wt % to about 70 wt % of a compound from (i), about 1 wt % to about 15 wt % of a compound from (ii), and about 1 wt % to about 10 wt % of a compound from (iii).

Embodiment 67. The granule of Embodiment 66, comprising about 55 wt % to about 65 wt % of a compound from (i), about 2 wt % to about 12 wt % of a compound from (iii), and about 1 wt % to about 8 wt % of a compound from (iii).

Embodiment 68. The granule of Embodiment 67, comprising about 58 wt % to about 63 wt % of a compound from (i), about 2 wt % to about 10 wt % of a compound from (iii), and about 2 wt % to about 8 wt % of a compound from (iii).

Embodiment 69. The granule of Embodiment 68, comprising about 61 wt % of a compound from (i); about 8 wt % of a compound from (ii); and about 4 wt % of a compound from (iii).

Embodiment 70. The granule of any one of Embodiments 52 to 61, wherein the pharmaceutically acceptable excipient comprises: (i) a polyol; (ii) microcrystalline cellulose; (ii) carboxymethyl cellulose; and (iii) a hydroxy alkyl cellulose.

Embodiment 71. The granule of any one of Embodiments 52 to 61, wherein the pharmaceutically acceptable excipient comprises (i) a polyol, (ii) microcrystalline cellulose, (iii) maltodextrin, (iv) carboxymethyl cellulose, (v) a hydroxy alkyl cellulose, (vi) an alkyl cellulose, or (vii) a combination of two or more thereof Embodiment 72. The granule of Embodiment 63, 70, or 71, wherein the hydroxyalkyl cellulose is hydroxypropyl cellulose, hydroxyethyl cellulose, hydroxypropylmethyl cellulose, or a combination of two or more thereof.

Embodiment 73. The granule of Embodiment 72, wherein the hydroxyalkyl cellulose is hydroxypropyl cellulose.

Embodiment 74. The granule of Embodiment 63, 70, 71, 72, or 73, wherein the polyol is mannitol, sorbitol, isomaltose, maltitol, lactose, sucrose, amylose, glucose, dextrose, lactitol, erythritol, arabitol, xylitol, trehalose ribitol, inositol, or a combination of two or more thereof.

Embodiment 75. The granule of Embodiment 74, wherein the polyol is mannitol.

Embodiment 76. The granule of any one of Embodiments 52 to 75, comprising from about 1 wt % to about 50 wt % of the adenosine A2A receptor antagonist.

Embodiment 77. The granule of Embodiment 76, comprising from about 5 wt % to about 45 wt % of the adenosine A2A receptor antagonist.

Embodiment 78. The granule of Embodiment 77, comprising from about 10 wt % to about 40 wt % of the adenosine A2A receptor antagonist.

Embodiment 79. The granule of Embodiment 78, comprising from about 15 wt % to about 35 wt % of the adenosine A2A receptor antagonist.

Embodiment 80. The granule of Embodiment 79, comprising from about 20 wt % to about 30 wt % of the adenosine A2A receptor antagonist.

Embodiment 81. The granule of Embodiment 80, comprising from about 24 wt % to about 26 wt % of the adenosine A2A receptor antagonist.

Embodiment 82. The granule of Embodiment 81, comprising about 25 wt % of the adenosine A2A receptor antagonist.

Embodiment 83. The granule of any one of Embodiments 52 to 82, further comprising about 0.5 wt % to about 4 wt % of a lubricant.

Embodiment 84. The granule of Embodiment 83, comprising about 0.5 wt % to about 2.3 wt % of a lubricant.

Embodiment 85. The granule of Embodiment 84, comprising about 2.25 wt % of a lubricant Embodiment 86. A pharmaceutical composition comprising the granule of any one of Embodiments 52 to 85.

Embodiment 87. A tablet comprising the granule of any one of Embodiments 52 to 85.

Embodiment 88. A capsule comprising the granule of any one of Embodiments 52 to 85 encapsulated within a capsule shell.

Embodiment 89. A sachet or stick pack comprising the granule of any one of Embodiments 52 to 85.

Embodiment 90. The pharmaceutical composition of Embodiment 86, the tablet of Embodiment 87, the capsule of Embodiment 88, or the sachet or stick pack of Embodiment 89, comprising from about 1 mg to about 1,000 mg of the adenosine A2A receptor antagonist.

Embodiment 91. The pharmaceutical composition of Embodiment 86, the tablet of Embodiment 87, the capsule of Embodiment 88, or the sachet or stick pack of Embodiment 89, comprising from about 50 mg to about 500 mg of the adenosine A2A receptor antagonist.

Embodiment 92. The pharmaceutical composition of Embodiment 86, the tablet of Embodiment 87, the capsule of Embodiment 88, or the sachet or stick pack of Embodiment 89, comprising about 50 mg, about 100 mg, about 150 mg, about 200 mg, about 250 mg, about 300 mg, about 350 mg, about 400 mg, about 450 mg, about 500 mg, about 550 mg, or about 600 mg of the adenosine A2A receptor antagonist.

Embodiment 93. The pharmaceutical composition of Embodiment 86, the tablet of Embodiment 87, the capsule of Embodiment 88 having a disintegration time of about 15 minutes or less, as measured by US Pharmacopeia (USP), Chapter <701>, Disintegration Test method.

Embodiment 94. The pharmaceutical composition of Embodiment 86, the tablet of Embodiment 87, the capsule of Embodiment 88 having a disintegration time of about 10 minutes or less, as measured by US Pharmacopeia (USP), Chapter <701>, Disintegration Test method.

Embodiment 95. The pharmaceutical composition of Embodiment 86, the tablet of Embodiment 87, the capsule of Embodiment 88 having a dissolution of at least 75% in 60 minutes, as measured by US Pharmacopeia (USP), Chapter <711>, Type II (Paddle) Dissolution Apparatus method.

Embodiment 96. The pharmaceutical composition of Embodiment 86, the tablet of Embodiment 87, the capsule of Embodiment 88 having a dissolution of at least 90% in 60 minutes, as measured by US Pharmacopeia (USP), Chapter <711>, Type II (Paddle) Dissolution Apparatus method.

Embodiment 97. The pharmaceutical composition of Embodiment 86, the tablet of Embodiment 87, the capsule of Embodiment 88 having a dissolution of at least 70% in 10 minutes, as measured by US Pharmacopeia (USP), Chapter <711>, Type II (Paddle) Dissolution Apparatus method.

Embodiment 98. A method of treating cancer in a subject in need thereof, the method comprising administering a therapeutically effective amount of the granule of any one of Embodiments 52 to 85, the composition of any one of Embodiments 86 and 90-97, the tablet of any one of Embodiments 87 and 90-97, the capsule of any one of Embodiments 88 and 90-97, or the stick pack or sachet of Embodiment 89 to the subject to treat the cancer.

Embodiment 99. The method of Embodiment 98, wherein the cancer is lung cancer, melanoma, renal cell cancer, breast cancer, colorectal cancer, bladder cancer, prostate cancer, or a head and neck cancer.

Embodiment 100. The method of Embodiment 98 or 99, wherein the therapeutically effective amount is about 1 mg to about 1,000 mg per day.

Embodiment 101. The method of Embodiment 100, wherein the therapeutically effective amount is about 10 mg to about 600 mg per day.

Embodiment 102. The method of Embodiment 101, wherein the therapeutically effective amount is about 100 mg to about 400 mg per day.

Embodiment 103. A bead comprising an inert core and a drug layer; wherein the drug layer comprises drug particles and a pharmaceutically acceptable excipient; wherein the drug particles comprise an adenosine A2A receptor antagonist or a pharmaceutically acceptable salt thereof having a size distribution with a D90 of about 30 microns or less, as measured by laser diffraction spectroscopy.

Embodiment 104. The bead of Embodiment 103, wherein the adenosine A2A receptor antagonist is a compound of Formula (I).

Embodiment 105. The bead of Embodiment 103, wherein the adenosine A2A receptor antagonist is a compound of Formula (II).

Embodiment 106. The bead of Embodiment 103, wherein the adenosine A2A receptor antagonist is a compound of Formula (III).

Embodiment 107. The bead of Embodiment 103, wherein the adenosine A2A receptor antagonist is a compound of Formula (IIIA).

Embodiment 108. The bead of Embodiment 103, wherein the adenosine A2A receptor antagonist is a compound of Formula (IIIB).

Embodiment 109. The bead of any one of Embodiments 103 to 108, wherein the drug particles have a size distribution with a D90 of about 25 microns or less, as measured by laser diffraction spectroscopy.

Embodiment 110. The bead of Embodiment 109, wherein the drug particles have a size distribution with a D90 of about 20 microns or less, as measured by laser diffraction spectroscopy.

Embodiment 111. The bead of Embodiment 110, wherein the drug particles have a size distribution with a D90 of about 15 microns or less, as measured by laser diffraction spectroscopy.

Embodiment 112. The bead of Embodiment 111, wherein the drug particles have a size distribution with a D90 of about 10 microns or less, as measured by laser diffraction spectroscopy.

Embodiment 113. The bead of any one of Embodiments 103 to 112, wherein the core has a particle size greater than 50 microns.

Embodiment 114. The bead of Embodiment 113, wherein the core has a particle size from about 100 microns to about 2.5 mm.

Embodiment 115. The bead of any one of Embodiments 103 to 114, wherein the pharmaceutically acceptable excipient comprises a filler, a disintegrant, a binder, a lubricant, a surfactant, a glidant, or a combination of two or more thereof.

Embodiment 116. The bead of any one of Embodiments 103 to 114, wherein the pharmaceutically acceptable excipient comprises: (i) a polyol, maltodextrin, microcrystalline cellulose, dicalcium phosphate, or a combination of two or more thereof; (ii) carboxymethyl cellulose, sodium starch glycolate, a crosslinked polyvinylpyrrolidone polymer, or a combination of two or more thereof; (iii) a hydroxyalkyl cellulose, an alkyl cellulose, corn starch, polyethylene glycol, polyethylene oxide, polyvinylpyrrolidone, or a combination of two or more thereof; (iv) a compound from (i) and a compound from (ii); (v) a compound from (i) and a compound from (iii); (vi) a compound from (ii) and a compound from (iii); or (vii) a compound from (i), a compound from (ii), and a compound from (iii).

Embodiment 117. The bead of Embodiment 116, comprising a compound from (i), a compound from (ii), and a compound from (iii).

Embodiment 118. The bead of Embodiment 117, comprising about 40 wt % to about 80 wt % of a compound from (i), about 1 wt % to about 20 wt % of a compound from (ii), and about 1 wt % to about 20 wt % of a compound from (iii).

Embodiment 119. The bead of Embodiment 118, comprising about 50 wt % to about 70 wt % of a compound from (i), about 1 wt % to about 15 wt % of a compound from (ii), and about 1 wt % to about 10 wt % of a compound from (iii).

Embodiment 120. The bead of Embodiment 119, comprising about 55 wt % to about 65 wt % of a compound from (i), about 2 wt % to about 12 wt % of a compound from (iii), and about 1 wt % to about 8 wt % of a compound from (iii).

Embodiment 121. The bead of Embodiment 120, comprising about 58 wt % to about 63 wt % of a compound from (i), about 2 wt % to about 10 wt % of a compound from (iii), and about 2 wt % to about 8 wt % of a compound from (iii).

Embodiment 122. The bead of Embodiment 121, comprising about 61 wt % of a compound from (i); about 8 wt % of a compound from (ii); and about 4 wt % of a compound from (iii).

Embodiment 123. The bead of any one of Embodiments 103 to 114, wherein the pharmaceutically acceptable excipient comprises: (i) a polyol; (ii) microcrystalline cellulose; (ii) carboxymethyl cellulose; and (iii) a hydroxy alkyl cellulose.

Embodiment 124. The bead of any one of Embodiments 103 to 114, wherein the pharmaceutically acceptable excipient comprises (i) a polyol, (ii) microcrystalline cellulose, (iii) maltodextrin, (iv) carboxymethyl cellulose, (v) a hydroxy alkyl cellulose, (vi) an alkyl cellulose, or (vii) a combination of two or more thereof.

Embodiment 125. The bead of Embodiment 116, 123, or 124, wherein the hydroxyalkyl cellulose is hydroxypropyl cellulose, hydroxyethyl cellulose, hydroxypropylmethyl cellulose, or a combination of two or more thereof.

Embodiment 126. The bead of Embodiment 125, wherein the hydroxyalkyl cellulose is hydroxypropyl cellulose.

Embodiment 127. The bead of Embodiment 116, 123, 124, 125, 126, or 127, wherein the polyol is mannitol, sorbitol, isomaltose, maltitol, lactose, sucrose, amylose, glucose, dextrose, lactitol, erythritol, arabitol, xylitol, trehalose ribitol, inositol, or a combination of two or more thereof.

Embodiment 128. The bead of Embodiment 127, wherein the polyol is mannitol

Embodiment 129. The bead of any one of Embodiments 103 to 128, comprising from about 1 wt % to about 50 wt % of the adenosine A2A receptor antagonist.

Embodiment 130. The bead of Embodiment 129, comprising from about 5 wt % to about 45 wt % of the adenosine A2A receptor antagonist.

Embodiment 131. The bead of Embodiment 130, comprising from about 10 wt % to about 40 wt % of the adenosine A2A receptor antagonist.

Embodiment 132. The bead of Embodiment 131, comprising from about 15 wt % to about 35 wt % of the adenosine A2A receptor antagonist.

Embodiment 133. The bead of Embodiment 132, comprising from about 20 wt % to about 30 wt % of the adenosine A2A receptor antagonist.

Embodiment 134. The bead of Embodiment 133, comprising from about 24 wt % to about 26 wt % of the adenosine A2A receptor antagonist.

Embodiment 135. The bead of Embodiment 134, comprising about 25 wt % of the adenosine A2A receptor antagonist.

Embodiment 136. A pharmaceutical composition comprising the bead of any one of Embodiments 103 to 135.

Embodiment 137. A tablet comprising the bead of any one of Embodiments 103 to 135.

Embodiment 138. A capsule comprising the bead of any one of Embodiments 103 to 135.

Embodiment 139. A stick pack or sachet comprising the bead of any one of Embodiments 103 to 135.

Embodiment 140. The pharmaceutical composition of Embodiment 136, the tablet of Embodiment 137, the capsule of Embodiment 138, or the stick pack or sachet of Embodiment 139, comprising from about 1 mg to about 1,000 mg of the adenosine A2A receptor antagonist.

Embodiment 141. The pharmaceutical composition of Embodiment 136, the tablet of Embodiment 137, the capsule of Embodiment 138, or the stick pack or sachet of Embodiment 139, comprising from about 50 mg to about 600 mg of the adenosine A2A receptor antagonist.

Embodiment 142. The pharmaceutical composition of Embodiment 136, the tablet of Embodiment 137, the capsule of Embodiment 138, or the stick pack or sachet of Embodiment 139, comprising about 50 mg, about 100 mg, about 150 mg, about 200 mg, about 250 mg, about 300 mg, about 350 mg, about 400 mg, about 450 mg, about 500 mg, about 550 mg, or about 600 mg of the adenosine A2A receptor antagonist.

Embodiment 143. The pharmaceutical composition of Embodiment 136, the tablet of Embodiment 137, or the capsule of Embodiment 138, having a disintegration time of about 15 minutes or less, as measured by US Pharmacopeia (USP), Chapter <701>, Disintegration Test method.

Embodiment 144. The pharmaceutical composition of Embodiment 136, the tablet of Embodiment 137, or the capsule of Embodiment 138, having a disintegration time of about 10 minutes or less, as measured by US Pharmacopeia (USP), Chapter <701>, Disintegration Test method.

Embodiment 145. The pharmaceutical composition of Embodiment 136, the tablet of Embodiment 137, or the capsule of Embodiment 138, having a dissolution of at least 75% in 60 minutes, as measured by US Pharmacopeia (USP), Chapter <711>, Type II (Paddle) Dissolution Apparatus method.

Embodiment 146. The pharmaceutical composition of Embodiment 136, the tablet of Embodiment 137, or the capsule of Embodiment 138, having a dissolution of at least 90% in 60 minutes, as measured by US Pharmacopeia (USP), Chapter <711>, Type II (Paddle) Dissolution Apparatus method.

Embodiment 147. The pharmaceutical composition of Embodiment 136, the tablet of Embodiment 137, or the capsule of Embodiment 138, having a dissolution of at least 70% in 10 minutes, as measured by US Pharmacopeia (USP), Chapter <711>, Type II (Paddle) Dissolution Apparatus method.

Embodiment 148. A method of treating cancer in a subject in need thereof, the method comprising administering to the subject a therapeutically effective amount of the bead of any one of Embodiments 103 to 135, the pharmaceutical composition of Embodiment 136, the tablet of Embodiment 137, the capsule of Embodiment 138, or the stick pack or sachet of Embodiment 139 to treat the cancer.

Embodiment 149. The method of Embodiment 148, wherein the cancer is non-small cell lung cancer, melanoma, renal cell cancer, breast cancer, colorectal cancer, bladder cancer, prostate cancer, or a head and neck cancer.

Embodiment 150. The method of Embodiment 148 or 149, wherein the therapeutically effective amount of the adenosine A2A receptor antagonist is about 1 mg to about 1,000 mg per day.

Embodiment 151. The method of Embodiment 150, wherein the therapeutically effective amount of the adenosine A2A receptor antagonist is about 50 mg to about 600 mg per day.

Embodiment 152. The method of Embodiment 151, wherein the therapeutically effective amount of the adenosine A2A receptor antagonist is about 50 mg, about 100 mg, about 150 mg, about 200 mg, about 250 mg, about 300 mg, about 350 mg, about 400 mg, about 450 mg, about 500 mg, about 550 mg, or about 600 mg Embodiment 153. A composition, or a bioequivalent formulation thereof, comprising: (i) about 20 wt % to about 30 wt % of a compound of Formula (III) or a pharmaceutically acceptable salt thereof having a particle size distribution with a D90 of about 10 microns or less, as measured by laser diffraction spectroscopy; (ii) about 35 wt % to about 40 wt % of mannitol; (iii) about 15 wt % to about 30 wt % of microcrystalline cellulose; (iv) about 4 wt % to about 12 wt % of crosslinked sodium carboxymethyl cellulose; and (v) about 1 wt % to about 8 wt % of hydroxypropyl cellulose.

Embodiment 154. The composition of Embodiment 153, wherein the mannitol comprises a spray-dried mannitol and a crystalline mannitol in a weight ratio from about 1:1 to about 1:3.

Embodiment 155. A composition, or a bioequivalent formulation thereof, comprising: (i) about 24 wt % to about 26 wt % of a compound of Formula (III) or a pharmaceutically acceptable salt thereof having a particle size distribution with a D90 of about 10 microns or less, as measured by laser diffraction spectroscopy; (ii) about 37 wt % to about 40 wt % of mannitol; (iii) about 20 wt % to about 25 wt % of microcrystalline cellulose; (iv) about 4 wt % to about 12 wt % of crosslinked sodium carboxymethyl cellulose; and (v) about 2 wt % to about 6 wt % of hydroxypropyl cellulose.

Embodiment 156. The composition of Embodiment 155, wherein the mannitol comprises a spray-dried mannitol and a crystalline mannitol in a weight ratio from about 1:1.5 to about 1:2.5.

Embodiment 157. Pharmaceutical composition No. 1 or a bioequivalent formulation thereof.

Embodiment 158. Pharmaceutical composition No. 2 or a bioequivalent formulation thereof.

Embodiment 159. Pharmaceutical composition No. 3 or a bioequivalent formulation thereof.

Embodiment 160. Pharmaceutical composition No. 4 or a bioequivalent formulation thereof.

Embodiment 161. Pharmaceutical composition No. 5 or a bioequivalent formulation thereof.

Embodiment 162. Pharmaceutical composition No. 6 or a bioequivalent formulation thereof.

Embodiment 163. The composition of any one of Embodiments 153 to 162, comprising from about 1 mg to about 1,000 mg of the compound of Formula (III).

Embodiment 164. The composition of Embodiment 163, comprising from about 50 mg to about 600 mg of the compound of Formula (III).

Embodiment 165. The composition of Embodiment 164, comprising from about 100 mg to about 400 mg of the compound of Formula (III).

Embodiment 166. The composition of Embodiment 163, comprising about 50 mg, about 100 mg, about 150 mg, about 200 mg, about 250 mg, about 300 mg, about 350 mg, about 400 mg, about 450 mg, about 500 mg, about 550 mg, or about 600 mg of the compound of Formula (III).

Embodiment 167. The composition of any one of Embodiments 153 to 166, having a disintegration time of about 15 minutes or less, as measured by US Pharmacopeia (USP), Chapter <701>, Disintegration Test method.

Embodiment 168. The composition of Embodiment 167, having a disintegration time of about 10 minutes or less, as measured by US Pharmacopeia (USP), Chapter <701>, Disintegration Test method.

Embodiment 169. The composition of any one of Embodiments 153 to 168 having a dissolution of at least 75% in 60 minutes, as measured by US Pharmacopeia (USP), Chapter <711>, Type II (Paddle) Dissolution Apparatus method.

Embodiment 170. The composition of Embodiment 169 having a dissolution of at least 75% in 60 minutes, as measured by US Pharmacopeia (USP), Chapter <711>, Type II (Paddle) Dissolution Apparatus method.

Embodiment 171. The composition of Embodiment 169 having a dissolution of at least 70% in 10 minutes, as measured by US Pharmacopeia (USP), Chapter <711>, Type II (Paddle) Dissolution Apparatus method.

Embodiment 172. A tablet comprising the composition of any one of Embodiments 153 to 171.

Embodiment 173. A capsule comprising the composition of any one of Embodiments 153 to 171.

Embodiment 174. A powder comprising the composition of any one of Embodiments 153 to 171.

Embodiment 175. A sachet or stick pack comprising the composition of any one of Embodiments 153 to 171.

Embodiment 176. A method of treating cancer in a subject in need thereof, the method comprising administering to the subject a therapeutically effective amount of the composition of any one of Embodiments 153 to 171, the tablet of Embodiment 172, the capsule of Embodiment 173, the powder of Embodiment 174, or the sachet or stick pack of Embodiment 175 to treat the cancer.

Embodiment 177. The method of Embodiment 176, wherein the cancer is non-small cell lung cancer, melanoma, renal cell cancer, breast cancer, colorectal cancer, bladder cancer, prostate cancer, or a head and neck cancer.

Embodiment 178. The method of Embodiment 176 or 177, wherein the therapeutically effective amount is about 1 mg to about 1,000 mg per day.

Embodiment 179. The method of Embodiment 178, wherein the therapeutically effective amount is about 50 mg to about 600 mg per day.

Embodiment 48. The method of Embodiment 179, wherein the therapeutically effective amount is about 100 mg to about 400 mg per day.

Embodiment 49. The method of Embodiment 178, wherein the therapeutically effective amount is s about 50 mg, about 100 mg, about 150 mg, about 200 mg, about 250 mg, about 300 mg, about 350 mg, about 400 mg, about 450 mg, about 500 mg, about 550 mg, or about 600 mg per day.

EXAMPLES

Abbreviations: API: Active Pharmaceutical Ingredient (Formula (III)); ASD: Amorphous Solid Dispersion; RH: Relative humidity; RT: Room temperature; RRT: Relative retention time (in HPLC); XRPD: X-ray powder diffraction; YTZ: yttria-stabilized zirconia.

Example 1

Formulation (III) was micronized using a Sturtevant SDM jet mill with a 2 inch diameter loop. The process parameters were: inlet air pressure 120 psi; grind chamber 100 psi; nozzle air pressure 80 psi; manual fee rate. The particle size of Formula (III) before and after micronization is shown in Table 1A.

TABLE 1A

|  | D10 | D50 | D90 |
| --- | --- | --- | --- |
| Before micronization | 2.3 microns | 8.6 microns | 31.1 microns |
| 1 pass micronization | 0.9 microns | 3.3 microns | 8.2 microns |

Formulation (III) was micronized using a Sturtevant SDM jet mill with a 4 inch diameter loop. The process parameters were: inlet air pressure 120 psi; grind chamber 100 psi; nozzle air pressure 80 psi; manual fee rate. The particle size of Formula (III) before and after micronization is shown in Table 1B.

TABLE 1B

|  | D10 | D50 | D90 |
| --- | --- | --- | --- |
| Before micronization | 2.3 microns | 8.6 microns | 31.1 microns |
| 1 pass micronization | 1.1 microns | 4.3 microns | 20.2 microns |
| 2 pass micronization | 0.9 microns | 3.1 microns | 8.3 microns |

Example 2

Pharmaceutical Composition No. 1 (Formulation 003A) shown in Table 2A and Table 2B was prepared by the following process. Formula (III) was micronized in a jet mill until there was a particle size distribution with a D90 of 10 microns, as measured by laser diffraction spectroscopy. Thereafter, using the ratios for the granular portion shown in Table 2B, Formula (III) was blended with (i) spray-dried lactose, (ii) microcrystalline cellulose (MCC 102), (iii) internally crosslinked sodium carboxymethyl cellulose (Ac-Di-Sol®, FMC Corporation, Philadelphia, Pa.), and (iv) hydroxypropyl cellulose (KLUCEL® EF, Ashland, Covington, Ky.). The blend was screened through a US standard #30 mesh (600 microns), then mixed again. The blend was wet granulated (mortar and pestle; 20% w/v granulation formed), and then dried at 60° C., and then screened through a US standard #30 mesh screen. Using the appropriate ratios for the extra-granular portion in Table 2B, the granules were then blended with (i) microcrystalline cellulose (MCC 102), (ii) internally crosslinked sodium carboxymethyl cellulose (Ac-Di-Sol®, FMC Corporation, Philadelphia, Pa.), and (iii) sodium stearyl fumarate to form pharmaceutical composition No. 1, which was then compressed with a single stage Carver Press (round concave 0.3150" diameter (8 mm) with 8 kP hardness).

TABLE 2A

Pharmaceutical Composition No. 1

| Component | Function | mg/tablet | wt % |
|---|---|---|---|
| Formula (III) | Active Ingredient | 25 | 14.7 |
| Lactose | Filler | 75 | 44.1 |
| Microcrystalline cellulose | Filler | 53 | 31.2 |
| Carboxymethyl Cellulose Sodium | Disintegrant | 10 | 5.9 |
| Hydroxypropyl Cellulose | Binder | 5 | 2.9 |
| Sodium Stearyl Fumarate | Lubricant | 2 | 1.2 |

TABLE 2B

Pharmaceutical Composition No. 1

| INGREDIENTS | mg | % |
|---|---|---|
| Granular Portion | | |
| Formula (III) | 25 | 14.7 |
| Lactose monohydrate (SD) | 75 | 44.1 |
| Microcrystalline Cellulose (MCC102) | 20 | 11.8 |
| Croscarmellose Sodium (Ac-Di-Sol) | 5 | 2.9 |
| Hydroxypropyl cellulose (Klucel EF) | 5 | 2.9 |
| Extra-Granular Portion | | |
| Croscarmellose Sodium (Ac-Di-Sol) | 5 | 2.9 |
| Microcrystalline Cellulose (MCC102) | 33 | 19.4 |
| Sodium Stearyl Fumarate, NF | 5 | 1.2 |

Example 3

Pharmaceutical Composition No. 2 (Formulation 003B) shown in Table 3A and Table 3B was prepared by the following process. Formula (III) was micronized in a jet mill until there was a particle size distribution with a D90 of 10 microns, as measured by laser diffraction spectroscopy. Thereafter, using the ratios for the granular portion in Table 3B, Formula (III) was blended with (i) spray-dried lactose, (ii) microcrystalline cellulose (MCC 102), (iii) internally crosslinked sodium carboxymethyl cellulose (Ac-Di-Sol®, FMC Corporation, Philadelphia, Pa.), (iv) docusate sodium granular, and (v) hydroxypropyl cellulose (KLUCEL® EF, Ashland, Covington, Ky.). The blend was screened through a US standard #30 mesh (600 microns), then mixed again. The blend was wet granulated (mortar and pestle; 20% w/v granulation formed), and then dried at 60° C., and then screened through a US standard #30 mesh screen. Thereafter, using the ratios for the extra-granular portion shown in Table 3B, the granules were then blended with (i) microcrystalline cellulose (MCC 102), (ii) internally crosslinked sodium carboxymethyl cellulose (Ac-Di-Sol®, FMC Corporation, Philadelphia, Pa.), and (iii) sodium stearyl fumarate to form pharmaceutical composition No. 2, which was then compressed with a single stage Carver Press (round concave 0.3150" diameter (8 mm) with 8 kP hardness).

TABLE 3A

Pharmaceutical Composition No. 2

| Component | Function | mg/tablet | wt % |
|---|---|---|---|
| Formula (III) | Active Ingredient | 25 | 14.7 |
| Lactose | Filler | 72.5 | 42.6 |
| Microcrystalline cellulose | Filler | 53 | 31.2 |
| Carboxymethyl Cellulose Sodium | Disintegrant | 10 | 5.9 |
| Docusate Sodium | Surfactant | 2.5 | 1.5 |
| Hydroxypropyl Cellulose | Binder | 5 | 2.9 |
| Sodium Stearyl Fumarate | Lubricant | 2 | 1.2 |

TABLE 3B

Pharmaceutical Composition No. 2

| INGREDIENTS | mg | % |
|---|---|---|
| Granular Portion | | |
| Formula (III) | 25 | 14.7 |
| Lactose monohydrate (SD) | 72.5 | 42.6 |
| Microcrystalline Cellulose (MCC102) | 20 | 11.8 |
| Croscarmellose Sodium (Ac-Di-Sol) | 5 | 2.9 |
| Docusate sodium | 2.5 | 1.5 |
| Hydroxypropyl cellulose (Klucel EF) | 5 | 2.9 |
| Extra-Granular Portion | | |
| Croscarmellose Sodium (Ac-Di-Sol) | 5 | 2.9 |
| Microcrystalline Cellulose (MCC102) | 33 | 19.4 |
| Sodium Stearyl Fumarate, NF | 5 | 1.2 |

Example 4

Pharmaceutical Composition No. 3 (Formulation 003C) shown in Table 4A and Table 4B was prepared by the following process. Formula (III) was micronized in a jet mill until there was a particle size distribution with a D90 of 10 microns, as measured by laser diffraction spectroscopy. Thereafter, using the ratios for the granular portion shown in Table 4B, Formula (III) was blended with (i) mannitol (Parteck M100), (ii) 1 poloxamer F68, (iii) internally crosslinked sodium carboxymethyl cellulose (Ac-Di-Sol®, FMC Corporation, Philadelphia, Pa.), and (iv) hydroxypropyl cellulose (KLUCEL® EF, Ashland, Covington, Ky.). The blend was screened through a US standard #30 mesh (600 microns), then mixed again. The blend was wet granulated (mortar and pestle; 20% w/v granulation formed), and then dried at 60° C., and then screened through a US standard #30 mesh screen. Thereafter, using the ratios for the extra-granular portion shown in Table 4B, the granules were blended with (i) microcrystalline cellulose (MCC 102), (ii) internally crosslinked sodium carboxymethyl cellulose (Ac-Di-Sol®, FMC Corporation, Philadelphia, Pa.), and (iii) sodium stearyl fumarate to form Pharmaceutical Composition No. 3, which was then compressed with a single stage Carver Press (round concave 0.3150" diameter (8 mm) with 8 kP hardness).

TABLE 4A

Pharmaceutical Composition No. 3

| Component | Function | mg/tablet | wt % |
|---|---|---|---|
| Formula (III) | Active Ingredient | 25 | 14.7 |
| Mannitol (Parteck M100) | Filler | 80 | 47.1 |
| Poloxamer F68 | Filler | 15 | 8.8 |

TABLE 4A-continued

Pharmaceutical Composition No. 3

| Component | Function | mg/tablet | wt % |
|---|---|---|---|
| Carboxymethyl Cellulose Sodium | Disintegrant | 10 | 5.9 |
| Hydroxypropyl Cellulose | Binder | 5 | 2.9 |
| Microcrystalline Cellulose (MCC102) | Filler | 33 | 19.4 |
| Sodium Stearyl Fumarate | Lubricant | 2 | 1.2 |

TABLE 4B

Pharmaceutical Composition No. 3

| INGREDIENTS | mg | % |
|---|---|---|
| Granular Portion | | |
| Formula (III) | 25 | 14.7 |
| Mannitol (Parteck M100) | 80 | 47.1 |
| Croscarmellose Sodium (Ac-Di-Sol) | 5 | 2.9 |
| Poloxamer F68 | 15 | 8.8 |
| Hydroxypropyl cellulose (Klucel EF) | 5 | 2.9 |
| Extra-Granular Portion | | |
| Croscarmellose Sodium (Ac-Di-Sol) | 5 | 2.9 |
| Microcrystalline Cellulose (MCC102) | 33 | 19.4 |
| Sodium Stearyl Fumarate, NF | 5 | 1.2 |

Example 5

Figure 2:
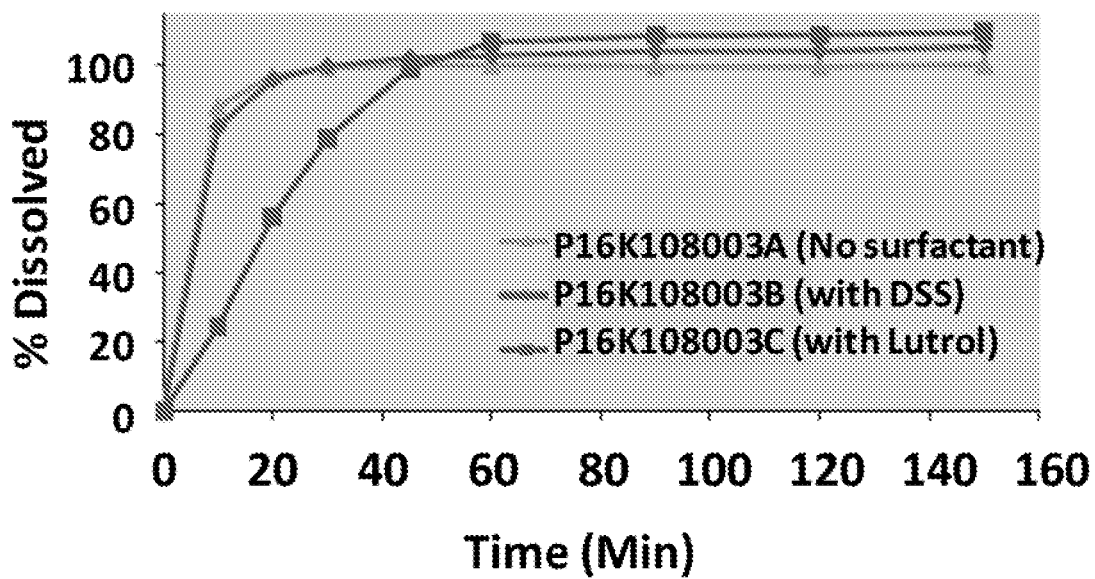
FIG. 2 is a graph showing the dissolution of Pharmaceutical Composition Nos. 1-3 per USP, Chapter <711>, Dissolution Test where the compositions were placed in a USP Apparatus 2 at a paddle speed of 50 rpm, in a dissolution medium of 0.1N HCl, 900 mL, at about 37° C.

Pharmaceutical Composition Nos. 1-3 were also subjected to the US Pharmacopoeia (USP), Chapter <711>, Dissolution Test where the compositions were placed in a USP Apparatus 2 at a paddle speed of 50 rpm, in a dissolution medium of 0.1N HCl, 900 mL, at about 37° C. The results are shown in FIG. 2. As can be seen from the results, Compositions No. 1 and 2 showed a dissolution of at least 80% within 10 minutes, while Composition No. 3 showed a dissolution of about 80% after 30 minutes.

Example 6

TABLE 6A

Pharmaceutical Composition No. 1

| | Formula (III) | Initial | 2 weeks open | 2 weeks closed | 4 weeks closed |
|---|---|---|---|---|---|
| Assay, % LC | — | 99.5 | 98.7 | 99.2 | 101.1 |
| Total Impurities | 0.80% | 0.83% | 0.52% | 0.45% | 1.18% |

TABLE 6B

Pharmaceutical Composition No. 2

| | Formula (III) | Initial | 2 weeks open | 2 weeks closed | 4 weeks closed |
|---|---|---|---|---|---|
| Assay, % LC | — | 106.3 | 104.8 | 104.9 | 107.2 |
| Total Impurities | 0.80% | 0.65% | 0.88% | 0.88% | 1.21% |

TABLE 6C

Pharmaceutical Composition No. 3

| | Formula (III) | Initial | 2 weeks open | 2 weeks closed | 4 weeks closed |
|---|---|---|---|---|---|
| Assay, % LC | — | 105.4 | 101.2 | 101.6 | 104.8 |
| Total Impurities | 0.80% | 0.75% | 0.75% | 0.56% | 1.14% |

Figure 3A:
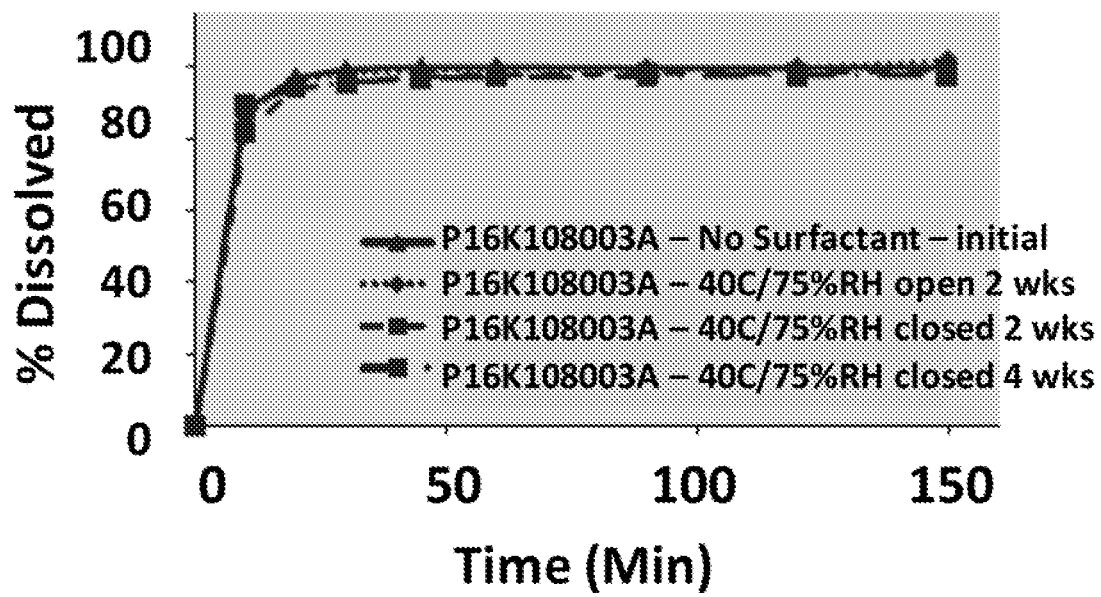
FIGS. 3A-3C are graphs showing the dissolution of Pharmaceutical Composition Nos. 1-3 per USP, Chapter <711>, Dissolution Test where the compositions were placed in a USP Apparatus 2 at a paddle speed of 50 rpm, in a dissolution medium of 0.1N HCl, 900 mL, at about 37° C., as a function of storage time at 40° C. and 75% relative humidity.
Figure 3B:
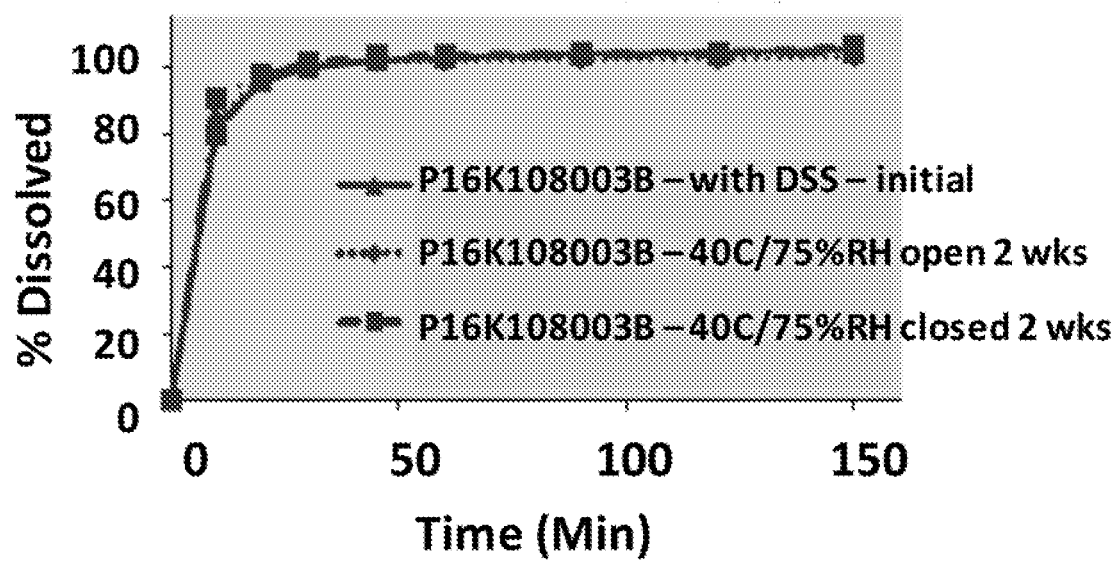
Figure 3C:
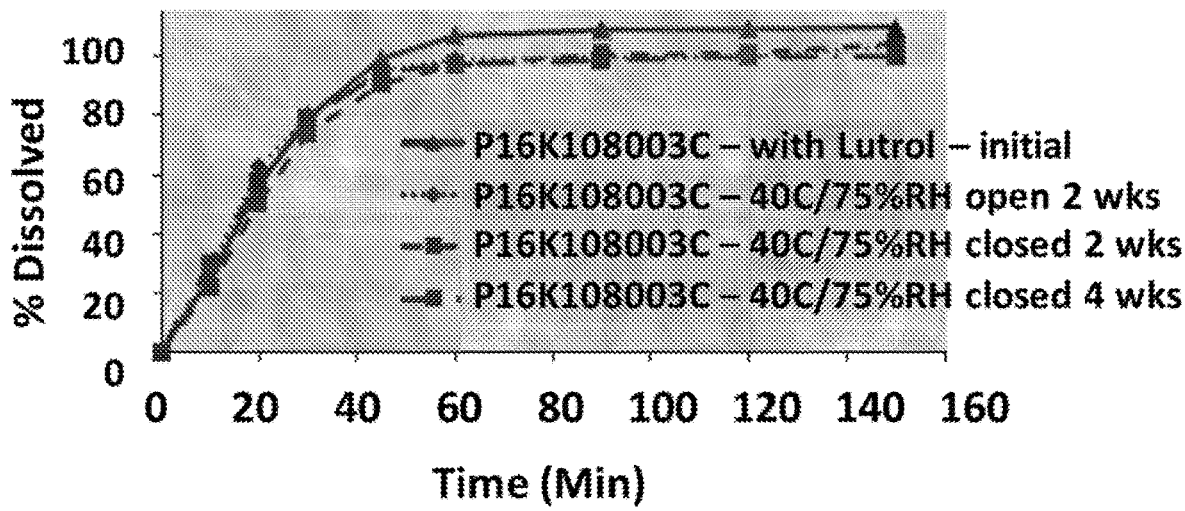

Pharmaceutical Composition Nos. 1-3 were also subjected to the US Pharmacopoeia (USP), Chapter <711>, Dissolution Test where the compositions were placed in a USP Apparatus 2 at a paddle speed of 50 rpm, in a dissolution medium of 0.1N HCl, 900 mL, at about 37° C., to determine if the dissolution would change under the accelerated storage conditions. The results for Pharmaceutical Composition Nos. 1-3 are shown in FIGS. 3A-3C, respectively.

Example 7

Pharmaceutical Composition No. 1, shown in Table 2A and Table 2B, was prepared by a slightly modified process (producing Formulation 029C), as follows. Formula (III) was micronized in a jet mill until there was a particle size distribution with a D90 of 10 microns, as measured by laser diffraction spectroscopy. Thereafter, using the ratios for the granular portion shown in Table 2B, Formula (III) was blended with (i) spray-dried lactose, (ii) microcrystalline cellulose (MCC 102), (iii) internally crosslinked sodium carboxymethyl cellulose (Ac-Di-Sol®, FMC Corporation, Philadelphia, Pa.), and (iv) hydroxypropyl cellulose (KLUCEL® EF, Ashland, Covington, Ky.). The blend was screened through a US standard #30 mesh (600 microns), then mixed again. The blend was granulated with a 2 liter Kitchen Aid Mixer (speed 4, with maximum of 10), dried at 50° C. for one hours, and then screened through a US standard #30 mesh screen. Using the ratios for the extra-granular portion shown in Table 2B, the granules were then blended with (i) microcrystalline cellulose (MCC 102), (ii) internally crosslinked sodium carboxymethyl cellulose (Ac-Di-Sol®, FMC Corporation, Philadelphia, Pa.), and (iii) sodium stearyl fumarate to form pharmaceutical composition No. 1, which was then compressed with a single stage tablet press (F-Press) (flat round punch 8.00 mm diameter). The weight, thickness, hardness, and disintegration time for 10 sample tablets are shown in Table 7A below.

TABLE 7A

| Sample | Weight (mg) | Thickness (mm) | Hardness (kP) | Disintegration Time (seconds) |
|---|---|---|---|---|
| 1 | 174 | 2.71 | 10.2 | 40 |
| 2 | 170 | 2.69 | 10.4 | 42 |
| 3 | 171 | 2.72 | 11.1 | 45 |
| 4 | 169 | 2.67 | 11.2 | |
| 5 | 171 | 2.72 | 10.1 | |
| 6 | 168 | 2.72 | 10.7 | |
| 7 | 172 | 2.71 | 11.4 | |
| 8 | 170 | 2.64 | 10.4 | |
| 9 | 167 | 2.71 | 9.9 | |
| 10 | 171 | 2.69 | 10.6 | |
| Average | 170.3 | 0.03 | 10.6 | |
| St. Dev. | 2.00 | 1.2 | 0.5 | |
| RSD | 1.2 | | 4.7 | |

Figure 4:
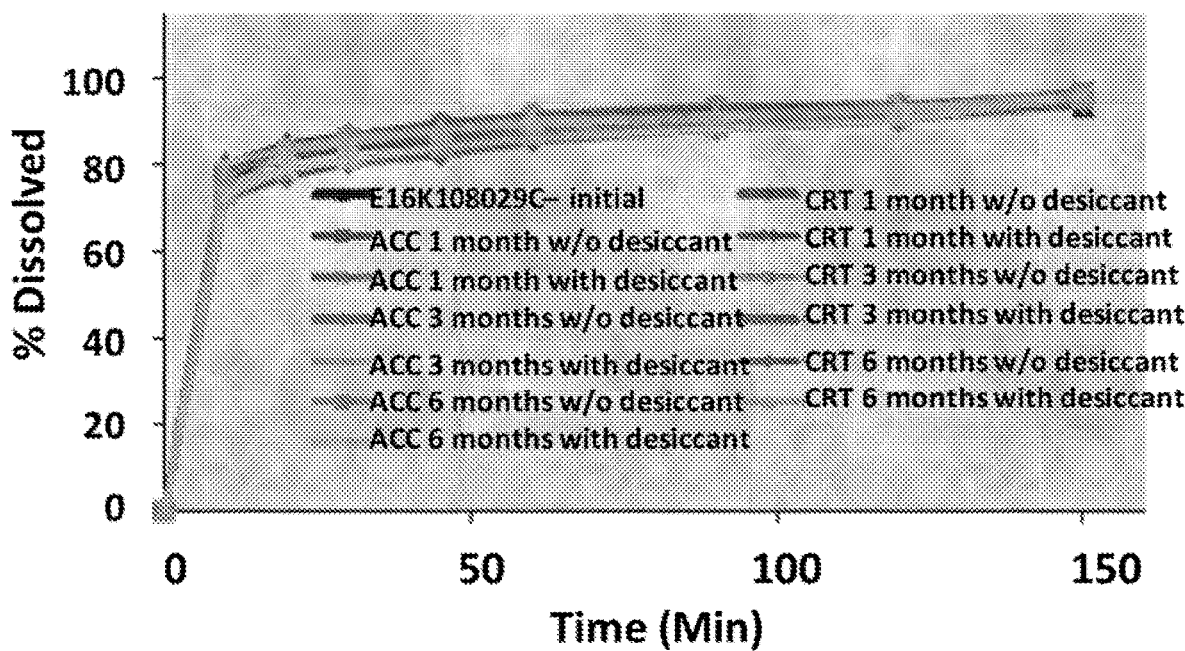
FIG. 4 shows the dissolution of Pharmaceutical Composition No. 1 per USP, Chapter <711>, Dissolution Test where the compositions were placed in a USP Apparatus 2 at a paddle speed of 50 rpm, in a dissolution medium of 0.1N HCl, 900 mL, at about 37° C. and a pH of 1.0, as a function of storage time at accelerated conditions (ACC) or controlled room temperature conditions (CRT).

The tablets were stored and monitored at accelerated conditions (ACC) of 40° C. and 75% relative humidity and controlled room temperature conditions (CRT) of 25° C. and 60% relative humidity in 75 cc HDPE bottles with 1 gram desiccant or without desiccant. The results are shown in Table 7B (storage without desiccant) and Table 7C (storage with desiccant). At each time point and each storage condition, tablets were characterized by dissolution testing for both storage conditions (FIG. 4). Dissolution was tested following US Pharmacopoeia (USP), Chapter <711>, Dissolution Test where the composition was placed in a USP Apparatus 2 at a paddle speed of 50 rpm, in a dissolution medium of 0.1N HCl, 900 mL, at about 37° C.

TABLE 7B

|  | API | Initial | 1 month CRT | 1 month ACC | 3 months CRT | 3 months ACC | 6 months CRT | 6 months ACC |
|---|---|---|---|---|---|---|---|---|
| Assay, % LC | — | 96.5 | 94.9 | 94.5 | 98.0 | 98.0 | 96.4 | 96.9 |
| Total Impurities (%) | 0.80 | 0.61 | 0.93 | 0.86 | 0.65 | 0.77 | 0.73 | 0.79 |

TABLE 7C

|  | API | Initial | 1 month CRT | 1 month ACC | 3 months CRT | 3 months ACC | 6 months CRT | 6 months ACC |
|---|---|---|---|---|---|---|---|---|
| Assay, % LC | — | 96.5 | 98.1 | 96.1 | 95.6 | 97.7 | 98.0 | 96.9 |
| Total Impurities (%) | 0.80 | 0.61 | 0.68 | 0.73 | 0.66 | 0.65 | 0.79 | 0.77 |

Example 8

Pharmaceutical Composition No. 4 shown in Table 8A and Table 8B was prepared by the following process. Formula (III) was micronized in a jet mill until there was a particle size distribution with a D90 of 10 microns, as measured by laser diffraction spectroscopy. Thereafter, using the ratios for the granular portion shown in Table 8B, Formula (III) was screened and then blended with (i) mannitol, USP, (ii) microcrystalline cellulose (MCC 102), and (iii) internally crosslinked sodium carboxymethyl cellulose (Ac-Di-Sol®, FMC Corporation, Philadelphia, Pa.), to form a blend. The blend was subjected to fluid bed granulation with hydroxypropyl cellulose (KLUCEL® EF, Ashland, Covington, Ky.) dissolved in water, and then dried. The granulated and dried blend was subjected to milling in a comminution hammer mill (FitzMill by Fitzpatrick®) to form granules. Using the ratios for the extra-granular portion shown in Table 8B, the granules were then blended with (i) microcrystalline cellulose (MCC 102), (ii) internally cross-linked sodium carboxymethyl cellulose (Ac-Di-Sol®, FMC Corporation, Philadelphia, Pa.), (iii) colloidal silicon dioxide, and (iv) sodium stearyl fumarate to form Pharmaceutical Composition No. 4, which was subsequently compressed into a tablet and coated with a target of 16 mg of OPADRY® white per tablet.

TABLE 8A

Pharmaceutical Composition No. 4

| Component | Function | mg/tablet | wt % |
|---|---|---|---|
| Formula (III) | Active Ingredient | 100 | 25.00 |
| Mannitol, USP | Filler | 157 | 39.25 |
| Microcrystalline cellulose, NF | Filler | 90 | 22.50 |
| Croscarmellose Sodium, NF | Disintegrant | 32 | 8.00 |
| Hydroxypropyl Cellulose, NF | Binder | 12 | 3.00 |
| Colloidal Silicon Dioxide, NF | Lubricant | 4 | 1.00 |
| Sodium Stearyl Fumarate | Lubricant | 5 | 1.25 |
| Total |  | 400 | 100.00 |

TABLE 8B

Pharmaceutical Composition No. 4

| INGREDIENTS | mg | % |
|---|---|---|
| Granular Portion | | |
| Formula (III) | 100 | 25.00 |
| Microcrystalline Cellulose, NF | 39 | 9.75 |
| Mannitol, USP | 157 | 39.25 |
| Croscarmellose Sodium, NF | 20 | 5.00 |
| Hydroxypropyl Cellulose, NF | 12 | 3.00 |
| Extra-Granular Portion | | |
| Microcrystalline Cellulose, NF | 51 | 12.75 |
| Croscarmellose Sodium, NF | 12 | 3.00 |
| Colloidal Silicon Dioxide, NF | 4 | 1.00 |
| Sodium Stearyl Fumarate, NF | 5 | 1.25 |
| Tablet Total | 400 | 100 |
| Film Coating Addition | | |
| OPADRY ® white | 16 | 4.00 |
| COATED TABLET | 416 | |

Example 9

Pharmaceutical Composition No. 5 shown in Table 9A and Table 9B was prepared by the following process. Formula (III) was micronized in a jet mill until there was a particle size distribution with a D90 of 10 microns, as measured by laser diffraction spectroscopy. Thereafter, using the ratios for the granular portion shown in Table 9B, Formula (III) was screened and then blended with (i) mannitol; (ii) microcrystalline cellulose, NF, and (iii) internally crosslinked sodium carboxymethyl cellulose (Ac-Di-Sol®, FMC Corporation, Philadelphia, Pa.), to form a blend. The mannitol was comprised of PERLITOL® 50C and PERLITOL® 200SD in a weight ratio of about 1.9:1. The blend was subjected to fluid bed granulation with a 5% w/w aqueous solution of hydroxypropyl cellulose (KLUCEL® EF, Ashland, Covington, Ky.), and then dried (whereby the water was removed from the formulation). The granulated and dried blend was subjected to milling in a comminution hammer mill (FitzMill by Fitzpatrick®) to form granules. Using the ratios for the extra-granular portion shown in Table 9B, the granules were then blended with (i) silicon dioxide, and (ii) sodium stearyl fumarate to form Pharmaceutical Composition No. 5. Thereafter, the composition was compressed into a tablet and each tablet was coated with a target of 12 mg of OPADRY® orange.

TABLE 9A

Pharmaceutical Composition No. 5

| Component | Function | mg/tablet | wt % |
|---|---|---|---|
| Formula (III) | Active Agent | 100 | 25.00 |
| Mannitol | Filler | 153 | 38.25 |
| Microcrystalline cellulose, NF | Filler | 90 | 22.50 |
| Croscarmellose Sodium, NF | Super Disintegrant | 32 | 8.00 |
| Hydroxypropyl Cellulose, NF | Binder | 16 | 4.00 |
| Silicon Dioxide | Flow Aid/Glidant | 4 | 1.00 |
| Sodium Stearyl Fumarate | Lubricant | 5 | 1.25 |
| Total | | 400 | 100.00 |

TABLE 9B

Pharmaceutical Composition No. 5

| INGREDIENTS | mg | % |
|---|---|---|
| Granular Portion | | |
| Formula (III) | 100 | 25.00 |
| Mannitol (PERLITOL® 200SD) | 52 | 13.00 |
| Mannitol (PERLITOL® 50C) | 101 | 25.25 |
| Microcrystalline Cellulose, NF | 90 | 22.50 |
| Croscarmellose Sodium, NF | 32 | 8.00 |
| Granulation Liquid | | |
| Hydroxypropyl Cellulose, NF (KLUCEL® EF) | 16 | 4.00 |
| Water | 320 | |
| Extra-Granular Portion | | |
| Silicon Dioxide, NF | 4 | 1.00 |
| Sodium Stearyl Fumarate, NF | 5 | 1.25 |
| Tablet Total | 400 | 100 |
| Film Coating Addition | | |
| OPADRY® orange | 12 | 3.00 |
| COATED TABLET | 412 | |

Figure 5:
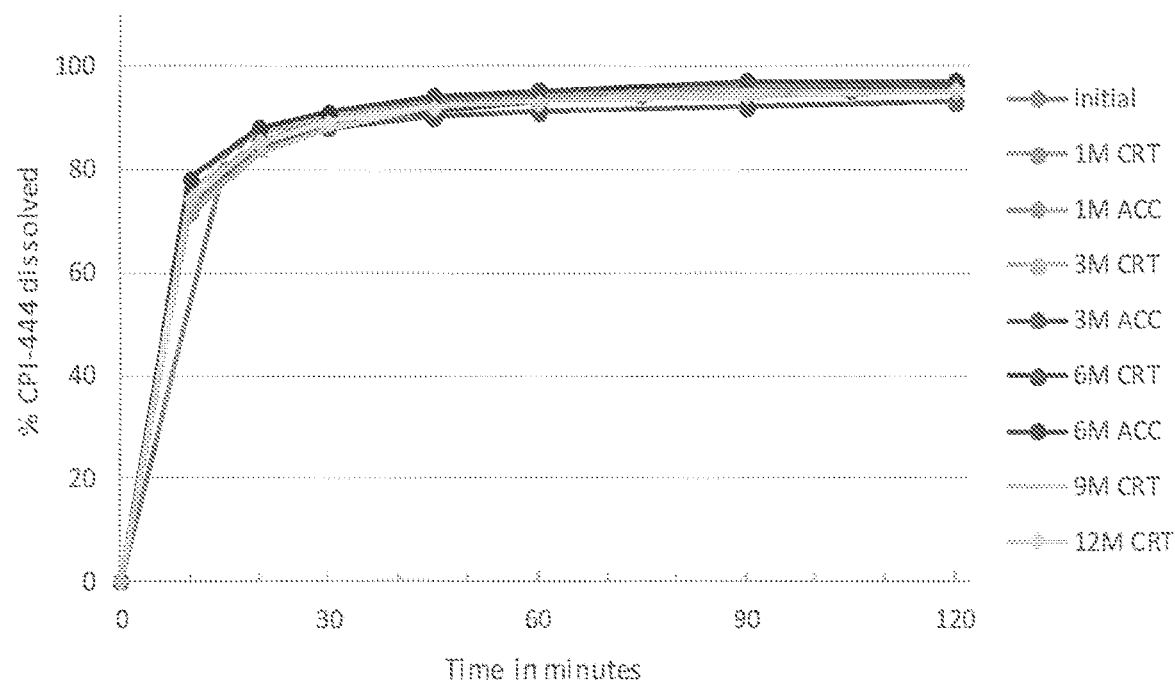
FIG. 5 shows the dissolution of Pharmaceutical Composition No. 5 per USP, Chapter <711>, Dissolution Test where the compositions were placed in a USP Apparatus 2 at a paddle speed of 50 rpm, in a dissolution medium of 0.1N HCl, 900 mL, at about 37° C. and a pH of 1.0, as a function of storage time at accelerated conditions (ACC) or controlled room temperature conditions (CRT).

The tablets were stored and monitored at accelerated conditions (ACC) of 40° C. and 75% relative humidity and controlled room temperature conditions (CRT) of 25° C. and 60% relative humidity in 75 cc HDPE bottles. The results are shown in Table 9C. At each time point and each storage condition, tablets were characterized by dissolution testing for both storage conditions (FIG. 5). Dissolution was tested following US Pharmacopoeia (USP), Chapter <711>, Dissolution Test where the composition was placed in a USP Apparatus 2 at a paddle speed of 50 rpm, in a dissolution medium of 0.1N HCl, 900 mL, at about 37° C.

TABLE 9C

| | Initial | 1 month CRT | 1 month ACC | 3 months CRT | 3 months ACC | 6 months CRT | 6 months ACC | 9 months CRT | 12 months CRT |
|---|---|---|---|---|---|---|---|---|---|
| Assay, % LC | 98.6 | 98.1 | 98.4 | 98.1 | 97.4 | 98.5 | 97.5 | 97.7 | 98.3 |
| Total Impurities (%) | 0.2 | 0.2 | 0.2 | 0.1 | 0.1 | 0.2 | 0.2 | 0.2 | 0.2 |

Example 10

Pharmaceutical Composition No. 5 was subjected to disintegration testing by US Pharmacopeia (USP), Chapter <701>, Disintegration Test method: basket-rack assembly, 1000 mL deionized water, 30 cycles/min. The composition had a disintegration time of less than 5 minutes.

Pharmaceutical Composition No. 5 was subjected to a dissolution test using US Pharmacopeia (USP), Chapter <711>, Type II (Paddle) Dissolution Apparatus 2, paddle speed 50 rpm in a medium of 0.1N HCl, 900 mL, 37°. As shown in FIG. 1, more than 80% of the drug in the composition dissolved in 30 minutes.

Example 11

Pharmaceutical composition No. 6 shown in Table 11A and Table 11B was prepared by the following process. Formula (III) was micronized in a jet mill until there was a particle size distribution with a D90 of 10 microns, as measured by laser diffraction spectroscopy. Thereafter, using the ratios for the granular portion shown in Table 11B, Formula (III) was screened and then blended with (i) mannitol; (ii) microcrystalline cellulose, NF, and (iii) internally crosslinked sodium carboxymethyl cellulose (Ac-Di-Sol®, FMC Corporation, Philadelphia, Pa.), to form a blend. Note that the mannitol was comprised of PERLITOL® 50C and PERLITOL® 200SD in a weight ratio of about 1.94:1. The blend was subjected to fluid bed granulation with a 5% w/w aqueous solution of hydroxypropyl cellulose (KLUCEL® EF, Ashland, Covington, Ky.), and then dried (whereby the water was removed from the formulation). The granulated and dried blend was subjected to milling in a comminution hammer mill (FitzMill by Fitzpatrick®) to form granules. Using the ratios for the extra-granular portion shown in Table 11B, the granules were then blended with (i) silicon dioxide, and (ii) sodium stearyl fumarate to form Pharmaceutical Composition No. 6. The composition was then compressed into a tablet and each tablet was coated with at target of 6 mg of OPADRY® beige.

TABLE 11A

Pharmaceutical Composition No. 6

| Component | Function | mg/tablet | wt % |
|---|---|---|---|
| Formula (III) | Active Agent | 50 | 25.00 |
| Mannitol | Filler | 76.5 | 38.25 |
| Microcrystalline cellulose, NF | Filler | 45 | 22.50 |
| Croscarmellose Sodium, NF | Super Disintegrant | 16 | 8.00 |
| Hydroxypropyl Cellulose, NF | Binder | 8 | 4.00 |
| Silicon Dioxide | Flow Aid/Glidant | 2 | 1.00 |
| Sodium Stearyl Fumarate | Lubricant | 2.5 | 1.25 |
| Total | | 400 | 100.00 |

TABLE 11B

Pharmaceutical Composition No. 6

| INGREDIENTS | mg | % |
|---|---|---|
| Granular Portion | | |
| Formula (III) | 50 | 25.00 |
| Mannitol (PERLITOL® 200SD) | 26 | 13.00 |
| Mannitol (PERLITOL® 50C) | 50.5 | 25.25 |
| Microcrystalline Cellulose, NF | 45 | 22.50 |
| Croscarmellose Sodium, NF | 16 | 8.00 |
| Granulation Liquid | | |
| Hydroxypropyl Cellulose, NF (KLUCEL® EF) | 8 | 4.00 |
| Water | 160 | |
| Extra-Granular Portion | | |
| Silicon Dioxide, NF | 2 | 1.00 |
| Sodium Stearyl Fumarate, NF | 2.5 | 1.25 |
| Tablet Total | 200 | 100 |
| Film Coating Addition | | |
| OPADRY® beige | 6 | 3.00 |
| COATED TABLET | 206 | |

Example 12

Beads will be prepared by the following process. Formula (III) will be micronized by dry or wet milling until there is a particle size distribution with a D90 of 10 microns, as measured by laser diffraction spectroscopy. Thereafter, Formula (III) will be placed in a suspension with excipients as described herein to form a drug suspension. The drug/excipient suspension will be sprayed onto inert cores (e.g., sugar spheres, cellulose spheres) to form a drug layer on the inert core. In aspects, the inert core will be a sugar sphere #30-35 (500-600 microns). A protective coating layer will optionally be used to coat the beads. In aspects, the protective coating will contain HPC (KLUCEL® EF) and talc. A lubricant will optionally be added to prevent the beads from adhering to each other. In aspects, the coated beads will be filled into capsule shells. Additional excipients may optionally be blended with the beads before filling into the capsules. In aspects, the beads can be mixed with other excipients and compressed into a tablet. In aspects, the process conditions will be as shown in Table 12.

TABLE 12

Process Conditions

| Fluid Bed | Vector FL-1 Fluid Bed |
|---|---|
| Product Temperature | 50° C. |
| Nozzle Tip Diameter | 1.0 mm |
| Inlet Temperature | 54° C. to 64° C. |
| Exhaust Temperature | 48° C. to 53° C. |
| Spray Rate | 0.2 to 2 g/minute |
| Atomization Air Pressure | 30-40 bar |
| Air Volume | 63-64 CFM |

The section headings used herein are for organizational purposes only and are not to be construed as limiting the subject matter described. All documents, or portions of documents, cited in the application including, are incorporated by reference in their entirety for any purpose.

While various embodiments and aspects are shown and described herein, it will be obvious to those skilled in the art that such embodiments and aspects are provided by way of example only. Numerous variations, changes, and substitutions will now occur to those skilled in the art. It should be understood that various alternatives to the embodiments described herein may be employed.

What is claimed is:

1. A composition comprising:
about 20 wt % to about 30 wt % of a compound of Formula (III) or a pharmaceutically acceptable salt thereof having a particle size distribution with a D90 of about 20 microns or less, as measured by laser diffraction spectroscopy;
(ii) about 35 wt % to about 40 wt % of mannitol;
(iii) about 15 wt % to about 30 wt % of microcrystalline cellulose;
(iv) about 4 wt % to about 12 wt % of crosslinked sodium carboxymethyl cellulose; and
(v) about 1 wt % to about 8 wt % of hydroxypropyl cellulose;
wherein the compound of Formula (III) is:

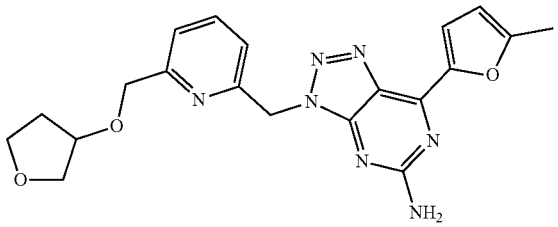

(III)

2. The composition of claim 1, comprising:
(i) about 24 wt % to about 26 wt % of the compound of Formula (III) or the pharmaceutically acceptable salt thereof;
(ii) about 37 wt % to about 40 wt % of mannitol;
(iii) about 20 wt % to about 25 wt % of microcrystalline cellulose;
(iv) about 4 wt % to about 12 wt % of crosslinked sodium carboxymethyl cellulose; and
(v) about 2 wt % to about 6 wt % of hydroxypropyl cellulose.

3. The composition of claim 2, comprising:
(i) about 25 wt % of the compound of Formula (III) or the pharmaceutically acceptable salt thereof;
(ii) about 38.25 wt % of mannitol;
(iii) about 22.5 wt % of microcrystalline cellulose;
(iv) about 8 wt % of crosslinked sodium carboxymethyl cellulose; and
(v) about 4 wt % of hydroxypropyl cellulose.

4. The composition of claim 1, wherein the mannitol comprises a spray-dried mannitol and a crystalline mannitol in a weight ratio from about 1:1 to about 1:3.

5. The composition of claim 4, wherein the mannitol comprises a spray-dried mannitol and a crystalline mannitol in a weight ratio from about 1:1.5 to about 1:2.5.

6. The composition of claim 1, wherein the compound of Formula (III) or the pharmaceutically acceptable salt thereof has a particle size distribution with a D90 of about 10 microns or less, as measured by laser diffraction spectroscopy.

7. The composition of claim 1, comprising from about 100 mg to about 400 mg of the compound of Formula (III) or the pharmaceutically acceptable salt thereof.

8. The composition of claim 7, comprising from about 200 mg of the compound of Formula (III) or the pharmaceutically acceptable salt thereof.

9. The composition of claim 1, wherein the compound of Formula (III) is 7-(5-methylfuran-2-yl)-3-[[6-[[(3S)-oxolan-3-yl]oxymethyl]pyridin-2-yl]methyl]triazolo[4,5-d]pyrimidin-5-amine.

10. The composition of claim 1 having a disintegration time of about 15 minutes or less, as measured by US Pharmacopeia (USP), Chapter <701>, Disintegration Test method.

11. The composition of claim 1 having a dissolution of at least 70% in 10 minutes, as measured by US Pharmacopeia (USP), Chapter <711>, Type II (Paddle) Dissolution Apparatus method.

12. A tablet comprising the composition of claim 1.

13. A powder comprising the composition of claim 1.

14. A granule comprising the composition of claim 1.

15. A capsule comprising the composition of claim 1.

16. A bead comprising an inert core and a drug layer; wherein the drug layer comprises the composition of claim 1, wherein the core has a particle size from about 100 microns to about 2.5 mm.

* * * * *